(12) United States Patent
Reckling et al.

(10) Patent No.: US 11,147,688 B2
(45) Date of Patent: *Oct. 19, 2021

(54) IMPLANT PLACEMENT

(71) Applicant: SI-Bone Inc., Santa Clara, CA (US)

(72) Inventors: W. Carlton Reckling, Cheyenne, WY (US); Mark A. Reiley, Washington, DC (US); Scott A. Yerby, Montara, CA (US); Sean Farley, O'Fallon, MO (US); Joanne Leung, Mountain View, CA (US)

(73) Assignee: SI-Bone Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/838,070

(22) Filed: Dec. 11, 2017

(65) Prior Publication Data
US 2018/0104071 A1 Apr. 19, 2018

Related U.S. Application Data

(63) Continuation-in-part of application No. 14/515,416, filed on Oct. 15, 2014, now Pat. No. 9,839,448.
(Continued)

(51) Int. Cl.
*A61F 2/46* (2006.01)
*A61B 6/12* (2006.01)
(Continued)

(52) U.S. Cl.
CPC ............ *A61F 2/4603* (2013.01); *A61B 6/032* (2013.01); *A61B 6/12* (2013.01); *A61B 6/4441* (2013.01);
(Continued)

(58) Field of Classification Search
CPC .......... A61F 2/4603; A61F 2002/30622; A61F 2002/4662; A61B 17/1637
See application file for complete search history.

(56) References Cited

U.S. PATENT DOCUMENTS

| | | |
|---|---|---|
| 1,951,278 A | 3/1934 | Ericsson |
| 2,136,471 A | 11/1938 | Schneider |

(Continued)

FOREIGN PATENT DOCUMENTS

| | | |
|---|---|---|
| CN | 1128944 A | 8/1996 |
| CN | 1190882 A | 8/1998 |

(Continued)

OTHER PUBLICATIONS

Sand et al.; U.S. Appl. No. 16/143,061 entitled "Systems and methods for decorticating the sacroiliac joint," filed Sep. 26, 2018.
(Continued)

*Primary Examiner* — Eduardo C Robert
*Assistant Examiner* — Tara Rose E Carter
(74) *Attorney, Agent, or Firm* — Shay Glenn LLP; Thomas M. Zlogar

(57) ABSTRACT

Embodiments of the present invention relate generally to implant placement into bone. More specifically, embodiments of the invention relate to implant placement across the sacro-iliac joint. Placement can be facilitated using various CT imaging views that allow the implants to be placed in bone associated with articular cartilage.

13 Claims, 39 Drawing Sheets

Related U.S. Application Data

(60) Provisional application No. 61/891,326, filed on Oct. 15, 2013.

(51) Int. Cl.
*A61B 6/03* (2006.01)
*A61B 6/00* (2006.01)
*A61B 17/68* (2006.01)
*A61B 17/16* (2006.01)
*A61F 2/30* (2006.01)
*A61B 6/04* (2006.01)
*A61B 17/92* (2006.01)
*A61B 17/88* (2006.01)

(52) U.S. Cl.
CPC .......... *A61B 6/505* (2013.01); *A61B 17/1659* (2013.01); *A61B 17/68* (2013.01); *A61B 6/0407* (2013.01); *A61B 17/1637* (2013.01); *A61B 17/1664* (2013.01); *A61B 17/8897* (2013.01); *A61B 2017/922* (2013.01); *A61F 2002/30622* (2013.01); *A61F 2002/30995* (2013.01); *A61F 2002/4662* (2013.01); *A61F 2002/4681* (2013.01)

(56) References Cited

U.S. PATENT DOCUMENTS

| | | |
|---|---|---|
| 2,243,717 A | 5/1941 | Moreira |
| 2,414,882 A | 7/1947 | Longfellow |
| 2,562,419 A | 7/1951 | Ferris |
| 2,675,801 A | 4/1954 | Bambara et al. |
| 2,697,433 A | 12/1954 | Zehnder |
| 3,076,453 A | 2/1963 | Tronzo |
| 3,506,982 A | 4/1970 | Steffee |
| 3,694,821 A | 10/1972 | Moritz |
| 3,709,218 A | 1/1973 | Halloran |
| 3,744,488 A | 7/1973 | Cox |
| 4,059,115 A | 11/1977 | Jumashev et al. |
| 4,156,943 A | 6/1979 | Collier |
| 4,292,964 A | 10/1981 | Ulrich |
| 4,341,206 A | 7/1982 | Perrett et al. |
| 4,344,190 A | 8/1982 | Lee et al. |
| 4,399,813 A | 8/1983 | Barber |
| 4,423,721 A | 1/1984 | Otte et al. |
| 4,475,545 A | 10/1984 | Ender |
| 4,501,269 A | 2/1985 | Bagby |
| 4,569,338 A | 2/1986 | Edwards |
| 4,612,918 A | 9/1986 | Slocum |
| 4,622,959 A | 11/1986 | Marcus |
| 4,630,601 A | 12/1986 | Harder et al. |
| 4,638,799 A | 1/1987 | Moore |
| 4,657,550 A | 4/1987 | Daher |
| 4,743,256 A | 5/1988 | Brantigan |
| 4,773,402 A | 9/1988 | Asher et al. |
| 4,787,378 A | 11/1988 | Sodhi |
| 4,790,303 A | 12/1988 | Steffee |
| 4,834,757 A | 5/1989 | Brantigan |
| 4,846,162 A | 7/1989 | Moehring |
| 4,877,019 A | 10/1989 | Vives |
| 4,878,915 A | 11/1989 | Brantigan |
| 4,898,186 A | 2/1990 | Ikada et al. |
| 4,904,261 A | 2/1990 | Dove et al. |
| 4,950,270 A | 8/1990 | Bowman et al. |
| 4,961,740 A | 10/1990 | Ray et al. |
| 4,969,888 A | 11/1990 | Scholten et al. |
| 4,981,481 A | 1/1991 | Kranz et al. |
| 5,034,011 A | 7/1991 | Howland |
| 5,034,013 A | 7/1991 | Kyle et al. |
| 5,035,697 A | 7/1991 | Frigg |
| 5,041,118 A | 8/1991 | Wasilewski |
| 5,053,035 A | 10/1991 | McLaren |
| 5,059,193 A | 10/1991 | Kuslich |
| 5,066,296 A | 11/1991 | Chapman et al. |
| 5,102,414 A | 4/1992 | Kirsch |
| 5,108,397 A | 4/1992 | White |
| 5,122,141 A | 6/1992 | Simpson et al. |
| 5,139,498 A | 8/1992 | Astudillo Ley |
| 5,139,500 A | 8/1992 | Schwartz |
| 5,147,367 A | 9/1992 | Ellis |
| 5,147,402 A | 9/1992 | Bohler et al. |
| 5,190,551 A | 3/1993 | Chin et al. |
| 5,197,961 A | 3/1993 | Castle |
| 5,242,444 A | 9/1993 | MacMillan |
| 5,298,254 A | 3/1994 | Prewett et al. |
| 5,334,205 A | 8/1994 | Cain |
| 5,380,325 A | 1/1995 | Lahille et al. |
| 5,390,683 A | 2/1995 | Pisharodi |
| 5,433,718 A | 7/1995 | Brinker |
| 5,443,466 A | 8/1995 | Shah |
| 5,458,638 A | 10/1995 | Kuslich et al. |
| 5,470,334 A | 11/1995 | Ross et al. |
| 5,480,402 A | 1/1996 | Kim |
| 5,569,249 A | 10/1996 | James et al. |
| 5,591,235 A | 1/1997 | Kuslich |
| 5,593,409 A | 1/1997 | Michelson |
| 5,607,424 A | 3/1997 | Tropiano |
| 5,609,635 A | 3/1997 | Michelson |
| 5,609,636 A | 3/1997 | Kohrs et al. |
| 5,626,616 A | 5/1997 | Speece |
| 5,643,264 A | 7/1997 | Sherman et al. |
| 5,645,599 A | 7/1997 | Samani |
| 5,658,337 A | 8/1997 | Kohrs et al. |
| 5,667,510 A | 9/1997 | Combs |
| 5,669,909 A | 9/1997 | Zdeblick et al. |
| 5,672,178 A | 9/1997 | Petersen |
| 5,683,391 A | 11/1997 | Boyd |
| 5,709,683 A | 1/1998 | Bagby |
| 5,713,904 A | 2/1998 | Errico et al. |
| 5,716,358 A | 2/1998 | Ochoa et al. |
| 5,725,581 A | 3/1998 | Brånemark |
| 5,743,912 A | 4/1998 | LaHille et al. |
| 5,759,035 A | 6/1998 | Ricci |
| 5,766,174 A | 6/1998 | Perry |
| 5,766,252 A | 6/1998 | Henry et al. |
| 5,766,261 A | 6/1998 | Neal et al. |
| 5,788,699 A | 8/1998 | Bobst et al. |
| 5,800,440 A | 9/1998 | Stead |
| 5,868,749 A | 2/1999 | Reed |
| 5,897,556 A | 4/1999 | Drewry et al. |
| 5,928,239 A | 7/1999 | Mirza |
| 5,941,885 A | 8/1999 | Jackson |
| 5,961,522 A | 10/1999 | Mehdizadeh |
| 5,961,554 A | 10/1999 | Janson et al. |
| 6,010,507 A | 1/2000 | Rudloff |
| 6,015,409 A | 1/2000 | Jackson |
| 6,030,162 A | 2/2000 | Huebner et al. |
| 6,053,916 A | 4/2000 | Moore |
| 6,056,749 A | 5/2000 | Kuslich |
| 6,066,175 A | 5/2000 | Henderson et al. |
| 6,086,589 A | 7/2000 | Kuslich et al. |
| 6,096,080 A | 8/2000 | Nicholson et al. |
| 6,120,292 A | 9/2000 | Buser et al. |
| 6,120,504 A | 9/2000 | Brumback et al. |
| 6,143,031 A | 11/2000 | Knothe et al. |
| 6,197,062 B1 | 3/2001 | Fenlin |
| 6,206,924 B1 | 3/2001 | Timm |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,264,657 B1 | 7/2001 | Urbahns et al. |
| 6,270,528 B1 | 8/2001 | McKay |
| 6,287,343 B1 | 9/2001 | Kuslich et al. |
| 6,302,885 B1 | 10/2001 | Essiger |
| 6,302,914 B1 | 10/2001 | Michelson |
| 6,306,140 B1 | 10/2001 | Siddiqui |
| 6,319,253 B1 | 11/2001 | Ackeret et al. |
| 6,406,498 B1 | 6/2002 | Tormala et al. |
| 6,409,768 B1 | 6/2002 | Tepic et al. |
| 6,451,020 B1 | 9/2002 | Zucherman et al. |
| 6,471,707 B1 | 10/2002 | Miller et al. |
| 6,485,518 B1 | 11/2002 | Cornwall et al. |

(56) References Cited

U.S. PATENT DOCUMENTS

| | | |
|---|---|---|
| 6,497,707 B1 | 12/2002 | Bowman et al. |
| 6,517,541 B1 | 2/2003 | Sesic |
| 6,520,969 B2 | 2/2003 | Lambrecht et al. |
| 6,524,314 B1 | 2/2003 | Dean et al. |
| 6,527,775 B1 | 3/2003 | Warburton |
| 6,556,857 B1 | 4/2003 | Estes et al. |
| 6,558,386 B1 | 5/2003 | Cragg |
| 6,565,566 B1 | 5/2003 | Wagner et al. |
| 6,575,899 B1 | 6/2003 | Foley et al. |
| 6,575,991 B1 | 6/2003 | Chesbrough et al. |
| 6,579,293 B1 | 6/2003 | Chandran |
| 6,582,431 B1 | 6/2003 | Ray |
| 6,582,467 B1 | 6/2003 | Teitelbaum et al. |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,607,530 B1 | 8/2003 | Carl et al. |
| 6,620,163 B1 | 9/2003 | Michelson |
| 6,635,059 B2 | 10/2003 | Randall et al. |
| 6,666,868 B2 | 12/2003 | Fallin |
| 6,669,529 B1 | 12/2003 | Scaries |
| 6,673,075 B2 | 1/2004 | Santilli |
| 6,692,501 B2 | 2/2004 | Michelson |
| 6,712,852 B1 | 3/2004 | Chung et al. |
| 6,723,099 B1 | 4/2004 | Goshert |
| 6,740,118 B2 | 5/2004 | Eisermann et al. |
| 6,743,257 B2 | 6/2004 | Castro |
| D493,533 S | 7/2004 | Blain |
| 6,793,656 B1 | 9/2004 | Mathews |
| 6,827,740 B1 | 12/2004 | Michelson |
| 6,984,235 B2 | 1/2006 | Huebner |
| 6,989,033 B1 | 1/2006 | Schmidt |
| 6,991,461 B2 | 1/2006 | Gittleman |
| 7,118,579 B2 | 10/2006 | Michelson |
| 7,147,666 B1 | 12/2006 | Grisoni |
| 7,175,663 B1 | 2/2007 | Stone |
| 7,211,085 B2 | 5/2007 | Michelson |
| 7,223,269 B2 | 5/2007 | Chappuis |
| 7,314,488 B2 | 1/2008 | Reiley |
| 7,335,205 B2 | 2/2008 | Aeschlimann et al. |
| 7,338,500 B2 | 3/2008 | Chappuis |
| 7,396,365 B2 | 7/2008 | Michelson |
| 7,452,359 B1 | 11/2008 | Michelson |
| 7,452,369 B2 | 11/2008 | Barry |
| 7,481,831 B2 | 1/2009 | Bonutti |
| 7,527,649 B1 | 5/2009 | Blain |
| 7,534,254 B1 | 5/2009 | Michelson |
| 7,537,616 B1 | 5/2009 | Branch et al. |
| 7,569,054 B2 | 8/2009 | Michelson |
| 7,569,059 B2 | 8/2009 | Cerundolo |
| 7,601,155 B2 | 10/2009 | Petersen |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,727,235 B2 | 6/2010 | Contiliano et al. |
| 7,758,646 B2 | 7/2010 | Khandkar et al. |
| 7,780,704 B2 | 8/2010 | Markworth et al. |
| 7,846,162 B2 | 12/2010 | Nelson et al. |
| 7,850,732 B2 | 12/2010 | Heinz |
| 7,857,832 B2 | 12/2010 | Culbert et al. |
| 7,887,565 B2 | 2/2011 | Michelson |
| 7,901,439 B2 | 3/2011 | Horton |
| 7,909,832 B2 | 3/2011 | Michelson |
| 7,922,765 B2 | 4/2011 | Reiley |
| 7,942,879 B2 | 5/2011 | Christie et al. |
| 8,052,728 B2 | 11/2011 | Hestad |
| 8,062,365 B2 | 11/2011 | Schwab |
| 8,066,705 B2 | 11/2011 | Michelson |
| 8,066,709 B2 | 11/2011 | Michelson |
| 8,142,481 B2 | 3/2012 | Warnick |
| 8,202,305 B2 | 6/2012 | Reiley |
| 8,308,779 B2 | 11/2012 | Reiley |
| 8,317,862 B2 | 11/2012 | Troger et al. |
| 8,348,950 B2 | 1/2013 | Assell et al. |
| 8,388,667 B2 | 3/2013 | Reiley et al. |
| 8,394,129 B2 | 3/2013 | Morgenstern Lopez |
| 8,398,635 B2 | 3/2013 | Vaidya |
| 8,414,648 B2 | 4/2013 | Reiley |
| 8,425,570 B2 | 4/2013 | Reiley |
| 8,430,930 B2 | 4/2013 | Hunt |
| 8,444,693 B2 | 5/2013 | Reiley |
| 8,467,851 B2 | 6/2013 | Mire et al. |
| 8,470,004 B2 | 6/2013 | Reiley |
| 8,529,608 B2 | 9/2013 | Terrill et al. |
| 8,608,802 B2 | 12/2013 | Bagga et al. |
| D697,209 S | 1/2014 | Walthall et al. |
| 8,641,737 B2 | 2/2014 | Matthis et al. |
| 8,663,332 B1 | 3/2014 | To et al. |
| 8,672,986 B2 | 3/2014 | Klaue et al. |
| 8,734,462 B2 | 5/2014 | Reiley et al. |
| 8,778,026 B2 | 7/2014 | Mauldin |
| 8,840,623 B2 | 9/2014 | Reiley |
| 8,840,651 B2 | 9/2014 | Reiley |
| 8,845,693 B2 | 9/2014 | Smith et al. |
| 8,858,601 B2 | 10/2014 | Reiley |
| 8,920,477 B2 | 12/2014 | Reiley |
| 8,945,190 B2 | 2/2015 | Culbert et al. |
| 8,945,193 B2 | 2/2015 | Kirschman |
| 8,951,254 B2 | 2/2015 | Mayer et al. |
| 8,951,293 B2 | 2/2015 | Glazer et al. |
| 8,951,295 B2 | 2/2015 | Matityahu et al. |
| 8,961,571 B2 | 2/2015 | Lee et al. |
| 8,986,348 B2 | 3/2015 | Reiley |
| RE45,484 E | 4/2015 | Foley et al. |
| 9,039,743 B2 | 5/2015 | Reiley |
| 9,044,321 B2 | 6/2015 | Mauldin et al. |
| 9,060,876 B1 | 6/2015 | To et al. |
| 9,089,371 B1 | 7/2015 | Faulhaber |
| D738,498 S | 9/2015 | Frey et al. |
| 9,131,955 B2 | 9/2015 | Swofford |
| 9,149,286 B1 | 10/2015 | Greenhalgh et al. |
| 9,198,676 B2 | 12/2015 | Pilgeram et al. |
| 9,220,535 B2 | 12/2015 | Röbling et al. |
| 9,314,348 B2 | 4/2016 | Emstad |
| 9,358,057 B1 | 6/2016 | Whipple et al. |
| 9,375,243 B1 | 6/2016 | Vestgaarden |
| 9,375,323 B2 | 6/2016 | Reiley |
| 9,451,999 B2 | 9/2016 | Simpson et al. |
| 9,452,065 B1 | 9/2016 | Lawson |
| 9,486,264 B2 | 11/2016 | Reiley et al. |
| 9,492,201 B2 | 11/2016 | Reiley |
| 9,498,264 B2 | 11/2016 | Harshman et al. |
| 9,510,872 B2 | 12/2016 | Donner et al. |
| 9,517,095 B2 | 12/2016 | Vaidya |
| 9,526,548 B2 | 12/2016 | Asfora |
| 9,554,909 B2 | 1/2017 | Donner |
| 9,561,063 B2 | 2/2017 | Reiley |
| 9,566,100 B2 | 2/2017 | Asfora |
| 9,603,613 B2 | 3/2017 | Schoenefeld et al. |
| 9,615,856 B2 | 4/2017 | Arnett et al. |
| 9,622,783 B2 | 4/2017 | Reiley et al. |
| 9,636,226 B2 | 5/2017 | Hunt |
| 9,655,656 B2 | 5/2017 | Whipple |
| 9,662,124 B2 | 5/2017 | Assell et al. |
| 9,662,128 B2 | 5/2017 | Reiley |
| 9,662,157 B2 | 5/2017 | Schneider et al. |
| 9,662,158 B2 | 5/2017 | Reiley |
| 9,675,394 B2 | 6/2017 | Reiley |
| 9,743,969 B2 | 8/2017 | Reiley |
| 9,757,154 B2 | 9/2017 | Donner et al. |
| 9,763,695 B2 | 9/2017 | Mirda |
| 9,820,789 B2 | 11/2017 | Reiley |
| 9,839,448 B2 | 12/2017 | Reckling et al. |
| 10,219,885 B2 | 3/2019 | Mamo et al. |
| 10,492,921 B2 | 12/2019 | McShane, III et al. |
| 10,743,995 B2 | 8/2020 | Fallin et al. |
| 10,799,367 B2 | 10/2020 | Vrionis et al. |
| 2001/0012942 A1 | 8/2001 | Estes et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0019637 A1 | 2/2002 | Frey et al. |
| 2002/0029043 A1 | 3/2002 | Ahrens et al. |

(56) References Cited

U.S. PATENT DOCUMENTS

| | | |
|---|---|---|
| 2002/0038123 A1 | 3/2002 | Visotsky et al. |
| 2002/0049497 A1 | 4/2002 | Mason |
| 2002/0077641 A1 | 6/2002 | Michelson |
| 2002/0082598 A1 | 6/2002 | Teitelbaum |
| 2002/0120275 A1 | 8/2002 | Schmieding et al. |
| 2002/0128652 A1 | 9/2002 | Ferree |
| 2002/0143334 A1 | 10/2002 | von Hoffmann et al. |
| 2002/0143335 A1 | 10/2002 | Von Hoffmann et al. |
| 2002/0151903 A1 | 10/2002 | Takei et al. |
| 2002/0169507 A1 | 11/2002 | Malone |
| 2002/0183858 A1 | 12/2002 | Contiliano et al. |
| 2002/0198527 A1 | 12/2002 | Mückter |
| 2003/0018336 A1 | 1/2003 | Vandewalle |
| 2003/0032961 A1 | 2/2003 | Pelo et al. |
| 2003/0050642 A1 | 3/2003 | Schmieding et al. |
| 2003/0065332 A1 | 4/2003 | TenHuisen et al. |
| 2003/0074000 A1 | 4/2003 | Roth et al. |
| 2003/0078660 A1 | 4/2003 | Clifford et al. |
| 2003/0083668 A1 | 5/2003 | Rogers et al. |
| 2003/0083688 A1 | 5/2003 | Simonson |
| 2003/0097131 A1 | 5/2003 | Schon et al. |
| 2003/0139815 A1 | 7/2003 | Grooms et al. |
| 2003/0181979 A1 | 9/2003 | Ferree |
| 2003/0181982 A1 | 9/2003 | Kuslich |
| 2003/0199983 A1 | 10/2003 | Michelson |
| 2003/0229358 A1 | 12/2003 | Errico et al. |
| 2003/0233146 A1 | 12/2003 | Grinberg et al. |
| 2003/0233147 A1 | 12/2003 | Nicholson et al. |
| 2004/0010315 A1 | 1/2004 | Song |
| 2004/0024458 A1 | 2/2004 | Senegas et al. |
| 2004/0034422 A1 | 2/2004 | Errico et al. |
| 2004/0073216 A1 | 4/2004 | Lieberman |
| 2004/0073314 A1 | 4/2004 | White et al. |
| 2004/0082955 A1 | 4/2004 | Zirkle |
| 2004/0087948 A1 | 5/2004 | Suddaby |
| 2004/0097927 A1 | 5/2004 | Yeung et al. |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0138750 A1 | 7/2004 | Mitchell |
| 2004/0138753 A1 | 7/2004 | Ferree |
| 2004/0147929 A1 | 7/2004 | Biedermann et al. |
| 2004/0158324 A1 | 8/2004 | Lange |
| 2004/0176287 A1 | 9/2004 | Harrison et al. |
| 2004/0176853 A1 | 9/2004 | Sennett et al. |
| 2004/0181282 A1 | 9/2004 | Zucherman et al. |
| 2004/0186572 A1 | 9/2004 | Lange et al. |
| 2004/0210221 A1 | 10/2004 | Kozak et al. |
| 2004/0225360 A1 | 11/2004 | Malone |
| 2004/0230305 A1 | 11/2004 | Gorensek et al. |
| 2004/0260286 A1 | 12/2004 | Ferree |
| 2004/0267369 A1 | 12/2004 | Lyons et al. |
| 2005/0015059 A1 | 1/2005 | Sweeney |
| 2005/0015146 A1 | 1/2005 | Louis et al. |
| 2005/0033435 A1 | 2/2005 | Belliard et al. |
| 2005/0049590 A1 | 3/2005 | Alleyne et al. |
| 2005/0055023 A1 | 3/2005 | Sohngen et al. |
| 2005/0075641 A1 | 4/2005 | Singhatat et al. |
| 2005/0080415 A1 | 4/2005 | Keyer et al. |
| 2005/0107878 A1 | 5/2005 | Conchy |
| 2005/0112397 A1 | 5/2005 | Rolfe et al. |
| 2005/0124993 A1 | 6/2005 | Chappuis |
| 2005/0131409 A1 | 6/2005 | Chervitz et al. |
| 2005/0137605 A1 | 6/2005 | Assell et al. |
| 2005/0143837 A1 | 6/2005 | Ferree |
| 2005/0149192 A1 | 7/2005 | Zucherman et al. |
| 2005/0159749 A1 | 7/2005 | Levy et al. |
| 2005/0165398 A1 | 7/2005 | Reiley |
| 2005/0192572 A1 | 9/2005 | Abdelgany et al. |
| 2005/0228384 A1 | 10/2005 | Zucherman et al. |
| 2005/0246021 A1 | 11/2005 | Ringeisen et al. |
| 2005/0251146 A1 | 11/2005 | Martz et al. |
| 2005/0273101 A1 | 12/2005 | Schumacher |
| 2005/0277940 A1 | 12/2005 | Neff |
| 2006/0036247 A1 | 2/2006 | Michelson |
| 2006/0036251 A1 | 2/2006 | Reiley |
| 2006/0036252 A1 | 2/2006 | Baynham et al. |
| 2006/0054171 A1 | 3/2006 | Dall |
| 2006/0058793 A1 | 3/2006 | Michelson |
| 2006/0058800 A1 | 3/2006 | Ainsworth et al. |
| 2006/0062825 A1 | 3/2006 | Maccecchini |
| 2006/0084986 A1 | 4/2006 | Grinberg et al. |
| 2006/0089656 A1 | 4/2006 | Allard et al. |
| 2006/0111779 A1 | 5/2006 | Petersen |
| 2006/0129247 A1 | 6/2006 | Brown et al. |
| 2006/0142772 A1 | 6/2006 | Ralph et al. |
| 2006/0161163 A1 | 7/2006 | Shino |
| 2006/0178673 A1 | 8/2006 | Curran |
| 2006/0195094 A1 | 8/2006 | McGraw et al. |
| 2006/0217717 A1 | 9/2006 | Whipple |
| 2006/0241776 A1 | 10/2006 | Brown et al. |
| 2006/0271054 A1 | 11/2006 | Sucec et al. |
| 2006/0293662 A1 | 12/2006 | Boyer, II et al. |
| 2007/0027544 A1 | 2/2007 | McCord et al. |
| 2007/0038219 A1 | 2/2007 | Matthis et al. |
| 2007/0049933 A1 | 3/2007 | Ahn et al. |
| 2007/0066977 A1 | 3/2007 | Assell et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0093898 A1 | 4/2007 | Schwab et al. |
| 2007/0106383 A1 | 5/2007 | Abdou |
| 2007/0149976 A1 | 6/2007 | Hale et al. |
| 2007/0156144 A1 | 7/2007 | Ulrich et al. |
| 2007/0156241 A1 | 7/2007 | Reiley et al. |
| 2007/0156246 A1 | 7/2007 | Meswania et al. |
| 2007/0161989 A1 | 7/2007 | Heinz et al. |
| 2007/0173820 A1 | 7/2007 | Trieu |
| 2007/0219634 A1 | 9/2007 | Greenhalgh et al. |
| 2007/0233080 A1 | 10/2007 | Na et al. |
| 2007/0233146 A1 | 10/2007 | Henniges et al. |
| 2007/0233247 A1 | 10/2007 | Schwab |
| 2007/0250166 A1 | 10/2007 | McKay |
| 2007/0270879 A1 | 11/2007 | Isaza et al. |
| 2007/0282443 A1 | 12/2007 | Globerman et al. |
| 2008/0009861 A1* | 1/2008 | Stark .................... A61B 17/68 606/914 |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0021480 A1 | 1/2008 | Chin et al. |
| 2008/0065093 A1 | 3/2008 | Assell et al. |
| 2008/0065215 A1 | 3/2008 | Reiley |
| 2008/0071356 A1 | 3/2008 | Greenhalgh et al. |
| 2008/0109083 A1 | 5/2008 | Van Hoeck et al. |
| 2008/0132901 A1 | 6/2008 | Recoules-Arche et al. |
| 2008/0140082 A1 | 6/2008 | Erdem et al. |
| 2008/0147079 A1 | 6/2008 | Chin et al. |
| 2008/0154374 A1 | 6/2008 | Labrom |
| 2008/0161810 A1 | 7/2008 | Melkent |
| 2008/0183204 A1 | 7/2008 | Greenhalgh et al. |
| 2008/0234758 A1 | 9/2008 | Fisher et al. |
| 2008/0255562 A1 | 10/2008 | Gil et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0294202 A1 | 11/2008 | Peterson et al. |
| 2008/0306554 A1 | 12/2008 | McKinley |
| 2009/0012529 A1 | 1/2009 | Blain et al. |
| 2009/0018660 A1 | 1/2009 | Roush |
| 2009/0024174 A1 | 1/2009 | Stark |
| 2009/0036927 A1 | 2/2009 | Vestgaarden |
| 2009/0037148 A1 | 2/2009 | Lin et al. |
| 2009/0043393 A1 | 2/2009 | Duggal et al. |
| 2009/0082810 A1 | 3/2009 | Bhatnagar et al. |
| 2009/0082869 A1 | 3/2009 | Slemker et al. |
| 2009/0099602 A1 | 4/2009 | Aflatoon |
| 2009/0099610 A1 | 4/2009 | Johnson et al. |
| 2009/0105770 A1 | 4/2009 | Berrevooets et al. |
| 2009/0118771 A1 | 5/2009 | Gonzalez-Hernandez |

(56) References Cited

U.S. PATENT DOCUMENTS

| | | |
|---|---|---|
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0187247 A1 | 7/2009 | Metcalf, Jr. et al. |
| 2009/0216238 A1 | 8/2009 | Stark |
| 2009/0270929 A1 | 10/2009 | Suddaby |
| 2009/0287254 A1 | 11/2009 | Nayet et al. |
| 2009/0312798 A1 | 12/2009 | Varela |
| 2009/0324678 A1 | 12/2009 | Thorne et al. |
| 2010/0003638 A1 | 1/2010 | Collins et al. |
| 2010/0022535 A1 | 1/2010 | Lee et al. |
| 2010/0076502 A1 | 3/2010 | Guyer et al. |
| 2010/0081107 A1 | 4/2010 | Bagambisa et al. |
| 2010/0094290 A1 | 4/2010 | Vaidya |
| 2010/0094295 A1 | 4/2010 | Schnieders et al. |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0131011 A1 | 5/2010 | Stark |
| 2010/0137990 A1 | 6/2010 | Apatsidis et al. |
| 2010/0145461 A1 | 6/2010 | Landry et al. |
| 2010/0160977 A1 | 6/2010 | Gephart et al. |
| 2010/0168798 A1 | 7/2010 | Clineff et al. |
| 2010/0191292 A1 | 7/2010 | DeMeo et al. |
| 2010/0268228 A1 | 10/2010 | Petersen |
| 2010/0280619 A1 | 11/2010 | Yuan et al. |
| 2010/0280622 A1 | 11/2010 | McKinley |
| 2010/0286778 A1 | 11/2010 | Eisermann et al. |
| 2010/0331851 A1 | 12/2010 | Huene |
| 2010/0331893 A1 | 12/2010 | Geist et al. |
| 2011/0009869 A1 | 1/2011 | Marino et al. |
| 2011/0022089 A1 | 1/2011 | Assell et al. |
| 2011/0029019 A1 | 2/2011 | Ainsworth et al. |
| 2011/0040362 A1 | 2/2011 | Godara et al. |
| 2011/0046737 A1 | 2/2011 | Teisen |
| 2011/0060373 A1 | 3/2011 | Russell et al. |
| 2011/0060375 A1 | 3/2011 | Bonutti |
| 2011/0066190 A1 | 3/2011 | Schaller et al. |
| 2011/0082551 A1 | 4/2011 | Kraus |
| 2011/0093020 A1 | 4/2011 | Wu |
| 2011/0098747 A1 | 4/2011 | Donner et al. |
| 2011/0098816 A1 | 4/2011 | Jacob et al. |
| 2011/0098817 A1 | 4/2011 | Eckhardt et al. |
| 2011/0106175 A1 | 5/2011 | Rezach |
| 2011/0125268 A1* | 5/2011 | Reiley ............... A61B 17/1615 623/17.11 |
| 2011/0153018 A1 | 6/2011 | Walters et al. |
| 2011/0160866 A1 | 6/2011 | Laurence et al. |
| 2011/0178561 A1 | 7/2011 | Roh |
| 2011/0184518 A1 | 7/2011 | Trieu |
| 2011/0184519 A1 | 7/2011 | Trieu |
| 2011/0184520 A1 | 7/2011 | Trieu |
| 2011/0196372 A1 | 8/2011 | Murase |
| 2011/0230966 A1 | 9/2011 | Trieu |
| 2011/0238074 A1 | 9/2011 | Ek |
| 2011/0238181 A1 | 9/2011 | Trieu |
| 2011/0245930 A1 | 10/2011 | Alley et al. |
| 2011/0257755 A1 | 10/2011 | Bellemere et al. |
| 2011/0264229 A1 | 10/2011 | Donner |
| 2011/0276098 A1 | 11/2011 | Biedermann et al. |
| 2011/0295272 A1 | 12/2011 | Assell et al. |
| 2011/0295370 A1 | 12/2011 | Suh et al. |
| 2011/0313471 A1 | 12/2011 | McLean et al. |
| 2011/0313532 A1 | 12/2011 | Hunt |
| 2011/0319995 A1 | 12/2011 | Voellmicke et al. |
| 2012/0004730 A1 | 1/2012 | Castro |
| 2012/0083887 A1 | 4/2012 | Purcell et al. |
| 2012/0095560 A1 | 4/2012 | Donner |
| 2012/0179256 A1 | 7/2012 | Reiley |
| 2012/0191191 A1* | 7/2012 | Trieu ............... A61B 17/683 623/17.11 |
| 2012/0226318 A1 | 9/2012 | Wenger et al. |
| 2012/0253398 A1 | 10/2012 | Metcalf et al. |
| 2012/0259372 A1 | 10/2012 | Glazer et al. |
| 2012/0271424 A1 | 10/2012 | Crawford |
| 2012/0277866 A1 | 11/2012 | Kalluri et al. |
| 2012/0296428 A1 | 11/2012 | Donner |
| 2012/0323285 A1 | 12/2012 | Assell et al. |
| 2013/0018427 A1 | 1/2013 | Pham et al. |
| 2013/0030456 A1* | 1/2013 | Assell ............... A61B 17/1617 606/170 |
| 2013/0030529 A1 | 1/2013 | Hunt |
| 2013/0035727 A1 | 2/2013 | Datta |
| 2013/0053852 A1 | 2/2013 | Greenhalgh et al. |
| 2013/0053854 A1 | 2/2013 | Schoenefeld et al. |
| 2013/0053902 A1 | 2/2013 | Trudeau |
| 2013/0053963 A1 | 2/2013 | Davenport |
| 2013/0072984 A1 | 3/2013 | Robinson |
| 2013/0085535 A1 | 4/2013 | Greenhalgh et al. |
| 2013/0096683 A1 | 4/2013 | Kube |
| 2013/0116793 A1 | 5/2013 | Kloss |
| 2013/0123850 A1 | 5/2013 | Schoenefeld et al. |
| 2013/0123935 A1 | 5/2013 | Hunt et al. |
| 2013/0131678 A1 | 5/2013 | Dahners |
| 2013/0144343 A1 | 6/2013 | Arnett et al. |
| 2013/0158609 A1 | 6/2013 | Mikhail et al. |
| 2013/0172736 A1* | 7/2013 | Abdou ............... A61B 17/70 600/425 |
| 2013/0197590 A1 | 8/2013 | Assell et al. |
| 2013/0203088 A1 | 8/2013 | Baerlecken et al. |
| 2013/0218215 A1 | 8/2013 | Ginn et al. |
| 2013/0218282 A1 | 8/2013 | Hunt |
| 2013/0231746 A1 | 9/2013 | Ginn et al. |
| 2013/0237988 A1 | 9/2013 | Mauldin |
| 2013/0245703 A1 | 9/2013 | Warren et al. |
| 2013/0245763 A1 | 9/2013 | Mauldin |
| 2013/0267836 A1 | 10/2013 | Mauldin et al. |
| 2013/0267961 A1 | 10/2013 | Mauldin et al. |
| 2013/0267989 A1 | 10/2013 | Mauldin et al. |
| 2013/0274890 A1 | 10/2013 | McKay |
| 2013/0296953 A1 | 11/2013 | Mauldin et al. |
| 2013/0325129 A1 | 12/2013 | Huang |
| 2014/0012334 A1 | 1/2014 | Armstrong et al. |
| 2014/0012340 A1 | 1/2014 | Beck et al. |
| 2014/0031934 A1 | 1/2014 | Trieu |
| 2014/0031935 A1 | 1/2014 | Donner et al. |
| 2014/0031938 A1 | 1/2014 | Lechmann et al. |
| 2014/0031939 A1 | 1/2014 | Wolfe et al. |
| 2014/0046380 A1 | 2/2014 | Asfora |
| 2014/0074175 A1 | 3/2014 | Ehler et al. |
| 2014/0088596 A1 | 3/2014 | Assell et al. |
| 2014/0088707 A1 | 3/2014 | Donner et al. |
| 2014/0121776 A1 | 5/2014 | Hunt |
| 2014/0135927 A1 | 5/2014 | Pavlov et al. |
| 2014/0142700 A1 | 5/2014 | Donner et al. |
| 2014/0172027 A1 | 6/2014 | Biedermann et al. |
| 2014/0200618 A1 | 7/2014 | Donner et al. |
| 2014/0207240 A1 | 7/2014 | Stoffman et al. |
| 2014/0257294 A1 | 9/2014 | Gedet et al. |
| 2014/0257408 A1 | 9/2014 | Trieu et al. |
| 2014/0276846 A1 | 9/2014 | Mauldin et al. |
| 2014/0276851 A1 | 9/2014 | Schneider et al. |
| 2014/0277139 A1 | 9/2014 | Vrionis et al. |
| 2014/0277165 A1 | 9/2014 | Katzman et al. |
| 2014/0277460 A1 | 9/2014 | Schifano et al. |
| 2014/0277462 A1 | 9/2014 | Yerby et al. |
| 2014/0277463 A1 | 9/2014 | Yerby et al. |
| 2014/0288605 A1 | 9/2014 | Mesiwala et al. |
| 2014/0288649 A1 | 9/2014 | Hunt |
| 2014/0288650 A1 | 9/2014 | Hunt |
| 2014/0296982 A1 | 10/2014 | Cheng |
| 2014/0330382 A1 | 11/2014 | Mauldin |
| 2014/0364917 A1 | 12/2014 | Sandstrom et al. |
| 2015/0012051 A1 | 1/2015 | Warren et al. |
| 2015/0039037 A1 | 2/2015 | Donner et al. |
| 2015/0080951 A1 | 3/2015 | Yeh |
| 2015/0080972 A1 | 3/2015 | Chin et al. |
| 2015/0094765 A1 | 4/2015 | Donner et al. |
| 2015/0112444 A1 | 4/2015 | Aksu |
| 2015/0147397 A1 | 5/2015 | Altschuler |
| 2015/0150683 A1 | 6/2015 | Donner et al. |
| 2015/0173805 A1 | 6/2015 | Donner et al. |

(56) References Cited

U.S. PATENT DOCUMENTS

| | | |
|---|---|---|
| 2015/0173904 A1 | 6/2015 | Stark |
| 2015/0182268 A1 | 7/2015 | Donner et al. |
| 2015/0190149 A1 | 7/2015 | Assell et al. |
| 2015/0190187 A1 | 7/2015 | Parent et al. |
| 2015/0216566 A1 | 8/2015 | Mikhail et al. |
| 2015/0238203 A1 | 8/2015 | Asfora |
| 2015/0250513 A1 | 9/2015 | De Lavigne Sainte |
| 2015/0250595 A1 | 9/2015 | Mauldin et al. |
| 2015/0250611 A1 | 9/2015 | Schifano et al. |
| 2015/0250612 A1 | 9/2015 | Schifano et al. |
| 2015/0257892 A1 | 9/2015 | Lechmann et al. |
| 2015/0313720 A1 | 11/2015 | Lorio |
| 2015/0320450 A1 | 11/2015 | Mootien et al. |
| 2015/0320451 A1 | 11/2015 | Mootien et al. |
| 2015/0320469 A1 | 11/2015 | Biedermann et al. |
| 2015/0342753 A1 | 12/2015 | Donner et al. |
| 2016/0000488 A1 | 1/2016 | Cross, III |
| 2016/0022429 A1 | 1/2016 | Greenhalgh et al. |
| 2016/0081810 A1 | 3/2016 | Reiley et al. |
| 2016/0095711 A1 | 4/2016 | Castro |
| 2016/0095721 A1 | 4/2016 | Schell et al. |
| 2016/0100870 A1 | 4/2016 | Lavigne et al. |
| 2016/0106477 A1 | 4/2016 | Hynes et al. |
| 2016/0106479 A1 | 4/2016 | Hynes et al. |
| 2016/0120661 A1 | 5/2016 | Schell et al. |
| 2016/0143671 A1 | 5/2016 | Jimenez |
| 2016/0175113 A1 | 6/2016 | Lins |
| 2016/0184103 A1 | 6/2016 | Fonte et al. |
| 2016/0213487 A1 | 7/2016 | Wilson et al. |
| 2016/0242820 A1 | 8/2016 | Whipple et al. |
| 2016/0242912 A1 | 8/2016 | Lindsey et al. |
| 2016/0249940 A1 | 9/2016 | Stark |
| 2016/0287171 A1 | 10/2016 | Sand et al. |
| 2016/0287301 A1 | 10/2016 | Mehl et al. |
| 2016/0302941 A1 | 10/2016 | Reiley et al. |
| 2016/0310188 A1 | 10/2016 | Marino et al. |
| 2016/0310197 A1 | 10/2016 | Black et al. |
| 2016/0324643 A1 | 11/2016 | Donner et al. |
| 2016/0324656 A1 | 11/2016 | Morris et al. |
| 2016/0374727 A1 | 12/2016 | Greenhalgh et al. |
| 2017/0007409 A1 | 1/2017 | Mauldin et al. |
| 2017/0014235 A1 | 1/2017 | Jones et al. |
| 2017/0020573 A1 | 1/2017 | Cain et al. |
| 2017/0020585 A1 | 1/2017 | Harshman et al. |
| 2017/0049488 A1 | 2/2017 | Vestgaarden |
| 2017/0086885 A1 | 3/2017 | Duncan et al. |
| 2017/0128083 A1 | 5/2017 | Germain |
| 2017/0128214 A1 | 5/2017 | Mayer |
| 2017/0135733 A1 | 5/2017 | Donner et al. |
| 2017/0143513 A1 | 5/2017 | Sandstrom et al. |
| 2017/0156879 A1 | 6/2017 | Janowski |
| 2017/0156880 A1 | 6/2017 | Halverson et al. |
| 2017/0181770 A1 | 6/2017 | Reiley et al. |
| 2017/0202511 A1 | 7/2017 | Chang et al. |
| 2017/0209155 A1 | 7/2017 | Petersen |
| 2017/0216036 A1 | 8/2017 | Cordaro |
| 2017/0224393 A1 | 8/2017 | Lavigne et al. |
| 2017/0246000 A1 | 8/2017 | Pavlov et al. |
| 2017/0258498 A1 | 9/2017 | Redmond et al. |
| 2017/0258506 A1 | 9/2017 | Redmond et al. |
| 2017/0258606 A1 | 9/2017 | Afzal |
| 2017/0273729 A1 | 9/2017 | Reiley |
| 2017/0296244 A1 | 10/2017 | Schneider et al. |
| 2017/0296344 A1 | 10/2017 | Souza et al. |
| 2017/0303938 A1 | 10/2017 | Rindal et al. |
| 2017/0333205 A1 | 11/2017 | Joly et al. |
| 2018/0104063 A1 | 4/2018 | Asaad |
| 2018/0104068 A1 | 4/2018 | Sack |
| 2018/0110624 A1 | 4/2018 | Arnone |
| 2018/0110626 A1 | 4/2018 | McShane, III et al. |
| 2018/0200063 A1 | 7/2018 | Kahmer et al. |
| 2018/0214192 A1 | 8/2018 | Roby et al. |
| 2018/0228613 A1 | 8/2018 | Jones et al. |
| 2018/0228617 A1 | 8/2018 | Srour et al. |
| 2018/0228621 A1 | 8/2018 | Reiley et al. |
| 2018/0243097 A1 | 8/2018 | Jones et al. |
| 2018/0256351 A1 | 9/2018 | Bishop et al. |
| 2018/0256352 A1 | 9/2018 | Nyahay et al. |
| 2018/0256361 A1 | 9/2018 | Bishop et al. |
| 2018/0280139 A1 | 10/2018 | Jones et al. |
| 2018/0280140 A1 | 10/2018 | Jones et al. |
| 2018/0296363 A1 | 10/2018 | Berry |
| 2018/0303623 A1 | 10/2018 | Shoshtaev |
| 2018/0303624 A1 | 10/2018 | Shoshtaev |
| 2018/0368894 A1 | 12/2018 | Wieland et al. |
| 2019/0000636 A1 | 1/2019 | Kim et al. |
| 2019/0008562 A1 | 1/2019 | Melton et al. |
| 2019/0076258 A1 | 3/2019 | Black et al. |
| 2019/0076266 A1 | 3/2019 | Trudeau et al. |
| 2019/0083270 A1 | 3/2019 | Milz et al. |
| 2019/0091027 A1 | 3/2019 | Asaad et al. |
| 2019/0125408 A1 | 5/2019 | Asfora et al. |
| 2019/0133769 A1 | 5/2019 | Tetsworth et al. |
| 2019/0133783 A1 | 5/2019 | Unger et al. |
| 2019/0142606 A1 | 5/2019 | Freudenberger |
| 2019/0151113 A1 | 5/2019 | Sack |
| 2019/0151114 A1 | 5/2019 | Sack |
| 2019/0159818 A1 | 5/2019 | Schneider et al. |
| 2019/0159901 A1 | 5/2019 | Mauldin et al. |
| 2019/0183653 A1 | 6/2019 | Gregersen et al. |
| 2019/0254840 A1 | 8/2019 | Gray et al. |
| 2019/0262049 A1 | 8/2019 | Tempco et al. |
| 2019/0298542 A1 | 10/2019 | Kloss |
| 2019/0343640 A1 | 11/2019 | Donner et al. |
| 2019/0343641 A1 | 11/2019 | Mauldin et al. |
| 2019/0343653 A1 | 11/2019 | McKay |
| 2020/0000595 A1 | 1/2020 | Jones et al. |
| 2020/0008817 A1 | 1/2020 | Reiley et al. |
| 2020/0008850 A1 | 1/2020 | Mauldin et al. |
| 2020/0246158 A1 | 8/2020 | Bergey |
| 2020/0345507 A1 | 11/2020 | Reiley |
| 2020/0345508 A1 | 11/2020 | Reiley |
| 2020/0345509 A1 | 11/2020 | Reiley |
| 2020/0345510 A1 | 11/2020 | Reiley |

FOREIGN PATENT DOCUMENTS

| | | |
|---|---|---|
| CN | 1909848 A | 2/2007 |
| CN | 101795632 A | 8/2010 |
| CN | 102361601 A | 2/2012 |
| EP | 1287796 A1 | 3/2003 |
| JP | 59200642 A | 11/1984 |
| JP | 05-176942 A | 7/1993 |
| JP | 05184615 A | 7/1993 |
| JP | 09149906 A | 10/1997 |
| JP | 10-85231 A | 4/1998 |
| JP | 11318931 A | 11/1999 |
| JP | 2002509753 A | 4/2002 |
| JP | 2003511198 A | 3/2003 |
| JP | 2003533329 A | 11/2003 |
| JP | 2003534046 A | 11/2003 |
| JP | 2004121841 | 4/2004 |
| JP | 2004512895 | 4/2004 |
| JP | 2004516866 | 6/2004 |
| JP | 2006506181 | 2/2006 |
| JP | 2007535973 A | 12/2007 |
| JP | 2008540036 A | 11/2008 |
| JP | 2009521990 A | 6/2009 |
| JP | 2009533159 A | 9/2009 |
| JP | 2010137016 A | 6/2010 |
| JP | 2015510506 A | 4/2015 |
| WO | WO97/31517 A2 | 8/1997 |
| WO | WO 01/17445 A1 | 3/2001 |
| WO | WO02/38054 | 5/2002 |
| WO | WO03/007839 A2 | 1/2003 |
| WO | WO04/02344 | 1/2004 |
| WO | WO2004/043277 A1 | 5/2004 |
| WO | WO2005/009729 A2 | 2/2005 |
| WO | WO2006/003316 | 1/2006 |
| WO | WO2006/023793 A2 | 3/2006 |
| WO | WO20061074321 A2 | 7/2006 |
| WO | WO2009/029074 A1 | 3/2009 |
| WO | WO2010/105196 A1 | 9/2010 |
| WO | WO2011010463 A1 | 1/2011 |

(56) References Cited

FOREIGN PATENT DOCUMENTS

| WO | WO2011/110865 A2 | 9/2011 |
|---|---|---|
| WO | WO2011/124874 A1 | 10/2011 |
| WO | WO2011/149557 A1 | 12/2011 |
| WO | WO2013/000071 A1 | 1/2013 |
| WO | WO2013/119907 A1 | 8/2013 |

OTHER PUBLICATIONS

Mesiwala et al.; U.S. Appl. No. 15/903,410 entitled "Implants for spinal fixation or fusion," filed Feb. 23, 2018.
Reiley et al.; U.S. Appl. No. 16/237,409 entitled "Implants for bone fixation or fusion," filed Dec. 31, 2018.
Mesiwala et al.; U.S. Appl. No. 16/276,430 entitled "Implants for spinal fixation and or fusion," filed Feb. 14, 2019.
Lindsey et al.; U.S. Appl. No. 16/368,686 entitled "Threaded implants and methods of use across bone segments," filed Mar. 28, 2019.
Mesiwala et al.; U.S. Appl. No. 16/874,149 entitled "Implants for spinal fixation and or fusion," filed May 14, 2020.
Reckling et al.; U.S. Appl. No. 17/116,903 entitled "Sacro-iliac joint stabilizing implants and methods of implantation," filed Dec. 9, 2020.
Mesiwala et al.; U.S. Appl. No. 17/217,794 entitled "Implants for spinal fizxation or fusion," filed Mar. 20, 2021.
Stuart et al.; U.S. Appl. No. 17/104,753 entitled "Bone stabilizing implants and methods of placement across SI joints," filed Nov. 25, 2020.

* cited by examiner

FIG. 4A  Lateral View

FIG. 4B  Inlet View

FIG. 4C  Outlet View

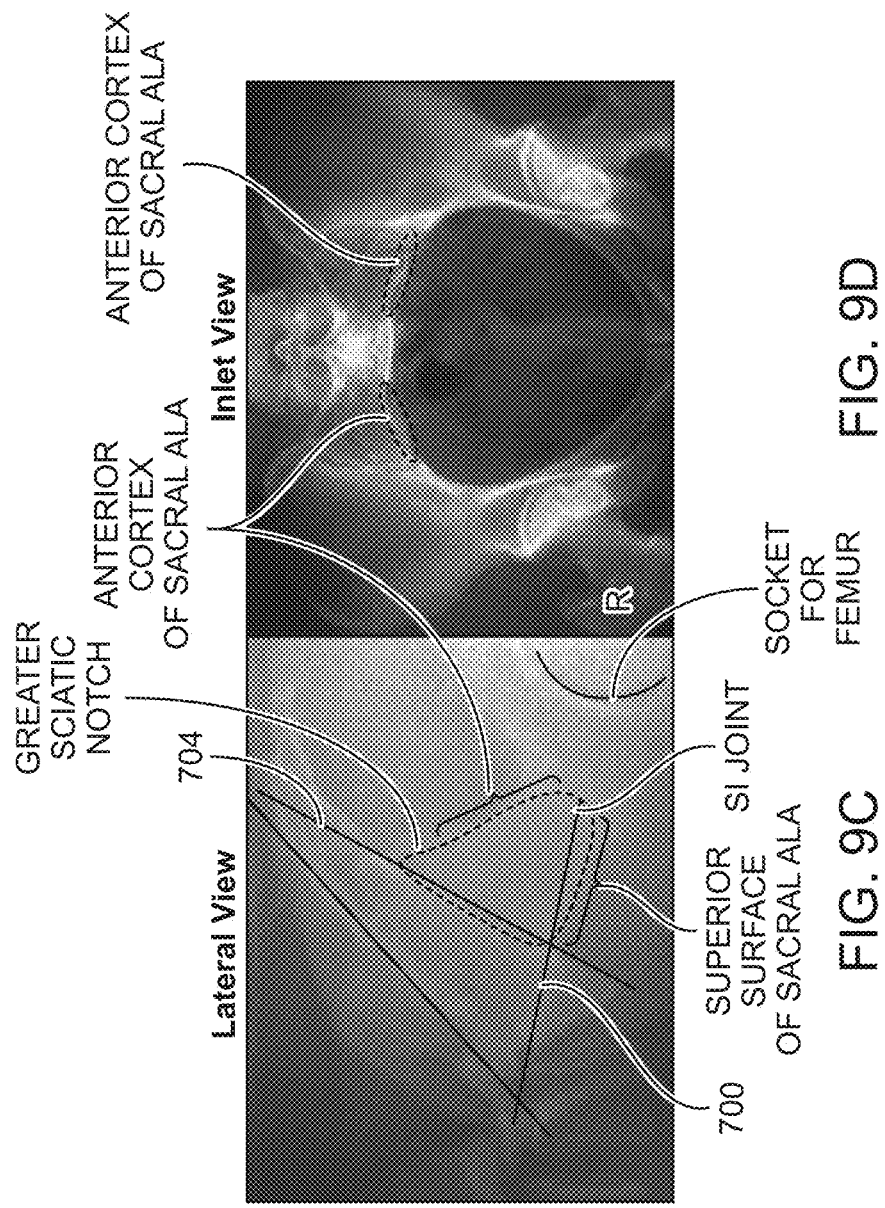

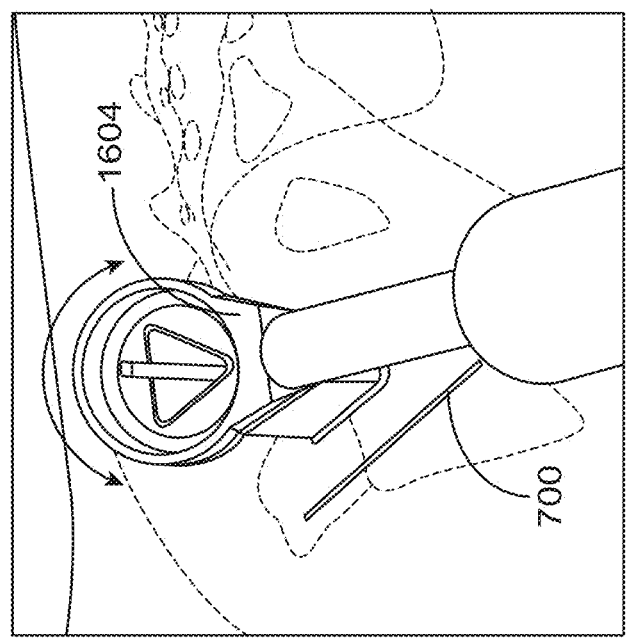
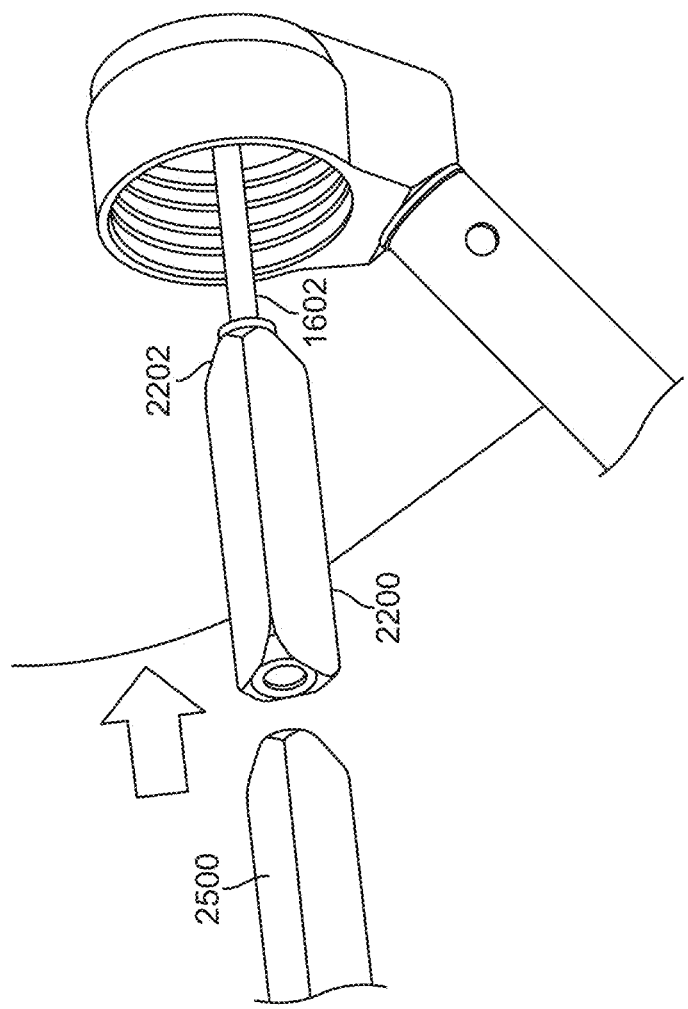
FIG. 25B
FIG. 25A

IMPLANT PLACEMENT

CROSS REFERENCE TO RELATED APPLICATIONS

This application is a continuation-in-part of U.S. application Ser. No. 14/515,416, filed Oct. 15, 2014, now U.S. Pat. No. 9,839,448, which claims priority to U.S. Provisional Patent Application No. 61/891,326, filed Oct. 15, 2013, and titled "IMPLANT PLACEMENT," which is herein incorporated by reference in its entirety for all purposes.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the invention relate generally to implant placement into bone. More specifically, embodiments of the invention relate to implant placement across the sacro-iliac joint.

BACKGROUND

Many types of hardware are available both for the fixation of bones that are fractured and for the fixation of bones that are to be fused (arthrodesed).

For example, the human pelvic girdle (see FIGS. 1 and 2) is made up of three large bones joined together by three relatively immobile joints. One of the bones is called the sacrum and it lies at the bottom of the lumbar spine, where it connects with the L5 vertebra. The other two bones are commonly called "pelvic bones" and are technically referred to as the right ilium and—the left ilium. The sacrum connects with both pelvic bones at the sacroiliac joint (in shorthand, the SI-Joint).

The SI-Joint functions to transfer forces from the spine to the lower extremities, and vice-versa. The SI-Joint has been identified as the pain generator in up to 22% of patients who present with lower back pain.

Sacroiliac joint fusion is a surgical procedure that is performed to alleviate pain coming from the SI joint in patients who have failed to receive adequate pain relief with non-surgical treatments of the SI joint. Some conditions of the SI joint that may be treated with SI joint fusion (arthrodesis) are: degenerative sacroiliitis, inflammatory sacroiliitis, iatrogenic instability of the sacroiliac joint, osteitis condensans ilii, or traumatic fracture dislocation of the pelvis. Currently, screws and screws with plates are used as the standard instrumentation for sacro-iliac fusion. Historically, an SI joint fusion consisted of an open surgical approach to the SI joint from an anterior, a posterior, or a lateral direction. The surgeon would then debride (remove) the cartilage from the articular portion of the joint and the interosseous ligament from the fibrous portion of the joint. These open approaches require a large incision and deep soft tissue dissection to approach the damaged, subluxed, dislocated, fractured, or degenerative SI joint.

A typical technique for placing implants involves placement of one or multiple implants from a lateral to medial direction across the SI-Joint. These implants are placed with a starting point on the lateral aspect of the ilium. The implants are then directed across the ilium, across the sacroiliac joint and into the sacrum. Regarding implant position, care is taken to avoid impinging on neural and vascular structures, including neural tissue within the neural foraminae or spinal canal. In addition, care must be taken to place the implants across the SI joint and avoid the leading tip(s) of the implant(s) violating the osseous envelope of the sacrum. However, the density of the bone in different portions of the sacrum is not typically a consideration during implant placement.

Accordingly, it would be desirable to provide systems and methods for placing multiple implants across the SI-Joint into those portions of the sacrum with relatively higher bone density. Implants placed into denser (stronger) bone will demonstrate improved short-term and long-term mechanical stability of the implant construct spanning the SI-Joint post implantation.

SUMMARY OF THE DISCLOSURE

The present invention relates generally to implant placement into bone. More specifically, embodiments of the invention relate to implant placement across the sacro-iliac joint.

In some embodiments, a method of implanting a plurality of implants in the SI-joint is provided. The method can include inserting a plurality of guide pins into an anterior portion of the SI-joint that is associated with articular cartilage; creating a bore around each of the plurality of guide pins; and inserting an implant into each bore such that each implant is located in an anterior portion of the SI-joint that is associated with articular cartilage.

In some embodiments, the method further includes obtaining a lateral view of the pelvis; and identifying a plurality of anatomical landmarks in the lateral view including the alar line, the posterior sacral body line, the anterior sacral body line, and the anterior cortex of the sacral alar, wherein the plurality of guide pins are inserted with reference to at least one anatomical landmark.

In some embodiments, at least one guide pin and implant are inserted anterior of the anterior sacral body line in the lateral view.

In some embodiments, at least two guide pins and implants are inserted anterior of the anterior sacral body line in the lateral view.

In some embodiments, the at least one guide pin and implant that is inserted anterior of the anterior sacral body line in the lateral view is angled with respect to the horizontal axis in the inlet view.

In some embodiments, at least two guide pins and two implants are placed parallel to the alar line.

In some embodiments, the plurality of guide pins are parallel in the outlet view.

In some embodiments, the method further includes identifying a target for the plurality of guide pins in the inlet view, wherein the target is located in the middle of the sacral body.

In some embodiments, the method further includes advancing the guide pins towards the target in the inlet view.

In some embodiments, the implants are non-colinear in the lateral view.

In some embodiments, the implants have an elongate body with a longitudinal axis and a rectilinear cross-sectional profile transverse to the longitudinal axis.

In some embodiments, the implants are screws.

In some embodiments, a system for fixation of the SI-joint is provided. The system can include a first elongate implant that is inserted into the SI-joint through a cephalad portion of the articular cartilage in the SI-joint; a second elongate implant that is inserted into the SI-joint through a middle portion of the articular cartilage in the SI-joint, wherein the second elongate implant is caudal and anterior to the first elongate implant; and a third elongate implant that is inserted into the SI-joint through a caudal portion of the articular cartilage in the SI-joint, wherein the third elongate implant in caudal to the second elongate implant.

In some embodiments, the first elongate implant is inserted into the SI-joint caudal to the alar line and between the posterior sacral body line and the anterior sacral body line in a lateral view.

In some embodiments, the second elongate implant is inserted into the SI-joint caudal to the alar line and anterior to the anterior sacral body line in a lateral view.

In some embodiments, the third elongate implant is inserted into the SI-joint anterior to the anterior sacral body line in a lateral view.

In some embodiments, the first elongate implant is positioned horizontally in an inlet view and the second elongate implant is angled with respect to the first elongate implant in the inlet view.

In some embodiments, the first elongate implant, the second elongate implant, and the third elongate implant each have an elongate body with a longitudinal axis and a rectilinear cross-sectional profile transverse to the longitudinal axis.

In some embodiments, the first elongate implant, the second elongate implant, and the third elongate implant each are screws.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 9C and 9D illustrate a lateral view and an inlet view that shows that the anterior cortex of the sacral ala is visible as the most anterior aspects of the sacrum.

FIGS. 25A and 25B illustrate implant insertion over the guide pin.

DETAILED DESCRIPTION

Pre-op Preparation and Patient Setup

Figure 1:
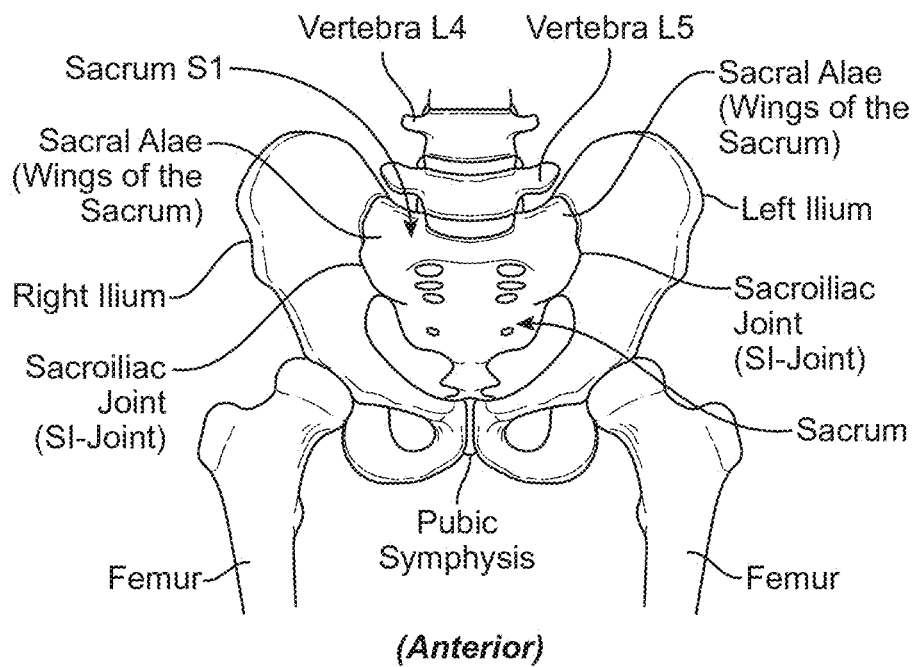
FIGS. 1 and 2 illustrate anterior and posterior views of the pelvic girdle.
Figure 2:
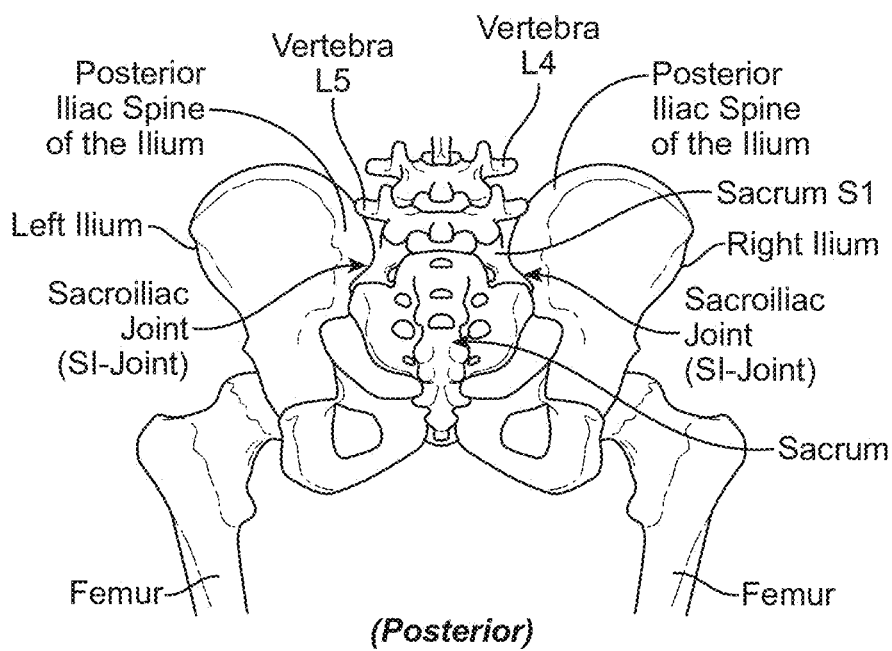
Figure 3:
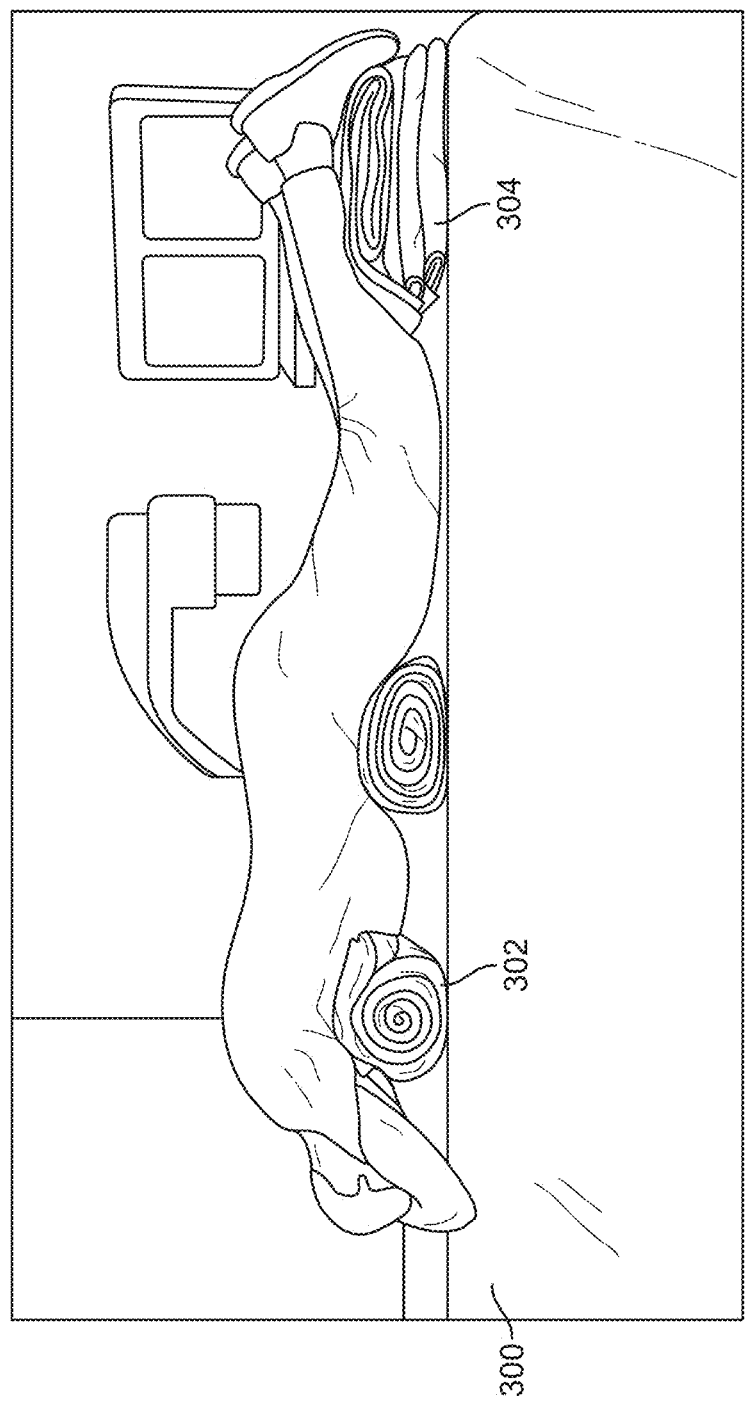
FIG. 3 illustrates the position of a patient on a Jackson table for CT imaging of the pelvic girdle.

A computed tomography (CT) scan may be taken of the pelvis and SI-Joints prior to surgery to check for anatomic anomalies and to identify osseous landmarks useful for implant placement. The patient may be placed on a flat radiolucent table, such as a Jackson table, to facilitate intra-operative imaging. Although one C-arm is typically employed, some surgeons may employ two C-arms, with one C-arm set in the lateral position and the other C-arm rotatable between the inlet and outlet positions, as further described below. As illustrated in FIG. 3, the patient may be placed on a flat Jackson type imaging table 300 with towel rolls 302 or other support structures placed transversely under the patient's chest and waist. This position allows the abdomen to hang free resulting in diminished intraabdominal pressure. Pillows 304 or other support structures can be placed under the patient's feet to relax the knees. After the patient has been properly positioned, a lateral view, an inlet view, and an outlet view may be taken of the SI-Joint and pelvis. The surgeon may identify any abnormalities that could interfere with the procedure and may also confirm that the anatomical landmarks used to guide implant placement are visible.

Intraoperative Imaging

Figure 4:
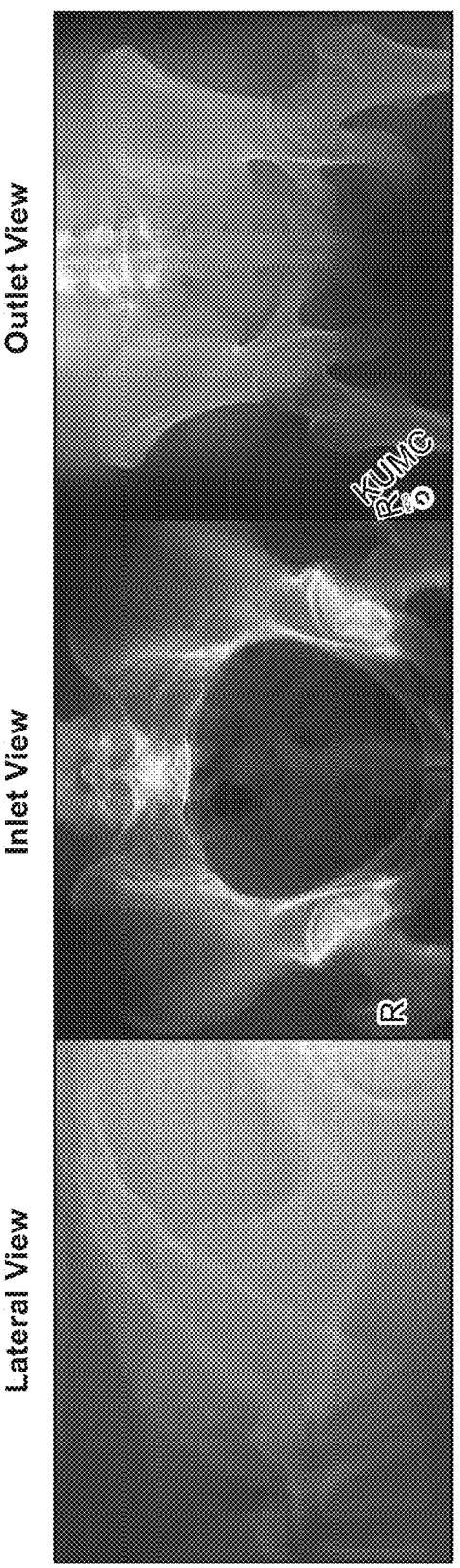
FIGS. 4A-4C are three imaging views of the pelvis, a lateral view of the sacrum shown in FIG. 4A, an inlet view of the pelvis shown in FIG. 4B, and an outlet view of the pelvis shown in FIG. 4C.

As illustrated in FIGS. 4A-4C, three imaging views, a lateral view of the sacrum shown in FIG. 4A, an inlet view of the pelvis shown in FIG. 4B, and an outlet view of the pelvis shown in FIG. 4C, may be used to facilitate safe insertion and placement of instruments, tools and implants during the procedure. These fluoroscopic views allow the surgeon to identify various anatomical structures and landmarks, which may be used to assist the surgeon in placing the implants into a safe and biomechanically advantageous position. These intra-operative radiographic views may also be acquired using intra-operative CT scans and/or x-ray imaging.

Figure 5:
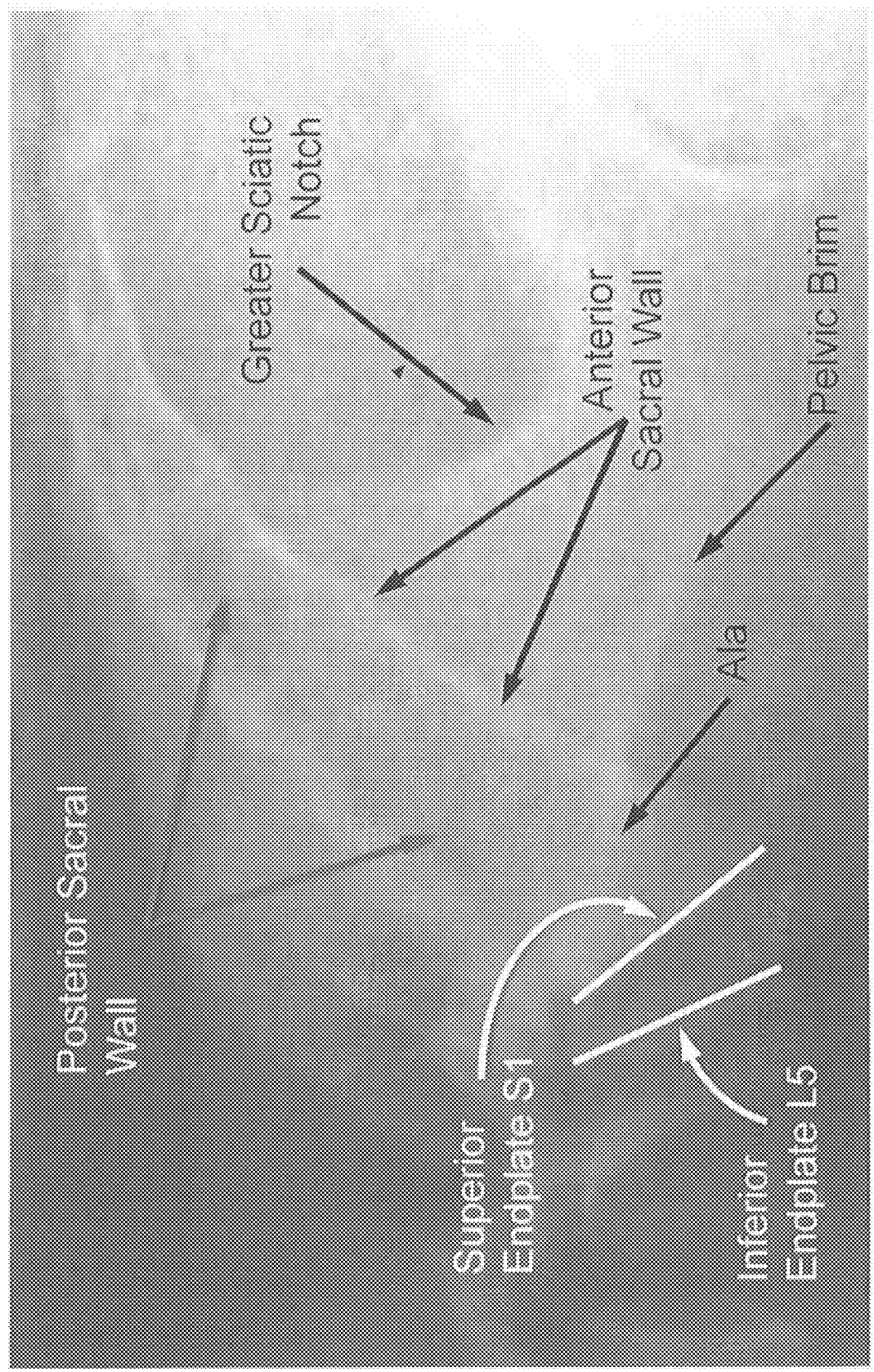
FIG. 5 illustrates an annotated lateral radiographic view of the lower lumbar spine and sacrum that shows various anatomical landmarks.

FIG. 5 illustrates an annotated lateral radiographic view of the lower lumbar spine and sacrum. Various landmarks that may be used to facilitate implant placement are notated on this image. In the lateral view, the sacrum will appear as a curved wedge, with the posterior sacral cortical wall and the anterior sacral cortical wall being readily visible. In standard radiographic views denser tissues such as bone generally show up as white or light grey and the less dense soft tissues generally show up as black or dark grey. The posterior sacral cortical wall and the anterior sacral cortical wall appear as slightly curved dense white lines that define a triangular wedge shape on the lateral view. Other osseous anatomic landmarks useful for orientation and positioning include the sacral ala, the pelvic brim, the greater sciatic notch, the superior endplate of the S1 vertebrae and the inferior endplate of the L5 vertebrae.

Figure 6A:
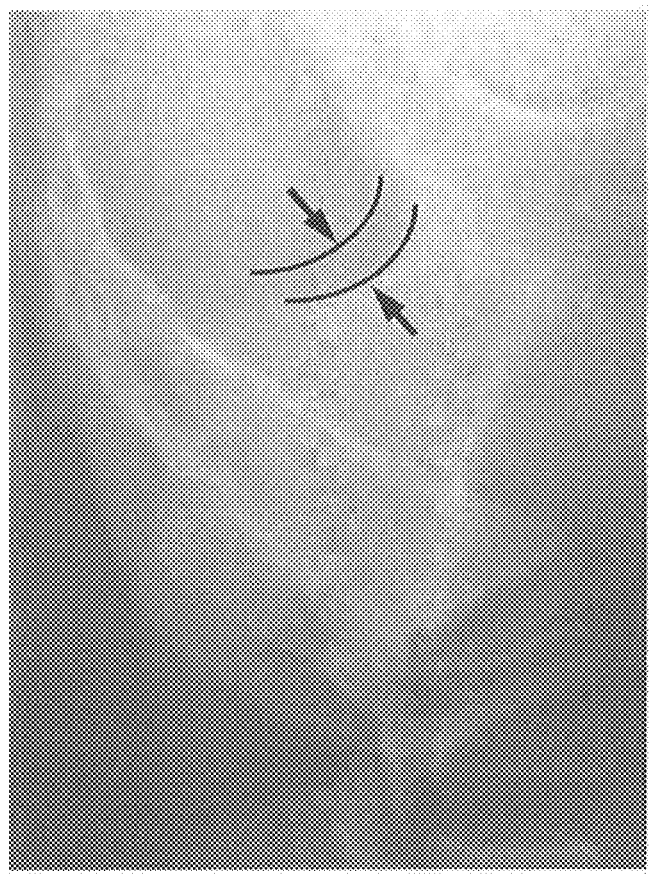
FIGS. 6A and 6B illustrate landmarks in the lateral view that can be used to position and orient the C-arm to obtain a true lateral view.
Figure 6B:
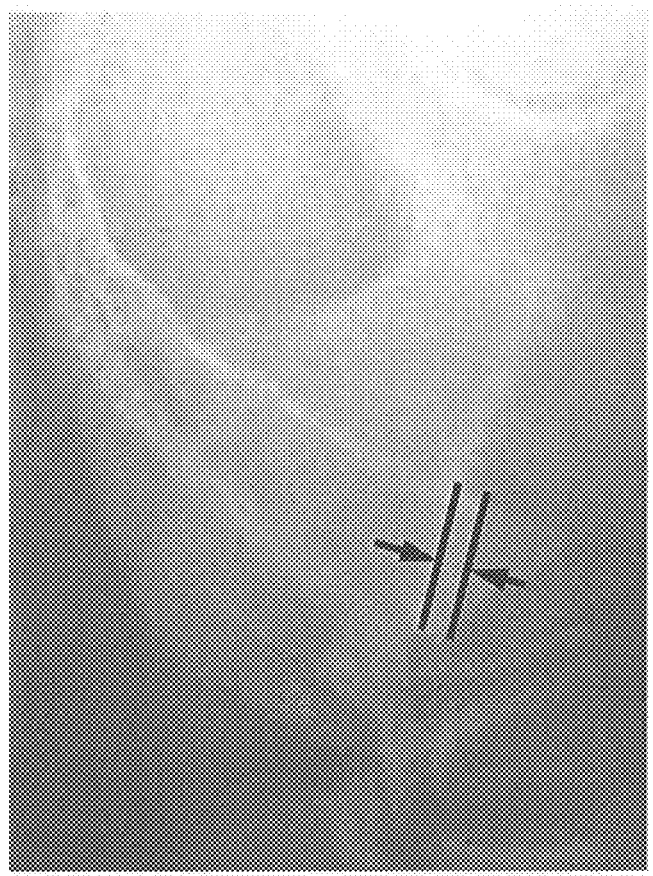

The C-arm may be positioned to allow a true orthogonal lateral view of the sacrum and lower lumbar spine. FIGS. 6A and 6B illustrate landmarks in the lateral view that can be used to position and orient the C-arm to obtain this true lateral view. An initial lateral fluoroscopic image is obtained and then the C-arm positioning is adjusted until certain anatomic landmarks (left and right) are superimposed on the lateral image signaling that the C-arm is aligned correctly. For example, the disk space between the endplates of L5 and S1 may be aligned based on the initial lateral fluoroscopic imaging and subsequent adjusted images until the visualized endplates of L5 and S1 are parallel and in focus, which occurs when the disk space is perpendicular to the image plane. At this point the two sciatic notches, one from the right ilium and one from the left ilium, should overlap on the lateral fluoroscopic images. The alignment is considered final when the left and right iliac cortical densities, which are also known as the alar lines, are directly superimposed on the lateral fluoroscopic image. The C-arm and the table are adjusted in multiple planes until the alignment described above is achieved.

Figure 7B:
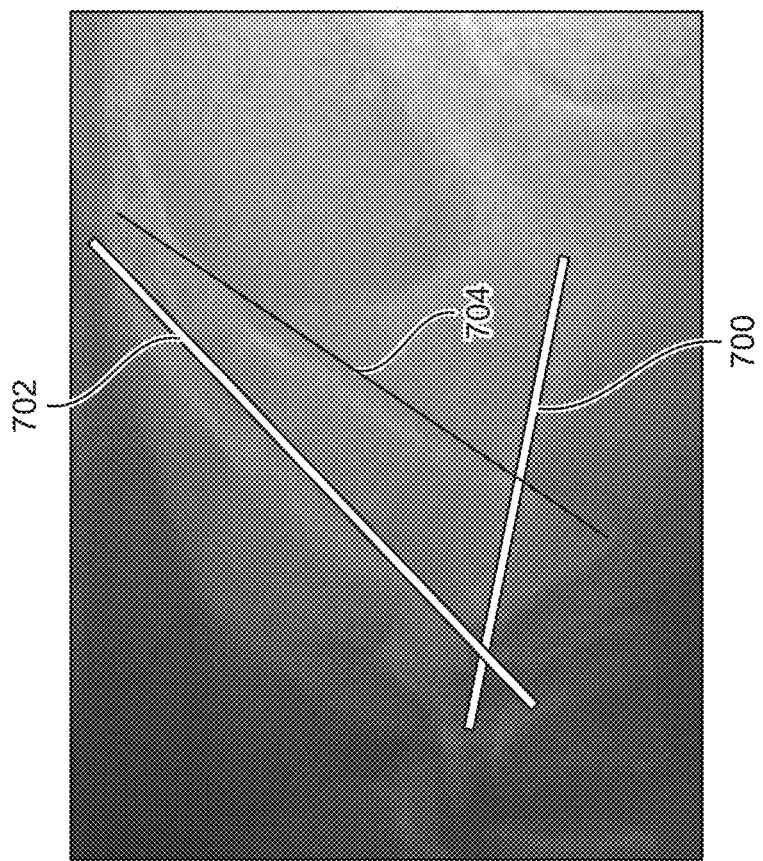
FIGS. 7A and 7B illustrate locations on the patient's skin that may be marked to provide visual guidance or mapping that correlates with the position of various osseous landmarks identified using the lateral radiographic view.
Figure 7A:
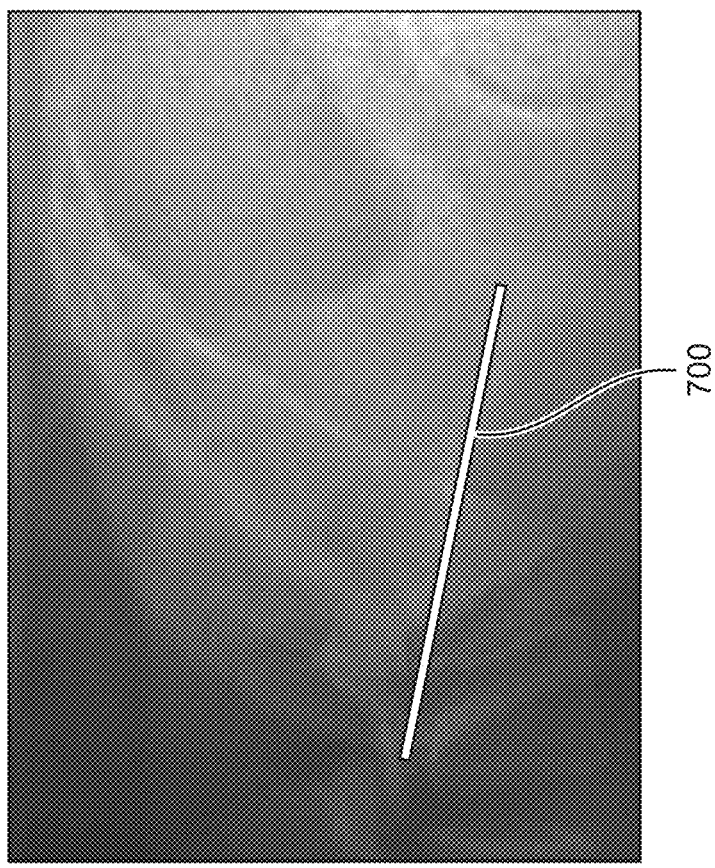

As illustrated in FIGS. 7A and 7B, once a true lateral view has been obtained, the patient's skin may be marked to provide visual guidance or mapping on the patient's skin that correlates with the position of various osseous landmarks identified using the lateral radiographic view. For example, the skin may be marked along the sacral ala and pelvic brim to create a first mark 700, and the skin along the posterior cortex of the sacral body can be marked to create a second mark 702, as illustrated in FIGS. 7A and 7B. In addition, a third mark 704 may be placed overlying the anterior cortex of the sacral body. One or more guide pins, which are easily visible under the C-arm image generated by the fluoroscope, can be used to help locate the landmarks, such as the sacral ala and the posterior cortex of the sacral body. Other radiopaque markers may be used in place of the pin to help located the position of the landmarks. The surgeon may lay the pin against the skin over where the underlying osseous landmark is predicted or estimated to be located, and a C-arm image is used to confirm whether the pin is in the correct position. If the pin(s) are correctly positioned over the landmarks, the mark is then drawn on the skin. If the pin(s) are not correctly positioned, the surgeon may reposition the pin(s) and check pin placement under fluoroscopy until the pin(s) are correctly positioned.

Figure 8A:
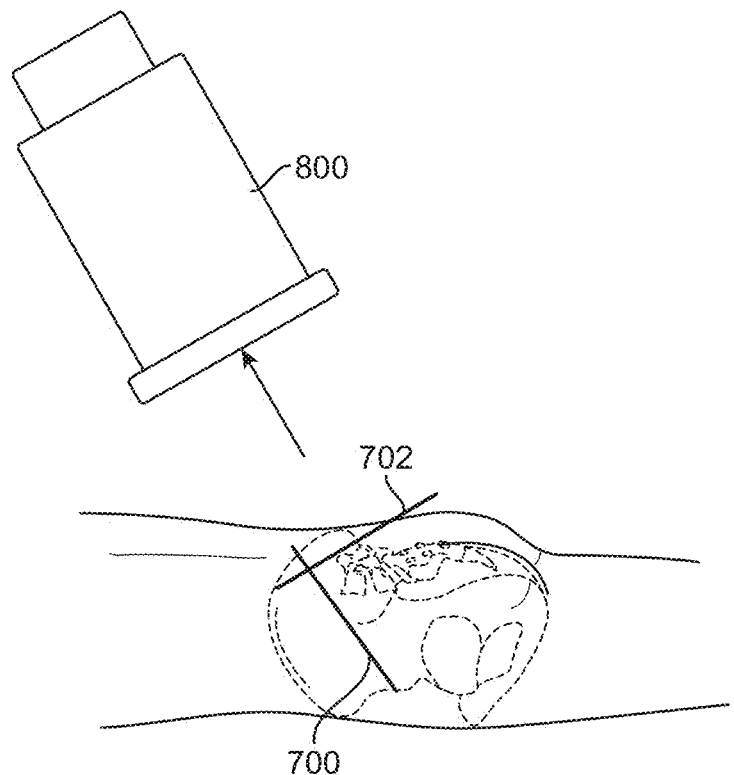
FIGS. 8A and 8B illustrate how the skin marks in FIGS. 7A and 7B may be used as a guide to align the C-arm in the outlet view and the inlet view.
Figure 8B:
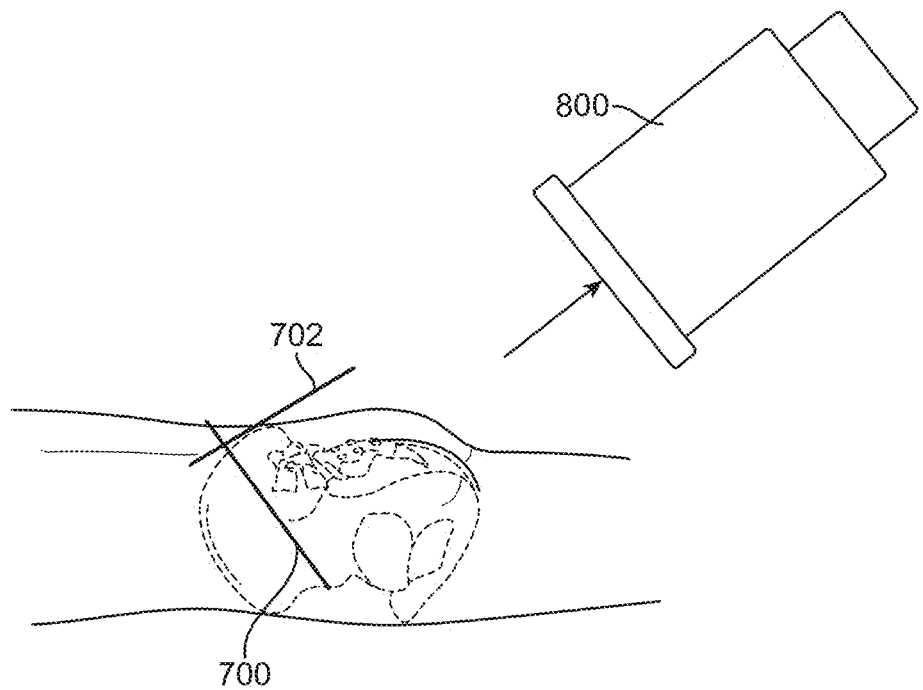

As illustrated in FIGS. 8A and 8B, the skin marks 700, 702 may be used as a guide to align the C-arm in the outlet view and the inlet view. For example, in some instances, for an outlet view, the C-arm detector 800 is positioned over the patient's lower back and oriented perpendicular or normal to the mark 702 identifying the posterior sacral body, and for an inlet view, the C-arm detector 800 is positioned over the patient's legs and oriented parallel to the mark 702 identifying the anterior cortex of the sacral body. The C-arm may then be adjusted in both the outlet and the inlet views until the underlying osseous anatomy is clearly visualized. For example, in the outlet view the C-arm can be adjusted and oriented such that the pubic symphysis and S2 neural foramina are superimposed on the fluoroscopic image. In some embodiments, the neural foramina of S1, S2, S3 or S4 may be aligned with the pubic symphysis. In the inlet view the C-arm can be adjusted and oriented such that the sacral prominence of S1 appears as a thin line on the fluoroscopic image. In addition, in some embodiments, the C-arm detector 800 can be placed under the table (not shown) instead of above the patient.

Figure 9A:
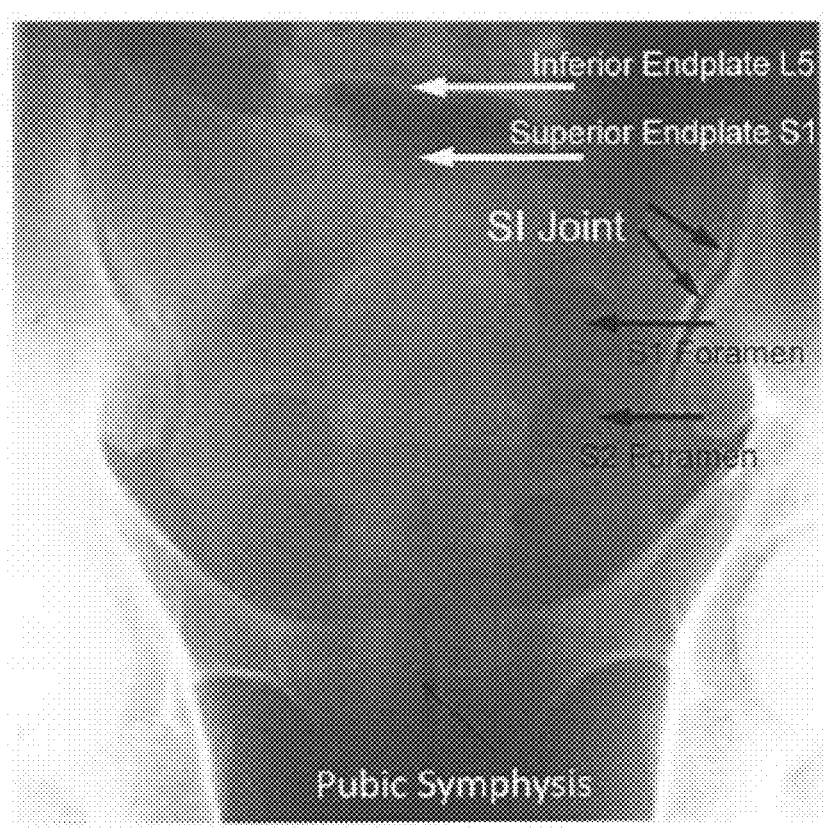
FIGS. 9A and 9B illustrate anatomical features and landmarks of the outlet view and the inlet view, respectively.
Figure 9B:
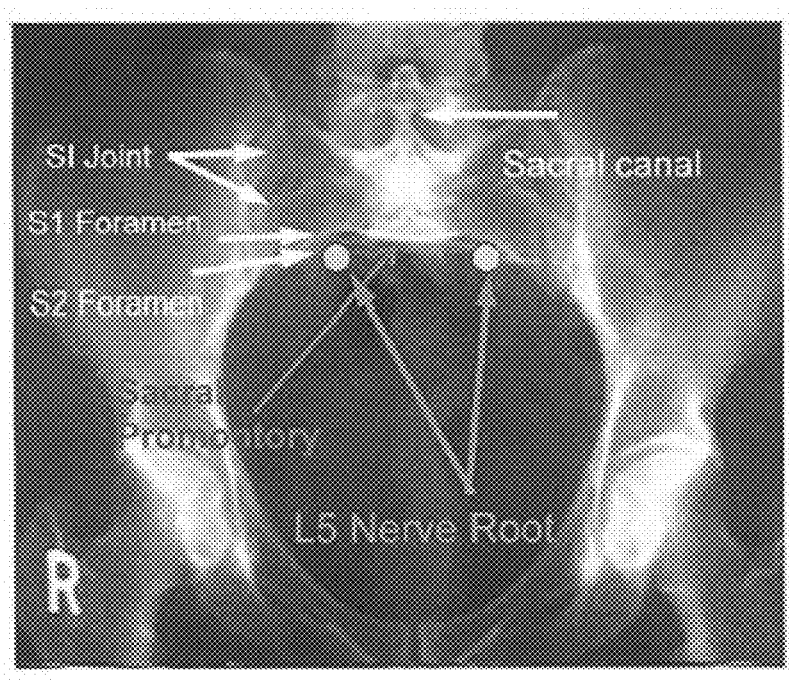

FIGS. 9A and 9B illustrate anatomical features and landmarks of the outlet view and the inlet view, respectively. The outlet view is an anterior to posterior view of the pelvis and sacrum that provides a clear visualization of the sacral neuro-foramina, such as the S1 foramen and the S2 foramen, as well as other structures such as the inferior endplate L5 and the superior endplate S1. The inlet view is an anterior to posterior view of the pelvis that provides a clear visualization of the ventral (anterior) cortex of the sacrum. To obtain the inlet view, the C-arm of the fluoroscope is tilted towards the patient's feet until the dense cortical line of the S1-S2 vestigial disk directly overlies the dense cortical line of the sacral promontory. In the inlet view, the sacral canal, the ventral cortex of the sacral body and the sacral alar areas are visualized by the surgeon. Visualization of the osseous anatomy of the sacral ala and the sacral canal allows the surgeon to insert the implants across the SI-Joint, to keep the leading portion of the implants positioned within the sacral ala while avoiding damage to the neural tissues and vascular structures. In addition, left and right oblique inlet and outlet views can be obtained to better visualize the sacroiliac joint and surrounding sacral foramina. With the C-arm in the inlet position, an oblique inlet image can be obtained by rotating the C-arm approximately 15 degrees to either side of the patient such that the C-arm's beam is approximately parallel to the SI-Joint and the lateral cortical walls of the S1 and S2 foramina. Similarly, with the C-arm in the outlet position, an oblique outlet image can be obtained by rotating the C-arm approximately 15 degrees to either side of the patient such that the C-arm's beam is approximately parallel to the SI-Joint and the lateral cortical walls of the S1 and S2 foramina.

Implant Placement

Proper implant placement across the SI-joint is determined by the surgeon selecting and maintaining the correct implant starting position, the correct implant insertion trajectory, and the correct implant length, which may all be determined with appropriate preoperative planning. Preoperative planning includes careful evaluation of osseous anatomy to identify the various landmarks described herein using CT scans and plane radiographs. Safe placement of implants involves placing the implants across the SI joint keeping the sacral portion of the implants within the osseous confine of the sacrum while avoiding the nerve tunnels of the spinal canal and neuroforamina, avoiding malposition of the implant in the dysplastic sacrum, and avoiding in-out-in positioning secondary to the concavity of the ventral surface of the sacral ala.

Figure 10B:
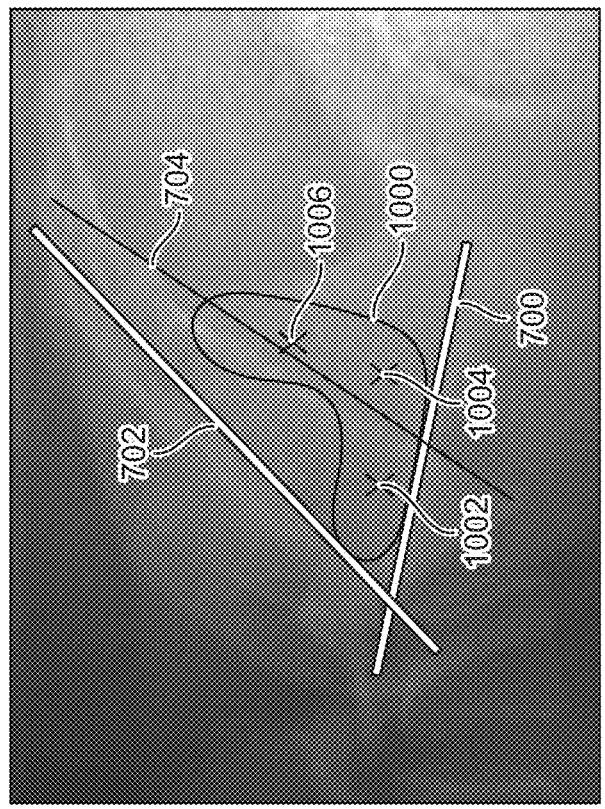
FIGS. 10A and 10B are lateral views that illustrate an embodiment of an implant target zone that results in the implants passing through the articular or hyaline cartilage portion of the SI-joint rather than the fibro cartilaginous portion of the SI-joint.
Figure 10A:
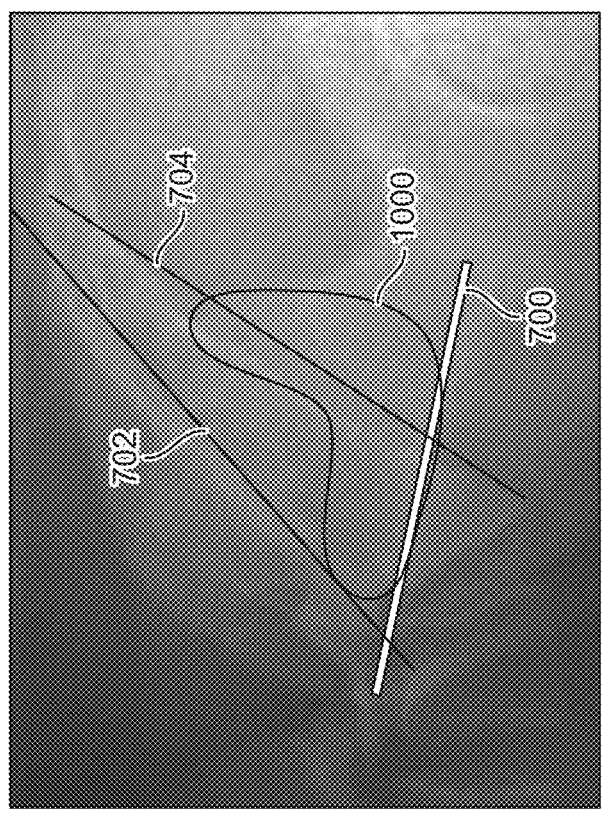

FIGS. 10A and 10B are lateral views that illustrate an embodiment of an implant target zone 1000 that results in the implants passing through the articular or hyaline cartilage portion of the SI-joint rather than the fibro cartilaginous portion of the SI-joint. The articular cartilage is associated with denser and stronger subchondral bone that can improve implant stability. Therefore, implants can be implanted into the denser and stronger subchondral bone by passing through the articular bone outlined by the implant target zone 1000. The location of the articular cartilage is shown as a boomerang or V-shaped outline that is located generally along the anterior portion of the SI-joint. The implant target zone 1000 is shown with reference to the various anatomical landmarks in the lateral view, including the alar line 700, the posterior sacral body line 702, and the anterior sacral body line 704. In addition, the anterior portion of the implant target zone 1000 is defined by the anterior cortex of the sacral ala, which is the curved portion of the anterior sacrum that extends from the sacral body to the ilium. In FIG. 10A and 10B, the anterior portion of the implant target zone 1000 includes the portion of the implant target zone 1000 that is anterior the anterior sacral body line 704. In a lateral view and an inlet view, as illustrated in FIGS. 9C and 9D, the anterior cortex of the sacral ala is visible as the most anterior aspects of the sacrum. In the lateral view illustrated in FIG. 9C, the anterior cortex of the sacral ala is defined generally by the anterior sacral body line 704, the greater sciatic notch, and the superior surface of the sacral ala which forms the alar line 700. Three implantation sites 1002, 1004, 1006 are shown within the implant target zone 1000 in FIG. 10B, with two implantations sites 1004, 1006 located in the anterior portion of the implant target zone 1000 that corresponds to the anterior cortex of the sacral ala. The anterior cortex of the sacral ala can serve as a landmark for positioning those two implantation sites 1004, 1006.

Figure 10D:
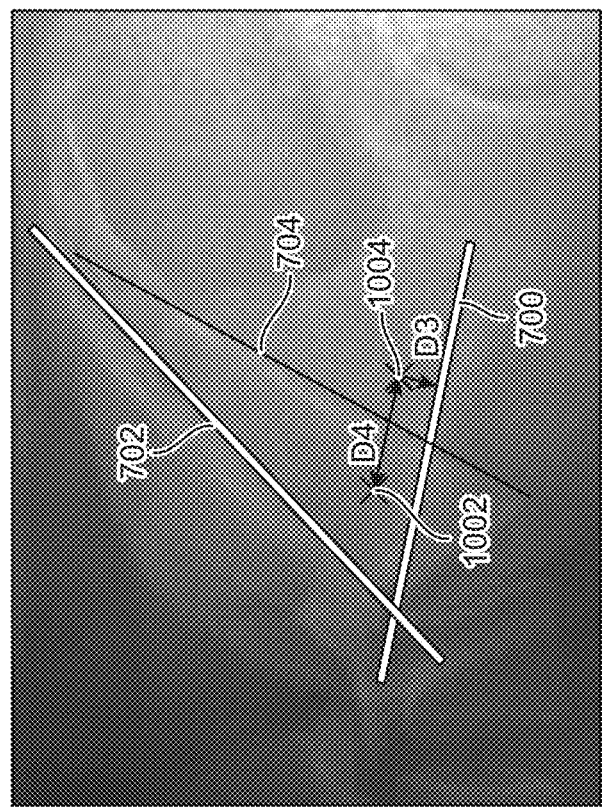
FIG. 10D illustrates a second implantation site that can be placed with reference to the alar line and the location of the first implantation site such that the second implantation site is inferior (caudal) and anterior to the first implantation site and placed in a middle portion of articular cartilage, near the vertex of the boomerang.
Figure 10C:
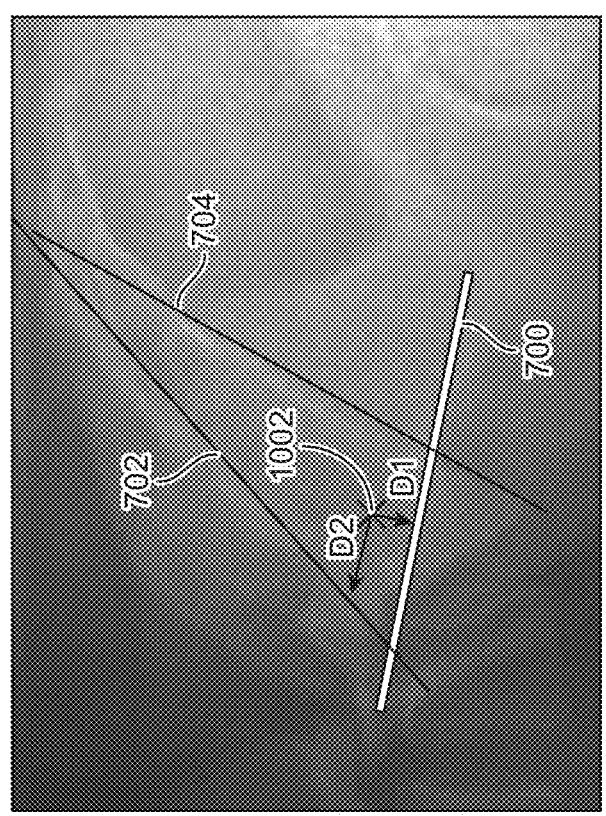
FIG. 10C illustrates a first implantation site placed with reference to both the alar line and the posterior sacral body line.

In some embodiments, as shown in FIG. 10C, a first implantation site 1002 can be placed with reference to both the alar line 700 and the posterior sacral body line 702. In some embodiments, the first implantation site 1002 can be placed with additional reference to the anterior sacral body line 704. For example, in some embodiments the first implantation site 1002 can be placed approximately 3 mm to 10 mm from the alar line, D1, and approximately 3 mm to 20 mm from the posterior sacral body line 702, D2, where the distance from the posterior sacral body line 702 is measured along a line parallel to the alar line 700. In some embodiments, the first implantation site 1002 can be placed approximately 5 mm from the alar line 700 and about 10 mm from the posterior sacral body line 702. The goal for the first implantation site 1002 is to place the implant in a superior (cephalad) portion of the articular cartilage by using the alar line 700 and the posterior sacral body line 702 for reference. In some embodiments, the first implantation site 1002 can be placed with additional reference to the anterior sacral body line 704, such that the first implantation site 1002 is positioned approximately in the midpoint of the posterior and anterior sacral body lines 702, 704. In some embodiments, the first implantation site 1002 is positioned anterior of the midpoint of the posterior and anterior sacral body lines 702, 704.

In some embodiments, as shown in FIG. 10D, the second implantation site 1004 can be placed with reference to the alar line 700 and the location of the first implantation site 1002 such that the second implantation site 1004 is inferior (caudal) and anterior to the first implantation site 1002 and placed in a middle portion of articular cartilage, near the vertex of the boomerang. In some embodiments, the second implantation site 1004 can be located anterior of the anterior sacral body line 704. In some embodiments, the second implantation site 1004 can be placed approximately 3 mm to 10 mm from the alar line 700, D3. In some embodiments, the second implantation site 1004 can be placed approximately the same distance from the alar line 700 as the first implantation site 1002, such that D1 and D3 are approximately equal and a line joining the first implantation site 1002 with the second implantation site 1004 is approximately parallel to the alar line 700. In some embodiments, the second implantation site 1004 can be positioned about 10 mm to about 40 mm from the first implantation site 1002, D4. The distance between the first implantation site 1002 and the second implantation site 1004 is generally, at a minimum, at least equal to the diameter of the implant so that the two implants do not overlap. In some embodiments, a guide pin jig can be used to help place the guide pin for the second implantation site 1004. The guide pin jig can have two holes for receiving guide pins that are separated by a predetermined distance, D4. In some embodiments, the guide pin jig can have a hole for the first guide pin and a slot for receiving the second guide pin, so that the distance between the two guide pins can be varied between about 10 mm to about 40 mm. In some embodiments, the slot can have distance markings showing the distance from the hole for the first guide pin. More generally, the guide pin jig can be used to place the next guide pin by using the position of a previously placed guide pin.

Figure 10E:
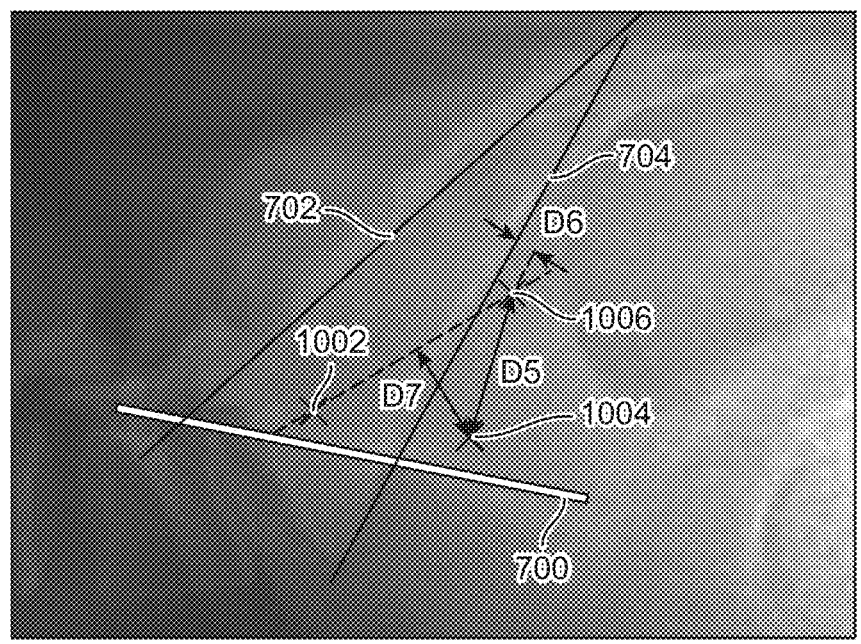
FIG. 10E illustrates a third implantation site that can be placed with reference to the anterior sacral body line and the second implantation site, so that the third implantation site is positioned in an inferior (caudal) portion of the articular cartilage.

In some embodiments, as shown in FIG. 10E, the third implantation site 1006 can be placed with reference to the anterior sacral body line 704 and the second implantation site 1004, so that the third implantation site 1006 is positioned in an inferior (caudal) portion of the articular cartilage. In some embodiments, the distance between the third implantation site 1006 and the second implantation site 1004, D5, can be approximately equal to the distance between the first implantation site 1002 and the second implantation site 1004, D4. In some embodiments, D5 can be between about 0.5 to 2 times the magnitude of D4. In some embodiments, the third implantation site 1006 can be about 0 to 5 mm anterior of the anterior sacral body line 704, D6. In some embodiments, the third implantation site 1006 can be about 2 or 3 mm anterior to the anterior sacral body line 704. As illustrated in FIG. 10E, the three implantation sites 1002, 1004, 1006 are located in the anterior articular portion of the SI-joint and are non-colinear. If a line is drawn through the first implantation site 1002 and the third implantation site 1006, the second implantation site 1004 is offset from the first and third implantation site by a distance, D7, which can be about 1 to 15 mm.

The implantation sites described above specify the initial guide pin placement. In addition to the initial placement, guide pin and implant orientation can be specified to optimize the location of the implants across the SI-joint after initial guide pin placement. To orient the guide pins, in addition to the lateral views illustrated in FIGS. 10A-10E, the outlet and inlet views described above provide additional landmarks that facilitate guide pin orientation. Although the following description describes the various guide pins in terms of a first guide pin, a second guide pin, and a third guide pin, the actual order of insertion can be varied such that any one of the guide pins can be inserted first, second, or third.

Figures 11A, 11B, 11C:
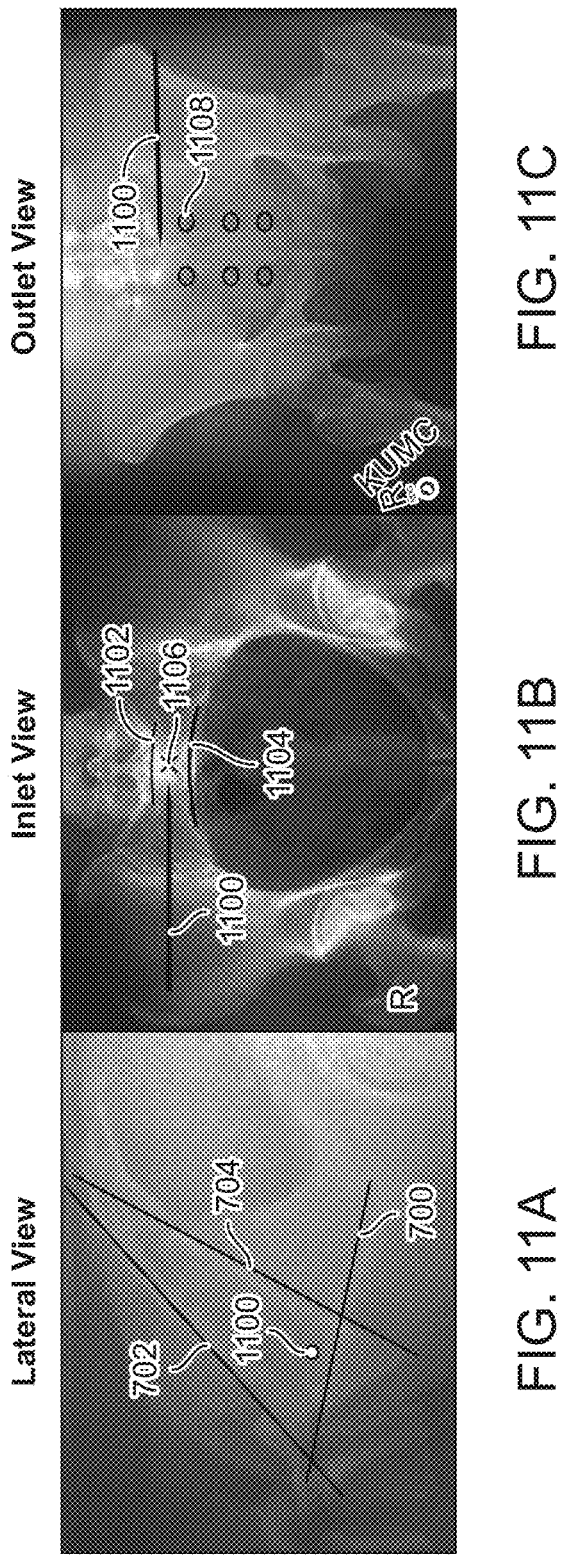
FIGS. 11A-11C illustrate the orientation of a first guide pin inserted into the first implantation site in the lateral view, the inlet view, and the outlet view.

For example, FIGS. 11A-11C illustrate the orientation of the first guide pin 1100 inserted into the first implantation site in the lateral view, the inlet view, and the outlet view. These illustrations and the other illustrations described herein are illustrative, and variations may occur depending on the particular orientations in which the various views are taken. As shown in FIG. 11A, the first guide pin 1100 is driven substantially axially in the lateral view such that the first guide pin 1100 appears to be driven into the page. In the inlet view shown in FIG. 11B, the first guide pin 1100 is advanced towards the middle of the space defined by the anterior sacral line 1104 and posterior sacral line 1102. This target 1106 is illustrated by an X. In some embodiments, the first guide pin 1100 can be advanced proximate the target 1106 since the first guide pin 1100 should not encounter any neural structures in this orientation, allowing a longer implant to be used for the first implant. In addition, in some embodiments, the first guide pin 1100 is advanced substantially horizontally in the inlet view. As illustrated in FIG. 11C, in the outlet view the first guide pin 1100 is advanced substantially horizontally and is also usually advanced above the S1 foramen 1108.

Figures 12A, 12B, 12C:
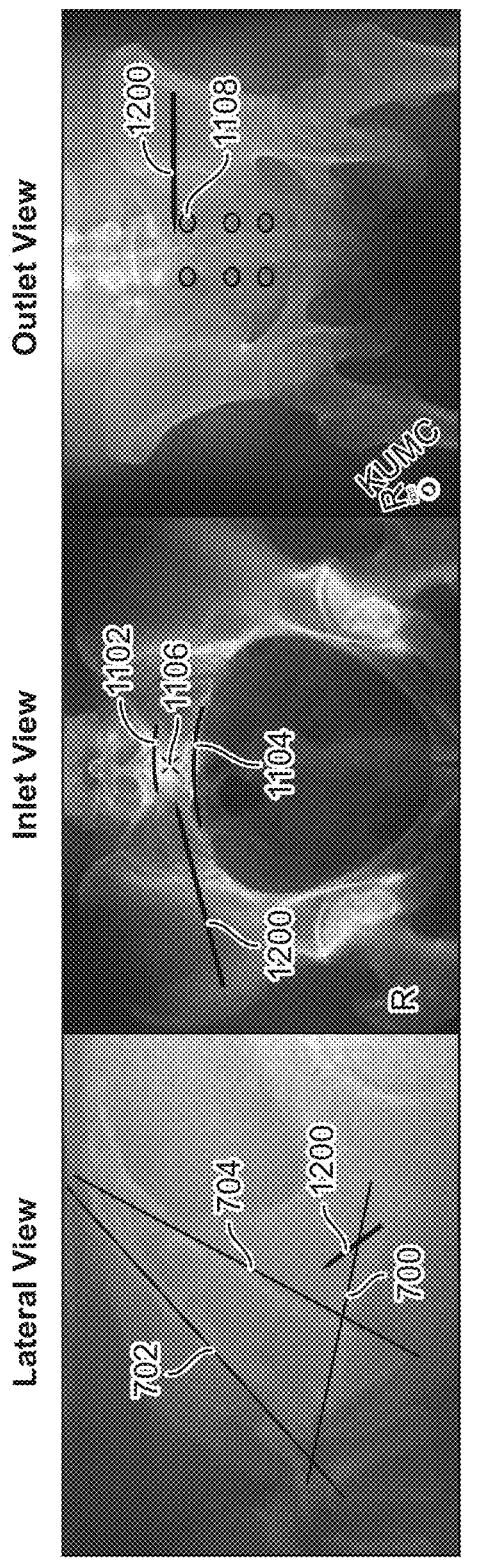
FIGS. 12A-12C illustrate the orientation of a second guide pin inserted into the second implantation site in the lateral view, the inlet view, and the outlet view.

FIGS. 12A-12C illustrate the orientation of the second guide pin 1200 inserted into the second implantation site in the lateral view, the inlet view, and the outlet view. As shown in FIG. 12A and 12B, the second guide pin 1200 is inserted at an angle α with respect to the horizontal axis of the inlet view. See also FIGS. 14A and 14B. To determine the correct angle of insertion, the distal end of the second guide pin 1200 is placed or docked at the second implantation site. Then the angle of the second guide pin 1200 is set by swinging out the proximal end of the second guide pin 1200 while keeping the distal end fixed until the second guide pin 1200 is pointed towards target 1106 illustrated in the inlet view of FIG. 12B, while keeping the second guide pin 1200 substantially horizontal in the outlet view shown in FIG. 12C. In some embodiments, the guide pin 1200 has a trajectory in the inlet view that is centered on the middle third of the body of S1 and aimed towards the target 1106. In general, when the implantation site is located anterior of the anterior sacral body line 704 in the lateral view, the guide pin is angled by swinging out the proximal end of the guide pin while keeping the distal end fixed until the guide pin is pointed towards target 1106 illustrated in the inlet view. This allows the guide pin to follow the anterior surface of the ala and sacrum without exiting the anterior surface. In some embodiments, the second guide pin 1200 is also advanced superior (cephalad) the S1 foramen but inferior (caudal) to the first guide pin in the outlet view. When the second guide pin 1200 is advanced superior (cephalad) the S1 foramen 1108, it can be possible to advance the second guide pin 1200 all the way to target 1106 as above for the first guide pin. In other embodiments, the second guide pin 1200 can be advanced horizontally towards the S1 foramen 1108 in the outlet view, in which case the second guide pin 1200 is advanced up to but not into the S1 foramen 1108.

Figures 13A, 13B, 13C:
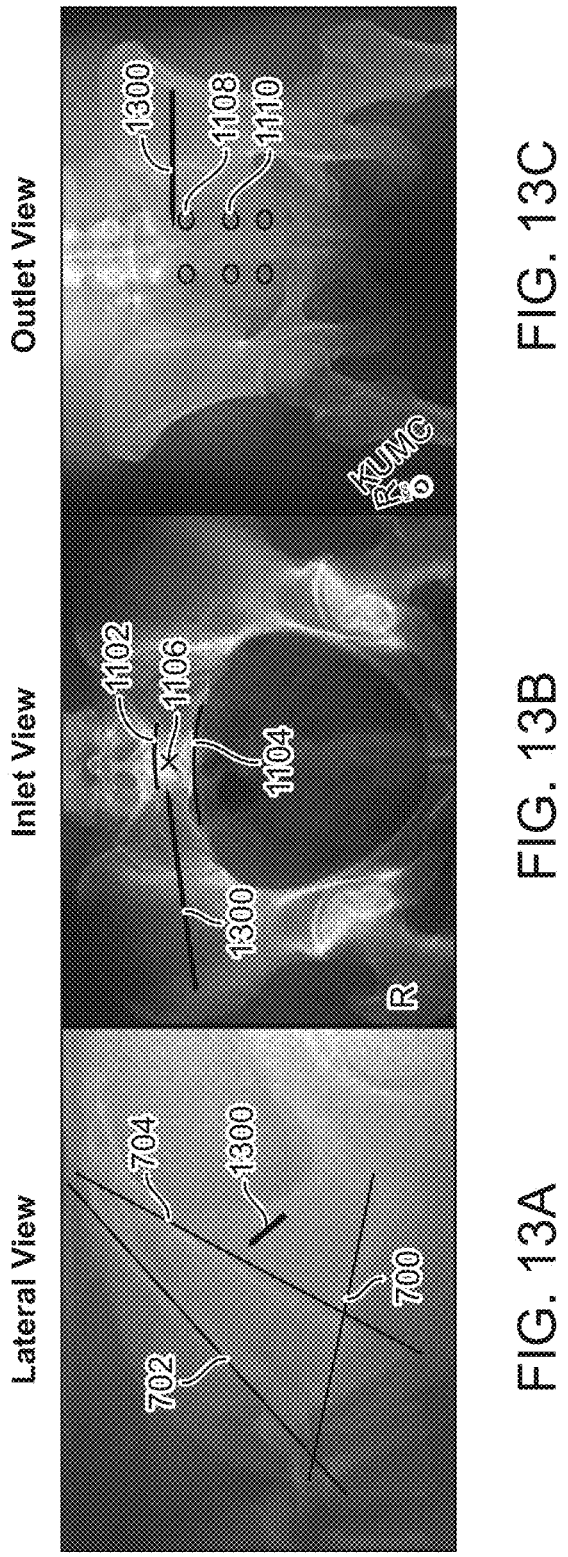
FIGS. 13A-13C illustrate the orientation of a third guide pin inserted into the third implantation site in the lateral view, the inlet view, and the outlet view.

FIGS. 13A-13C illustrate the orientation of the third guide pin 1300 inserted into the third implantation site in the lateral view, the inlet view, and the outlet view. As shown in FIG. 13A, the third guide pin 1300 is inserted at an angle in the lateral view, which is expected when the implantation site is anterior of the anterior sacral body line 704 as shown. As shown in FIG.13B, the third guide pin 1300 is also advanced towards the target 1106 at an angle β to the horizontal axis. As described above, the angle of the guide pin is set by swinging out the proximal end of the guide pin while keeping the distal end fixed until the guide pin is pointed towards target 1106 illustrated in the inlet view of FIG. 13B, while keeping the guide pin substantially horizontal in the outlet view shown in FIG. 13C. As shown in FIG. 13C, the third guide pin 1300 is advanced substantially horizontally in the outlet view such that the third guide pin 1300 is directed towards the S1 foramen 1108. In this case, the third guide pin 1300 is advanced up to but not within the S1 foramen 1108. In other embodiments, the third guide pin 1300 can be directed between the S1 foramen 1108 and the S2 foramen 1110, when the third implantation site is located more inferiorly (caudally) than illustrated in FIGS. 13A-13C. In this case, the third guide pin 1300 can be advanced past the S1 foramen 1108 and the S2 foramen 1110 to the medial portion of the sacrum, similar to the first guide pin.

Figures 14A, 14B, 14C:
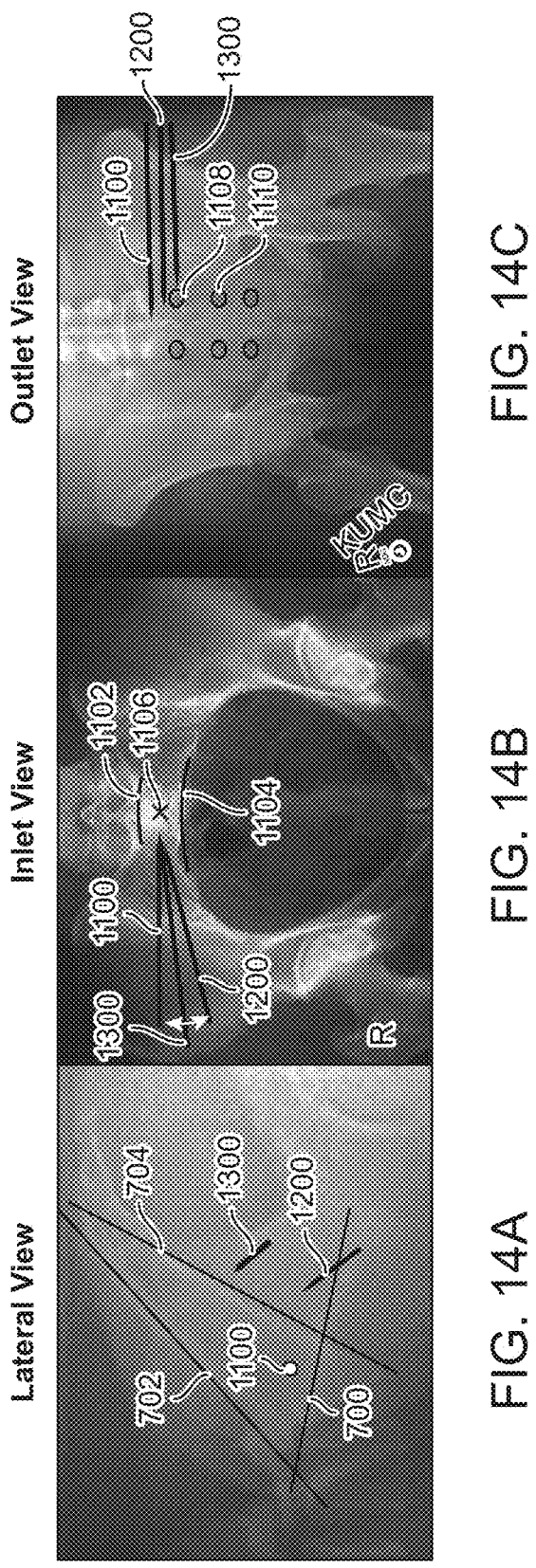
FIGS. 14A-14C illustrate the orientation of the three guide pins in the lateral view, the inlet view, and the outlet view.

FIGS. 14A-14C illustrate the orientation of the three guide pins in the lateral view, the inlet view, and the outlet view. As shown in FIG. 14B, the first guide pin 1100 is inserted horizontally in the inlet view. The second guide pin 1200 is oriented at an angle α with respect to the first guide pin 1100 or the horizontal axis in the inlet view. Angle α can vary depending on the particular implantation site chosen. In some embodiments, angle α can vary between about 0 degrees to about 45 degrees, or about 0 degrees to about 30 degrees. The third guide pin 1300 is oriented at an angle β with respect to the first guide pin 1100 or the horizontal axis in the inlet view. In some embodiments, angle β can also vary between about 0 degrees to about 45 degrees, or about 0 degrees to about 30 degrees. In some embodiments, as shown, the angle β is less than angle α. In other embodiments, angle α is approximately equal to angle β. As described in more detail below, implants can be advanced over the guide pins, resulting in implants having the same position and orientation as the guide pins across the SI-joint. By having the implants oriented at an angle with respect to each other and not parallel to each other, resistance to lateral separation of the SI-joint is increased.

Figures 15A, 15B, 15C:
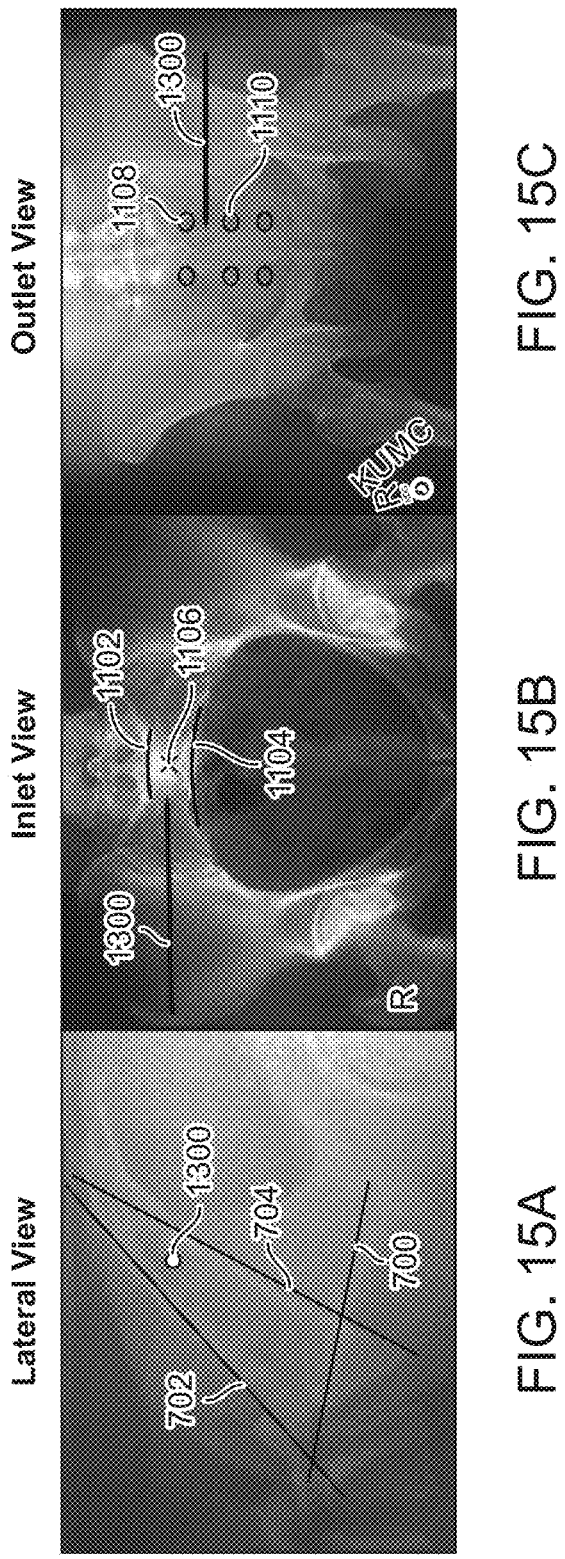
FIGS. 15A-15C illustrate another embodiment of the third guide pin position and orientation when the third implantation site is located in between the posterior sacral body line and the anterior sacral body line in the inlet view.

FIGS. 15A-15C illustrate another embodiment of the third guide pin 1300 position and orientation when the third implantation site is located in between the posterior sacral body line 702 and the anterior sacral body line 704 in the inlet view. In this embodiment, the inlet view may demonstrate that the first and third guide pin are superimposed and the outlet view may demonstrate that the first and third guide pin are substantially parallel. Because the implantation site is located between the posterior sacral body line 702 and the anterior sacral body line 704, the third guide pin can 1300 be inserted axially (into the page) in the lateral view and horizontally in the inlet view shown in FIG. 15B. FIGS. 15A and 15C illustrates the implantation site is located more inferior (caudal) than shown in FIGS. 13A-13C, and consequently, the third guide pin 1300 is advanced horizontally between the S1 foramen 1108 and the S2 foramen 1110 in the outlet view.

Figure 16A:
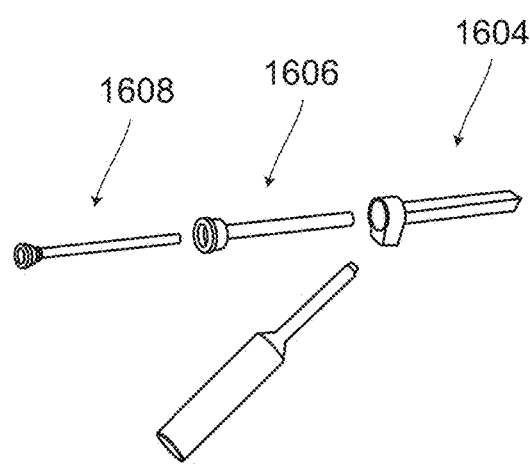
FIGS. 16A and 16B illustrate an assembly for receiving the guide pin.
Figure 16B:
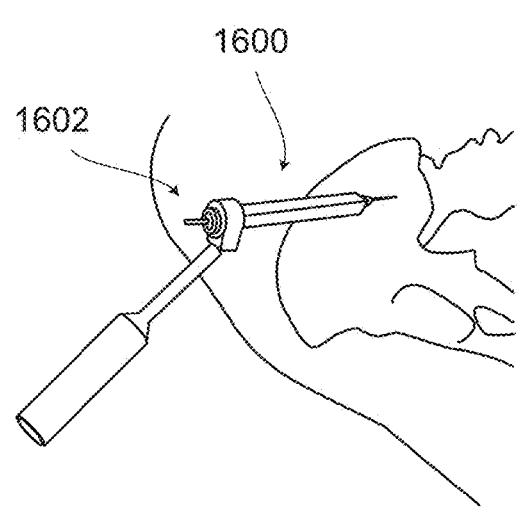
Figure 17:
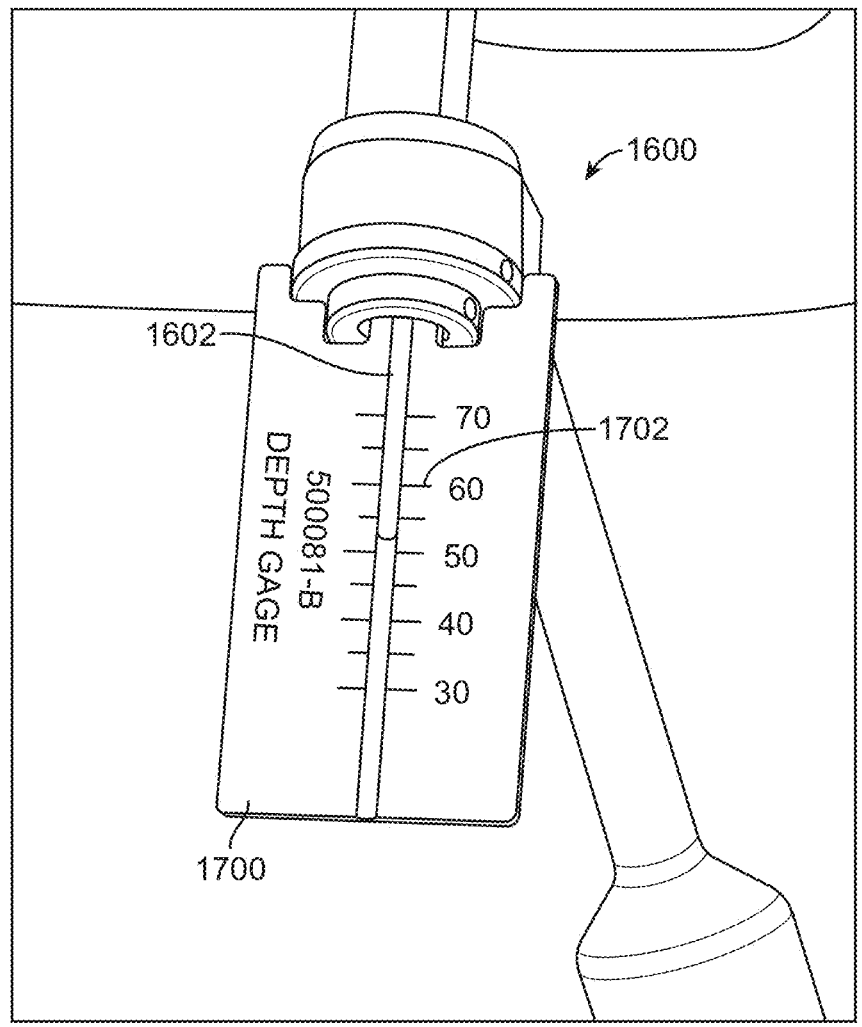
FIG. 17 illustrates a pin depth gage for determining the depth of insertion of the pin.

FIGS. 16A and 16B illustrate an assembly 1600 for receiving the guide pin 1602. The assembly can include a soft tissue protector 1604, a drill sleeve 1606 that is removably disposed within the soft tissue protector 1604, and a pin sleeve 1608 removably disposed within the drill sleeve 1606. The assembly 1600 can be slid over the guide pin 1602 until bony contact is achieved. FIG. 17 illustrates a pin depth gage 1700 that is placed against the proximal end of the assembly 1600 so that the proximal end of the guide pin 1602 is aligned with the depth gage markings 1702. The pin depth can then be read directly from the markings 1702 of the depth gage 1700, allowing the proper implant length to be selected. In some embodiments, the implant is left proud of the ilium's cortical wall by about 2 to 5 mm, so the implant size can be determined by adding 2 to 5 mm to the pin depth.

Figure 18:
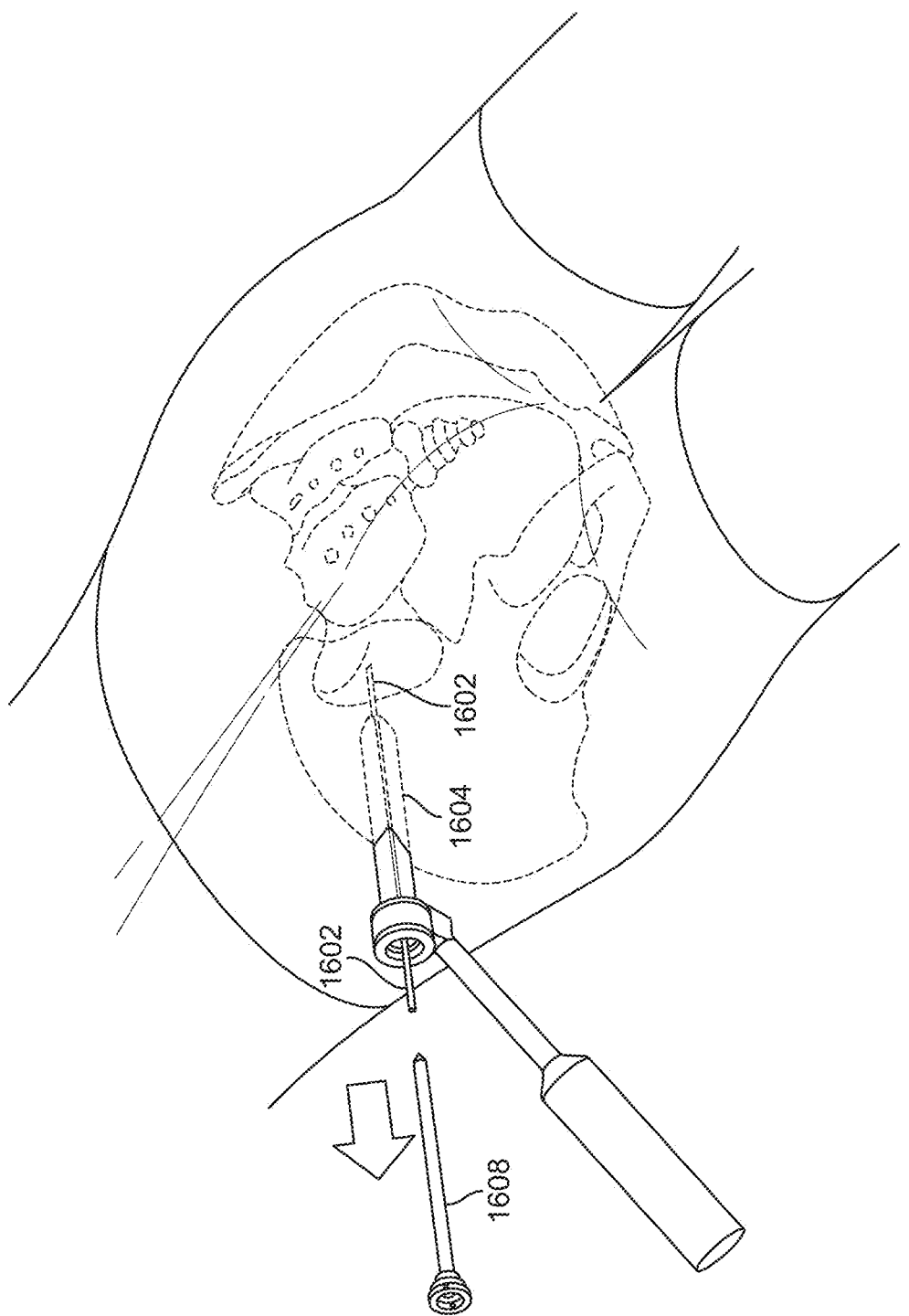
FIG. 18 illustrates removal of a pin sleeve from the guide pin.
Figure 19:
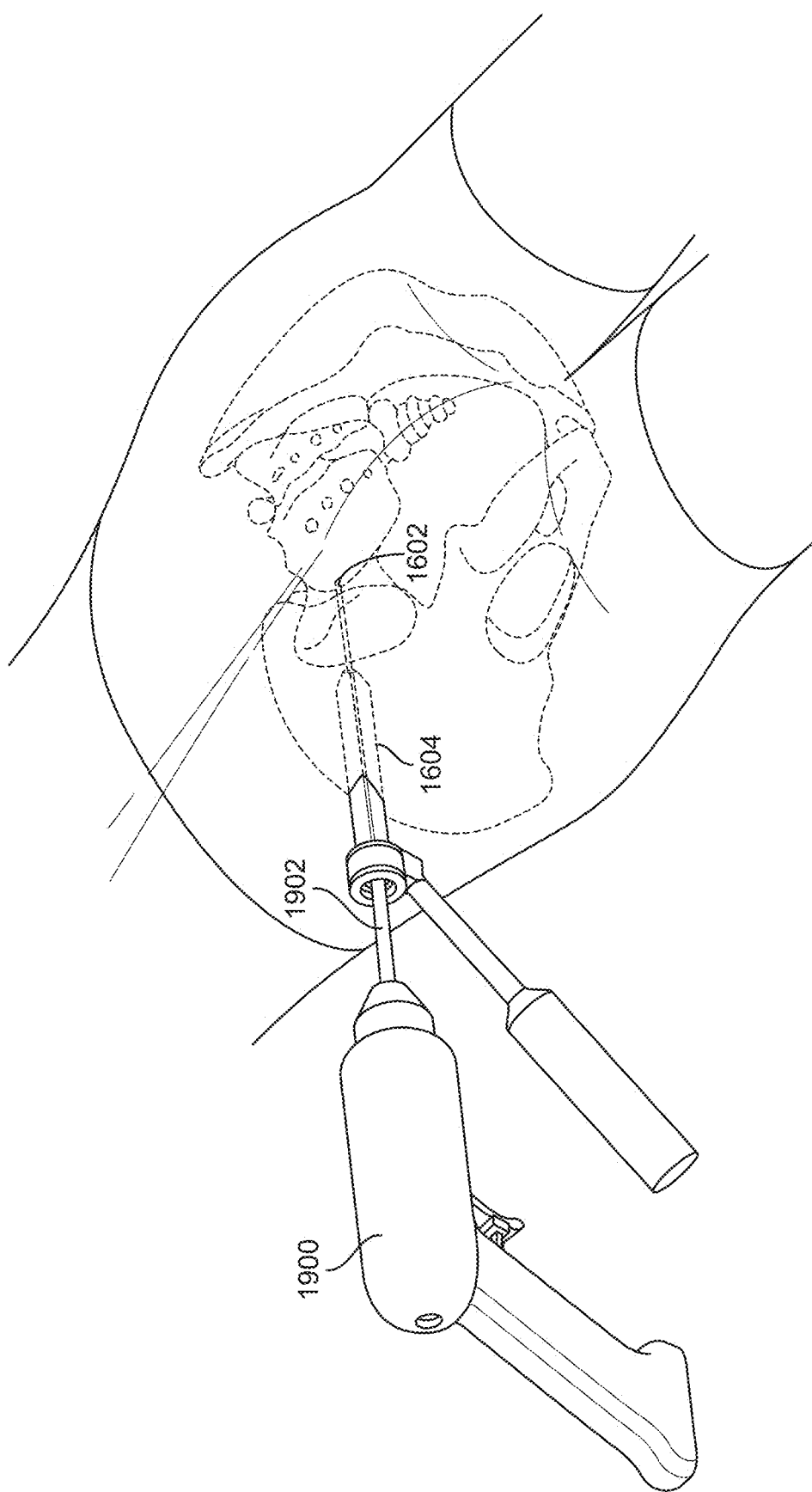
FIG. 19 illustrates insertion of a drill over the guide pin.
Figure 20:
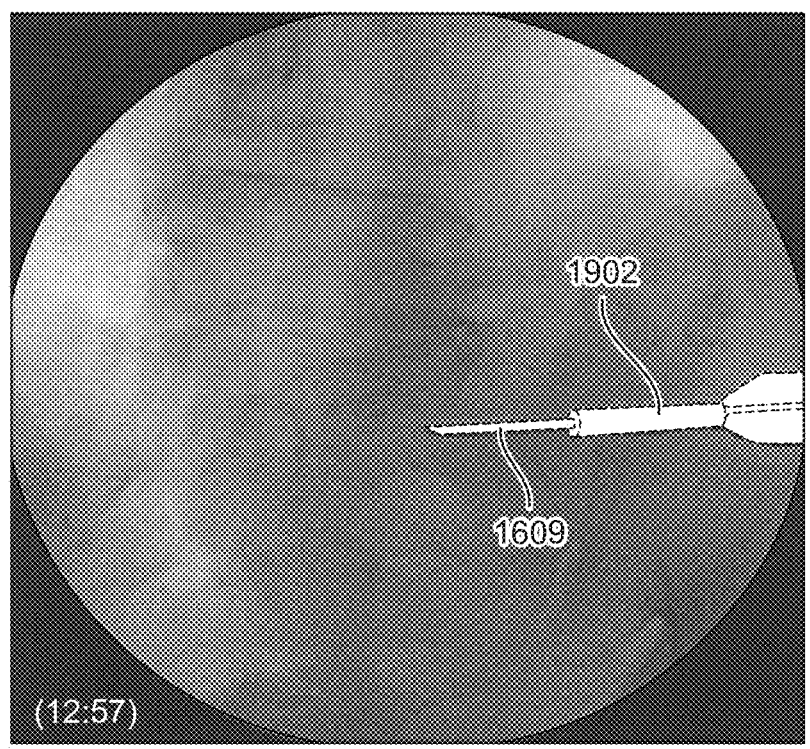
FIG. 20 illustrates drilling a bore through the lateral cortex of the sacrum in the outlet view.
Figure 21:
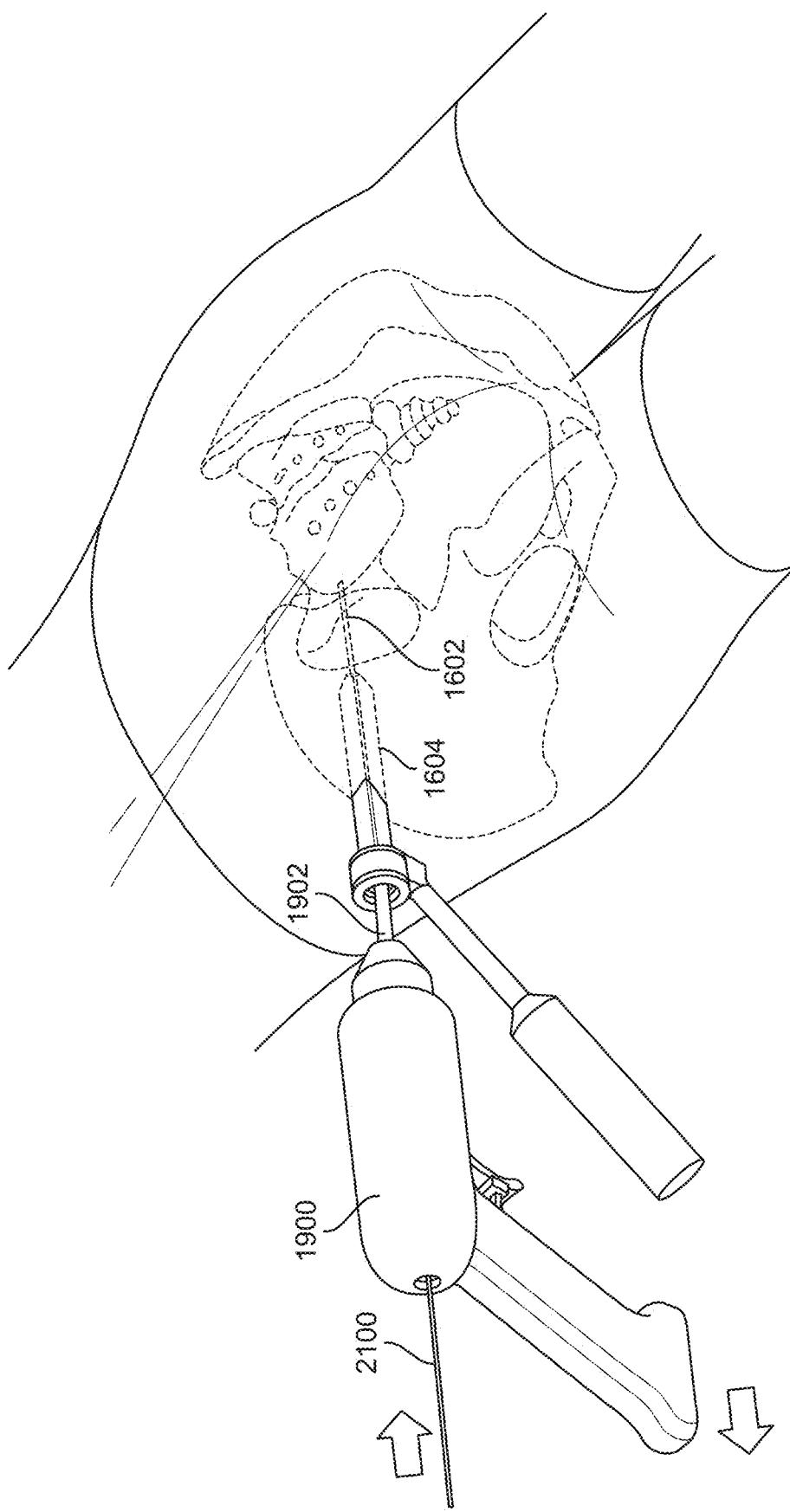
FIG. 21 illustrates removal of the drill after drilling the bore.

Next, as illustrated in FIGS. 18 and 19, the pin sleeve 1608 can be removed and a drill 1900 with a cannulated drill bit 1902 can be inserted over the guide pin 1602 to prepare a cavity for receiving the implant. Drilling can be monitored under fluoroscopy in the outlet view as illustrated in FIG. 20, allowing the user to monitor the depth of the drill and to watch for unwanted pin advancement. Drilling can be used to penetrate through the entirety of the ilium, to cross the SI joint and to penetrate the lateral cortex of the sacrum. Once the drill 1900 has reached the appropriate depth, the drill 1900 can be removed with the assistance of an exchange pin 2100, which can be inserted through the proximal end of the drill 1900 and drill bit 1902 until the exchange pin 2100 abuts against the guide pin 1602, as illustrated in FIG. 21. The exchange pin 2100 prevents the guide pin 1602 from withdrawing as the drill 1900 is removed. When placing the exchange pin 2100 against the guide pin 1602, care should be taken to avoid inadvertently advancing the guide pin 1602. After the drill 1900 is removed, the drill sleeve 1606 can also be removed from the assembly.

Figure 22B:
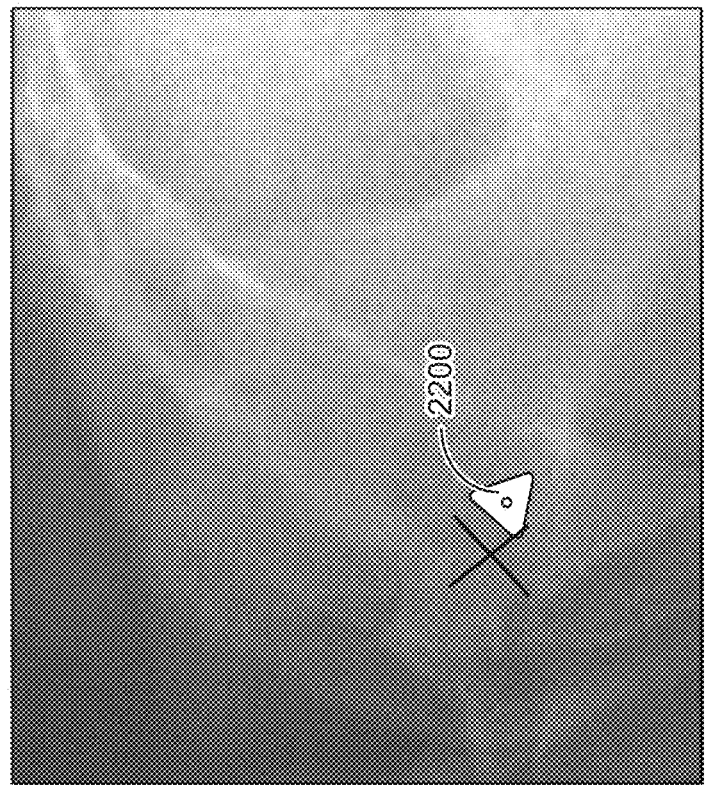
FIGS. 22A-22C illustrate alignment of a soft tissue protector with reference to anatomical landmarks so that the faces of the rectilinear implant are properly oriented with respect to the anatomical landmarks.
Figure 22A:
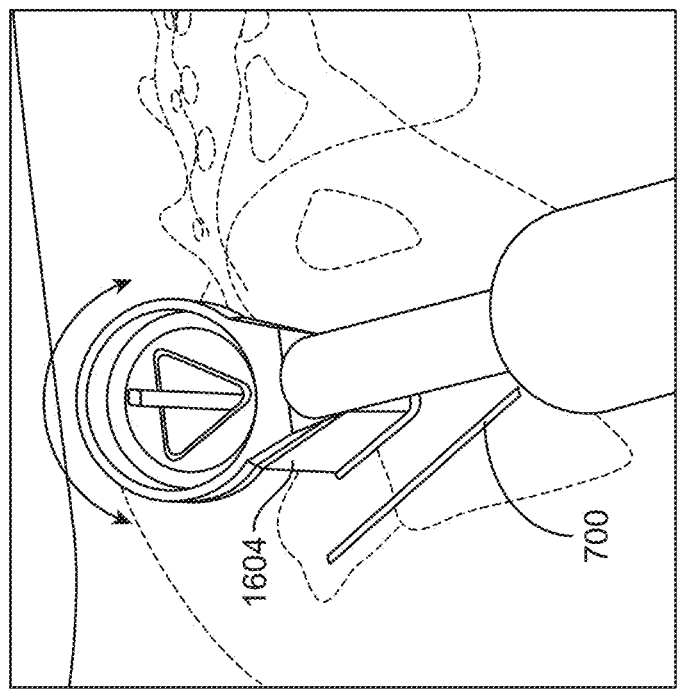
Figure 22C:
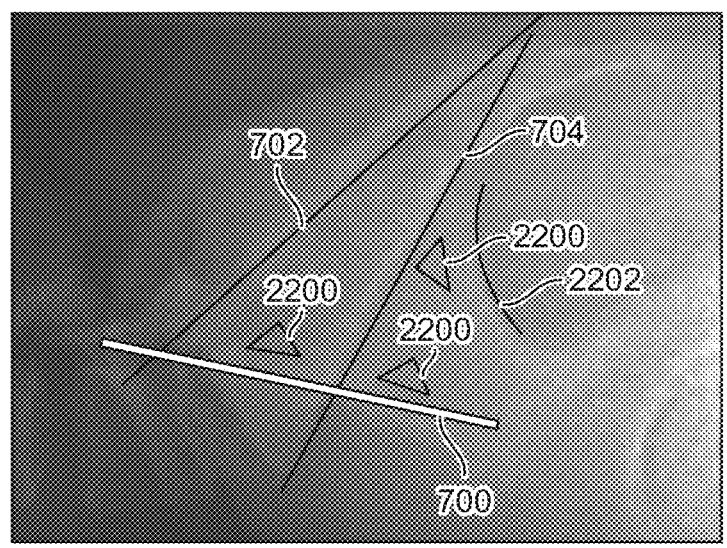

For an implant having a rectilinear cross-sectional profile or a cross-sectional profile defined by a plurality of apices and a plurality of sides, the soft tissue protector 1604 can have a matching cross-sectional profile, as shown in FIGS. 22A and 22B. For the first implant at the first implantation site, the soft tissue protector 1604 can be rotated so that one side of the soft tissue protector is parallel to the alar line 700. In some embodiments, for the second implant at the second implantation site, the soft tissue protector 1604 can also be rotated so that one side of the soft tissue protector is parallel to the alar line 700. This is appropriate when the second implantation site is located at the same distance from the alar line 700 as the first implantation site, as described above. Such a configuration allows the implant 2200 to be positioned close to the alar line without penetrating through the cortices. For the third implant, the soft tissue protector can be rotated so that one side of the soft tissue protector 1604 is facing the greater sciatic notch 2202. FIG. 22C illustrates the orientation of the faces of the implants 2200 to the anatomical landmarks in the lateral view.

Figure 23:
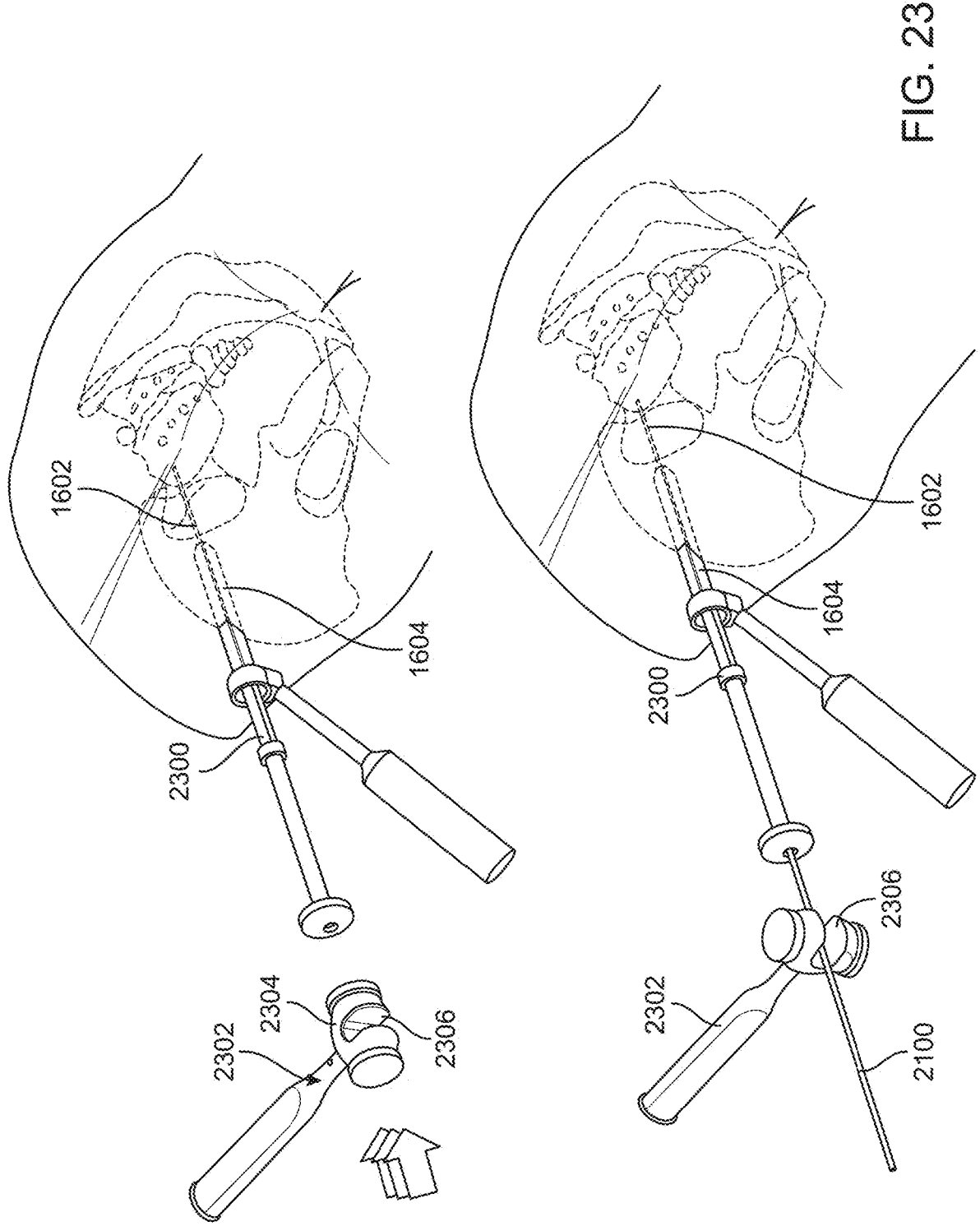
FIG. 23 illustrates shaping the bore with a broach.
Figure 24:
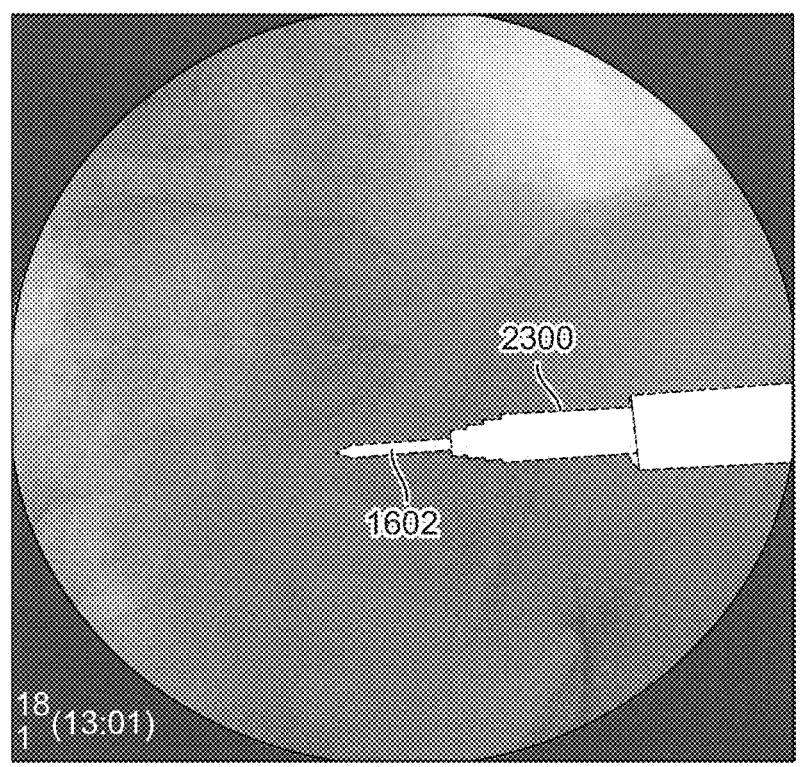
FIG. 24 illustrates broach advancement across the SI-joint.

FIG. 23 illustrates an embodiment of a broach 2300 and a mallet 2302 that can be used to create a rectilinear bore to match the shape of the implant. The broach 2300 has a distal end having a plurality of cutting edges and surfaces for removing bone. The mallet 2302 can have a slot 2306 in the mallet head 204 for receiving an exchange pin 2100 that allows the mallet 2302 to be used in conjunction with the exchange pin 2100. The broach 2300 can be inserted over the guide pin 1602 and into the soft tissue protector 1604 until it contacts the bone. As illustrated in FIG. 24, the broach 2300 can be tapped with the mallet 2302 across the SI-joint under visualization in the outlet view. The broach 2300 can be removed with the exchange pin 2100 in place in order to prevent the guide pin 1602 from withdrawing as the broach 2300 is removed.

Figure 26:
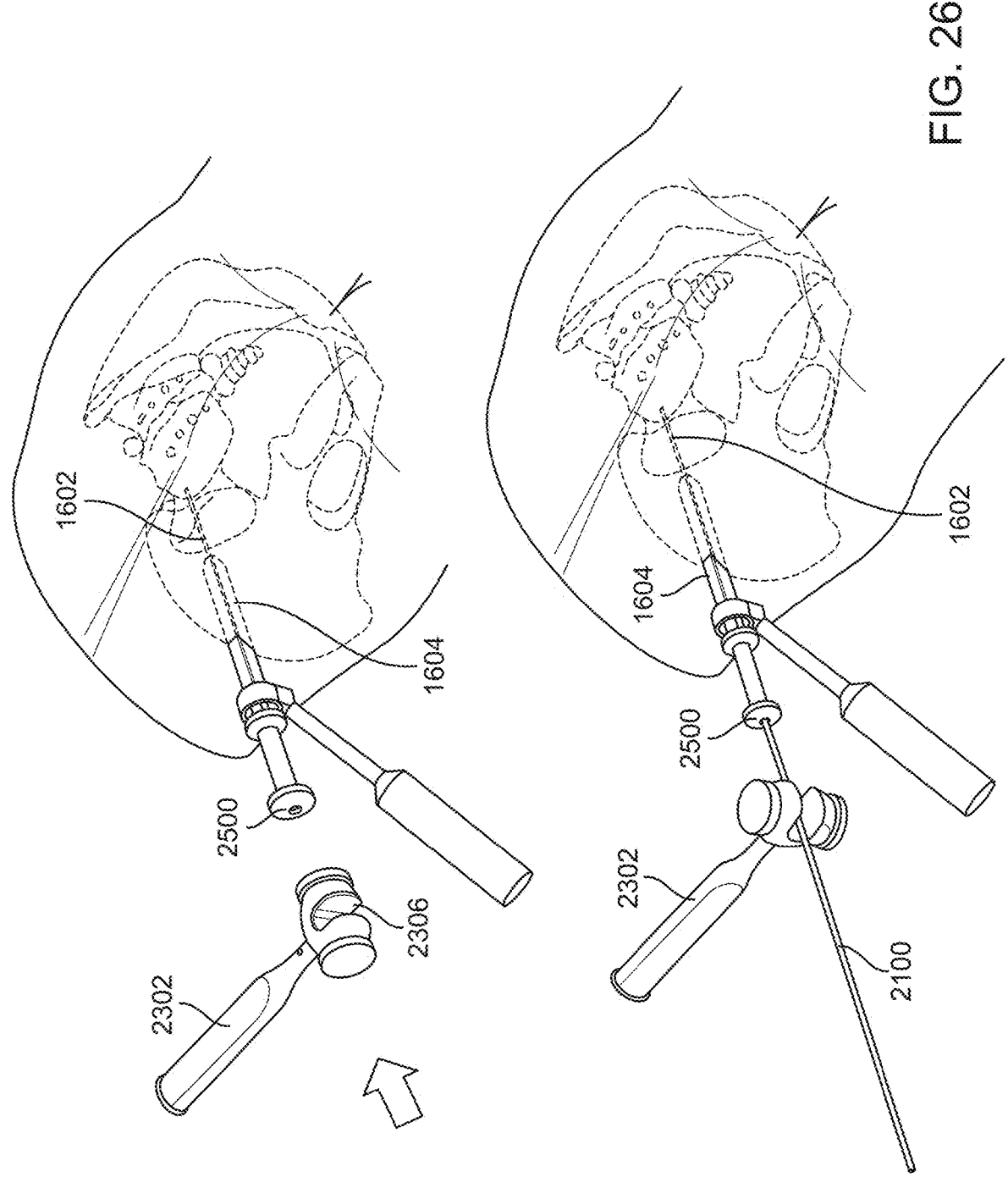
FIG. 26 illustrates implant advancement.
Figure 27B:
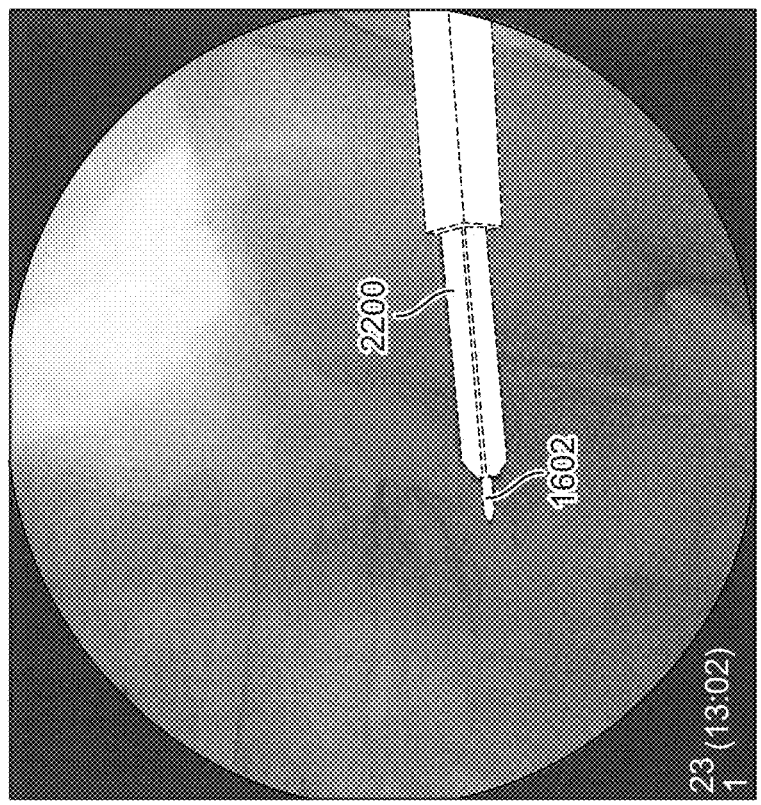
FIGS. 27A and 27B illustrates implant advancement under CT imaging.
Figure 27A:
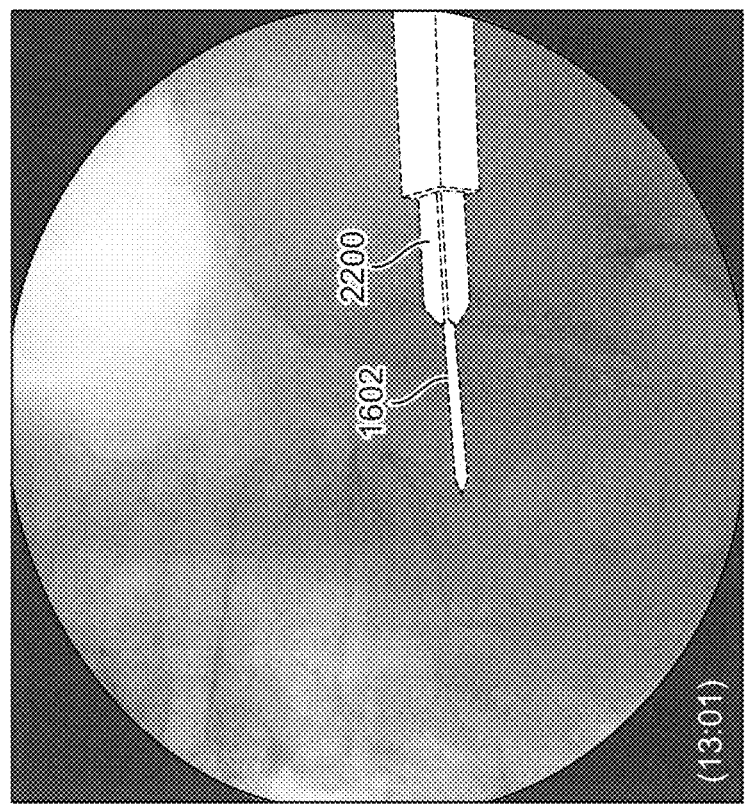
Figure 28:
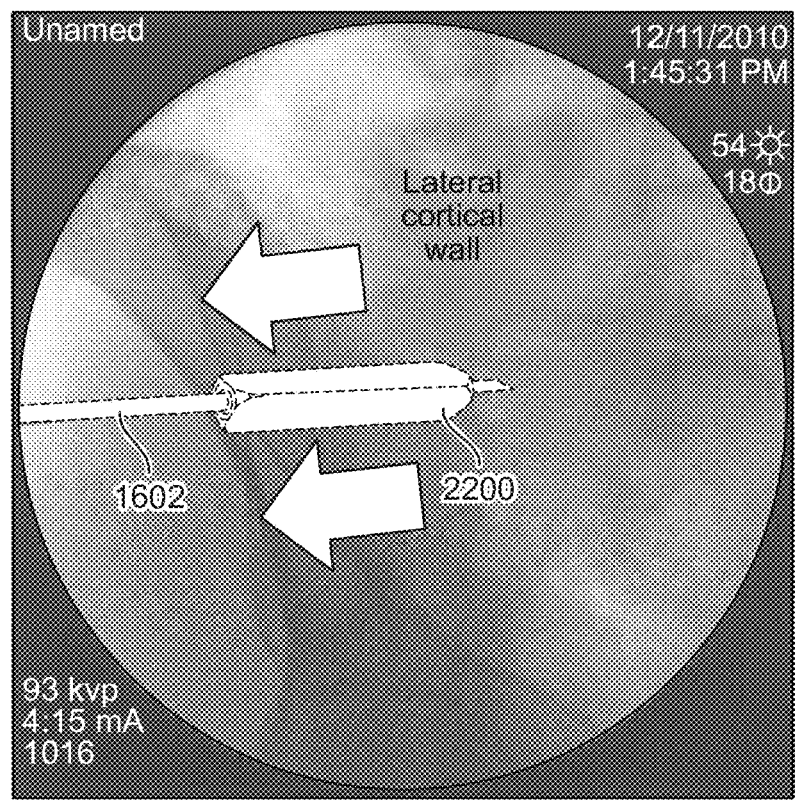
FIG. 28 illustrates implant placement under CT imaging.

After the broach 2300 has been removed, the implant 2200 can be placed over the guide pin 1602 and an impactor 2500 can be used to advance the implant 2200 into the broached bore, as illustrated in FIGS. 25A and 25B. The alignment of the soft tissue protector 1604 can be checked and adjusted as needed so that one side of the soft tissue protector is aligned with the alar line 700. In some embodiments, autograft or allograft bone derived materials, for example the bone materials generated by the drill and broach, can be applied to the implant surface before insertion. Other materials for coating the implant 2200 include growth factors such as bone morphogenetic protein. In some embodiments, the implant 2200 can have a tapered distal end 2202 that is inserted into the bore first. FIG. 26 illustrates a slotted mallet 2302, as described above, being used to strike and advance the impactor 2500 and implant 2200. The slot 2306 in the mallet 2302 can receive an exchange pin 2100 and allows the mallet 2302 to be used in conjunction with an exchange pin 2100, if desired. As illustrated in FIGS. 27A and 27B, implant advancement can be monitored under fluoroscopy in the outlet view to ensure that the implant avoids the foramen. The implant 2200 is advanced until about 2 to 5 mm of the implant remains proud of the surface of the ilium, as shown in FIG. 28.

SI-Joint Implants

Figure 29A:
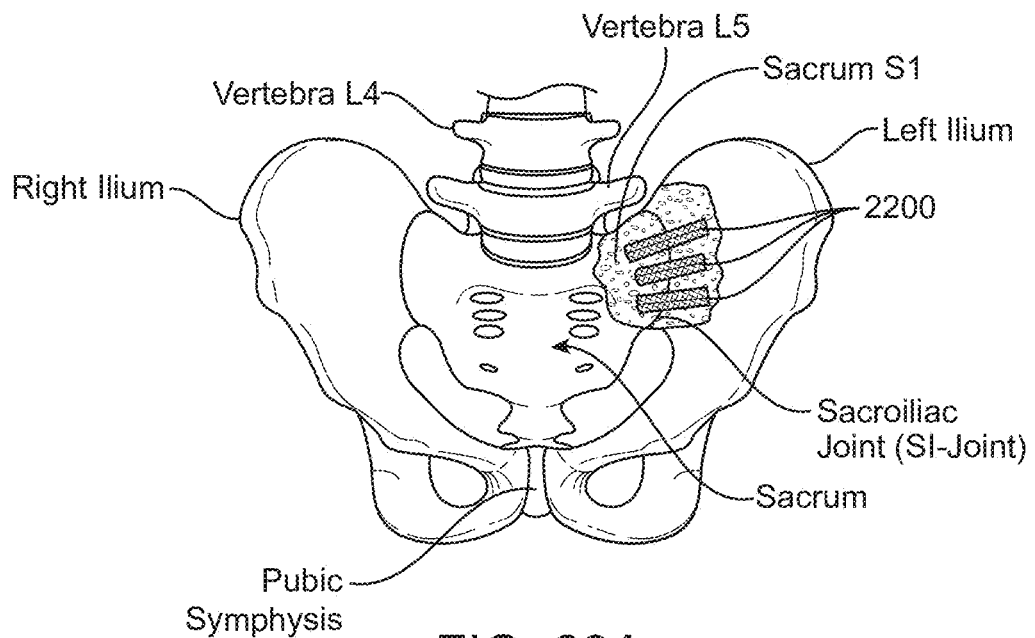
FIGS. 29A and 29B illustrate various types of implants that can be implanted across the SI-joint using the procedures described herein.
Figure 29B:
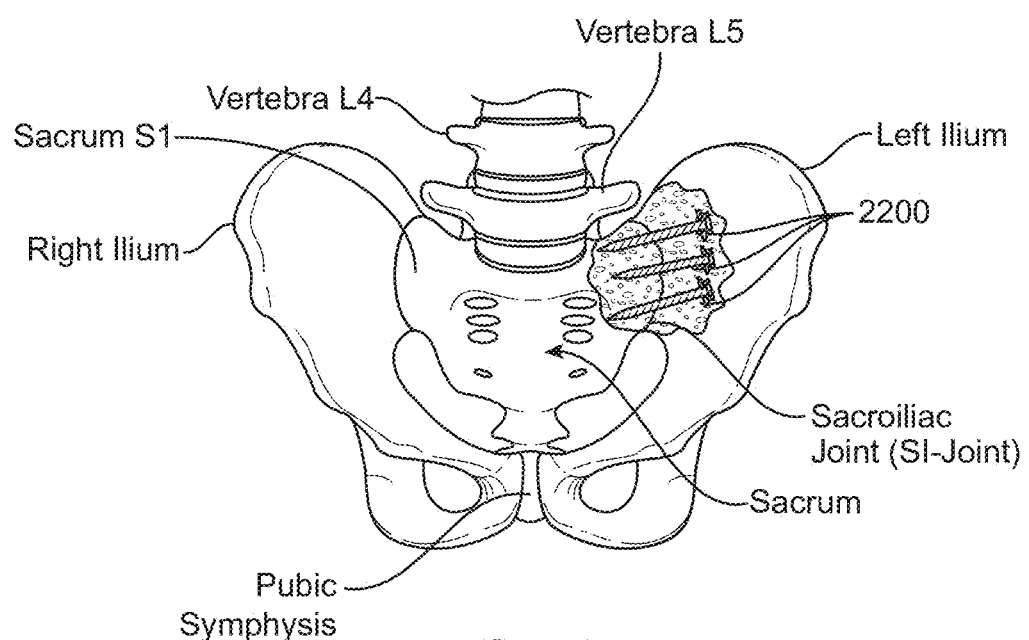

Various implants 2200 can be used for the fixation and fusion of the SI-Joint, as illustrated in FIGS. 29A and 29B. These include screw like implants that are threaded or unthreaded implants or implants with both threaded and unthreaded portions. In some embodiments, the unthreaded implants can have a rectilinear cross-sectional profile transverse to the longitudinal axis of the implant, such as triangular or rectangular. In other embodiments, the unthreaded implants can have a cross-sectional profile defined by one or more apices joined by one or more sides which can be either rectilinear or curvilinear. Implants with a rectilinear cross-sectional profile or a cross-sectional profile defined by one or more apices can better resist rotation than a screw like implant with a circular cross-sectional profile.

Use of a round implant such as a screw type implant may require modifications to portions of the procedure described above including, for example, replacing the soft tissue protector with a standard tubular dilator system, and elimination of the broach and impactor.

Alternative Implant Placement Procedure

The implant placement technique described above places the most cephalad (first) implant, then the next most cephalad (second) implant and then the most caudal (third) implant. Using this numbering system (caudal to cephalad), this technique can be described as a 1-2-3 technique.

An alternative technique using the same implant numbering system can be described as a 3-1-2 technique. This means that the most caudal (third) implant is placed first. The most cephalad (first) implant is placed next, and finally the middle (second) implant is placed last.

The primary goal/advantage of the alternative implant placement technique is to improve the position of the most caudal (third) implant. Generally, the optimal position of the third implant is starting at the midpoint between the first and the second neuroforamen on the outlet view and at the ventral cortical body line on the lateral view. The optimal trajectory for the implant is obtained by aiming the implant toward the middle third or anterior third of the sacral body. By optimizing placement of the third implant, the surgeon will be able to place the longest possible implant in this location. The optimal third implant is aimed between the first and second neuroforamen as opposed to being aimed at the first or second neuroforamen. Longer implants provide better engagement with the sacrum and better biomechanical stability. Optimized implant placement will also facilitate placement of the implant across the articular portion of the joint. This will provide better biomechanical stability and will also provide a more favorable biologic environment for fusion. The placement of the other two implants (first and second) can be generally accomplished as described above. Any variation of the previous method of implanting the other two implants is described below.

Secondary goals/advantages of the alternative implant placement technique are: 1) Increased ease of implant placement/insertion, 2) Shorter operative time, 3) Less radiation exposure to patient and surgeon during the procedure (fewer images required), 4) Improved safety of the procedure. If the pin advances during the procedure, the pin will advance within bone thus lowering the risk of neurologic or other complications, and 5) Expansion of technique to apply to various dysmorphic anatomies.

Technique Steps—Standard Sacrum

In a standard or normal sacrum, placement of sequentially first, positionally third implant using the 3-1-2 technique is as follows. Under a lateral view of the pelvis, lines are marked on the skin to show the position of the alar line, the ventral sacral body line, and the dorsal sacral body line. A surgical incision is made in line with the mid body of the sacrum. Next, under an outlet view, an anchor pin is placed against the ilium at a position above the first foramen. The trajectory of the anchor pin is adjusted so that the anchor pin is parallel to floor and perpendicular to patient (aiming straight medial to lateral). Exact anchor pin position is not necessary as this pin will serve only as an anchor pin for the variable pin guide (VPG), which has a short tube and a long tube that can be rotated with respect to each other and have an adjustable amount of separation between each other. The anchor pin is advanced about 3 cm. Next, under an outlet view, the variable pin guide (VPG) short tube is placed over the anchor pin, and the VPG is opened until the long tube (with inserted guide pin) is pointing just caudal to the midpoint between the first and second neuroforamen. The VPG is then locked in this position. Under a lateral view, the VPG is rotated until the medial tip of the long guide tube (and inserted guide pin) is pointing at the ventral sacral body line. The guide pin is then seated by advancing the guide pin about 5 mm. Under an inlet view, the VPG is removed. The trajectory of the guide pin is adjusted so that the guide pin is aimed towards the anterior third to middle third of the S2 sacral body. Then, under an outlet view, the guide pin is advanced medially to the level of the mid foramen (between $1^{st}$ and $2^{nd}$ foramen). Next, under an inlet view, the surgeon can confirm that the position and trajectory of the guide pin is appropriate. After confirmation, under an outlet view, the surgeon can drill, broach, and place the #3 implant over the pin. Under a lateral view, the implant placement can be confirmed.

After the #3 implant has been placed, the placement of the sequentially second, positionally first implant (#1 implant in the 3-1-2 method) can proceed. Under a lateral view, the VPG short tube is placed over the guide pin used to implant the initially placed implant (#3 implant). The VPG is widened and rotated until the VPG long tube is positioned in the mid portion of the sacral body at a level about 5 to 10 mm caudal to the alar line (iliac cortical density (ICD)). The VPG is then locked and the guide pin is seated about 5 mm. Next, under an inlet view, the surgeon can confirm the trajectory of the guide pin towards the anterior third to middle third of the first sacral body, and adjust the angle and position of the guide pin as necessary. Under an outlet view, the trajectory is adjusted to be parallel with the S1 endplate and the guide pin is advanced above the neural foramen to a point level with the mid portion of the neuroforamen or farther. Then, under an inlet view, the surgeon can confirm that the position of the guide pin is appropriate. Once confirmed, under an outlet view, the surgeon can drill, broach, and place the implant over the pin, and under an inlet view, the position of implant can be confirmed.

After the #1 implant has been placed, placement of the sequentially third, positionally second implant (#2 implant) can be accomplished in a similar manner to the #2 implant placement technique described above for the 1-2-3 technique because abnormalities in the anatomy in this region is very rare, which means that the technique does not require much or any changes. In summary, under a lateral view, using a VPG, a fixed 15 mm pin guide (FPG), or a free hand technique, the tip of the guide pin is positioned and seated caudal to the most cephalad implant and ventral to the ventral sacral body line. The guide pin can be seated about 5 mm. Under an inlet view, the trajectory of the guide pin can be adjusted towards the anterior third to middle third of the sacral body. Under an outlet view, the trajectory of the guide pin is adjusted as necessary, and then the pin is advanced to a point about 5 mm lateral to the lateral border of the first neruoforamen. The outlet oblique view can be utilized to more clearly view the lateral margin of the first neuroforamen. Under an inlet view, the guide pin position can be confirmed. After confirmation, under an outlet view, the surgeon can drill, broach and place the implant over the pin. Then, under an inlet view, the implant position can be confirmed, and a final inlet view image can be taken. Under a lateral view, the implant position can be confirmed, and a final laterial view image can be taken. Under an outlet view, the implant position can be confirmed, and a final outlet view image can be taken.

Sacral Dysmorphism

A spectrum of sacral segment consolidation occurs during development, leading to the presence of residual disk remnants between the vertebral bodies in the sacrum as well as variable fusion patterns between the caudal lumbar vertebra and upper sacral segment. The details of segmentation are subtle, and a variety of upper sacral morphologic types exist as a spectrum from normal to dysmorphic. Patients may not exhibit every characteristic listed.

Characteristics of sacral dysmorphism can be seen under an outlet view, a lateral view, and an inlet view. Under an outlet view, the S1 body may be at or above the level of the iliac crest; mammillary processes may be present in alar area; the upper neural foramina may be misshapen; and the slope may increase from lateral to medial. Under a lateral view, the alar slope may be more acute and a residual disk may be present. Under an inlet view, an anterior cortical indentation may be present.

Figure 30A:
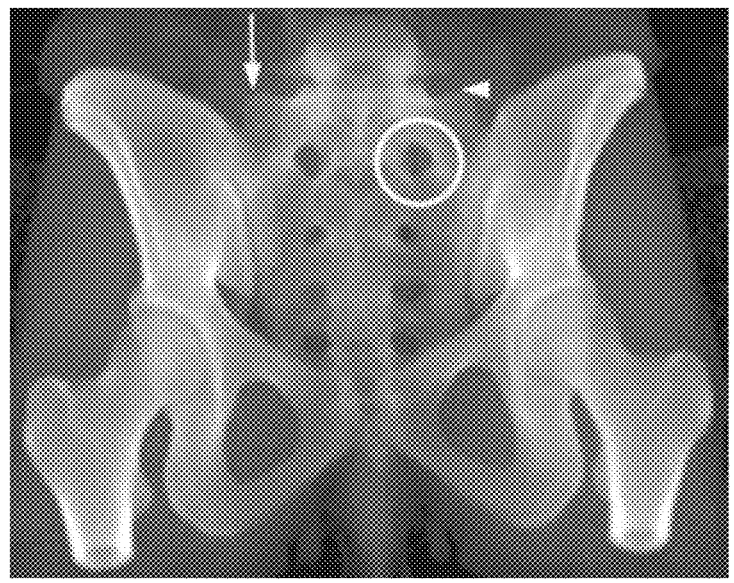
FIGS. 30A and 30B illustratre a dysmorphic and normal sacrum using an outlet view, respectively.
Figure 30B:
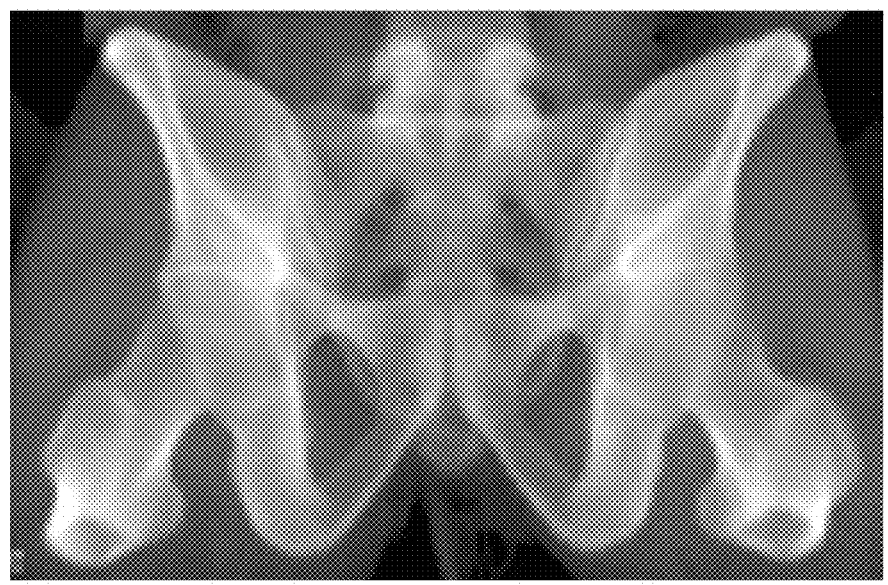

FIGS. 30A and 30B illustratre a dysmorphic and normal sacrum using an outlet view, respectively. The dysmorphic sacrum shown in FIG. 30A can be identified by the height of the S1 endplate, the presence of mammillary process, and irregular neuroforamen. In contrast, the normal sacrum shown in FIG. 30B can be identified by the height of the S1 endplate (relatively lower than dysmorphic sacrum), the absence of mammillary process, and round neuroforamen.

Figure 31A:
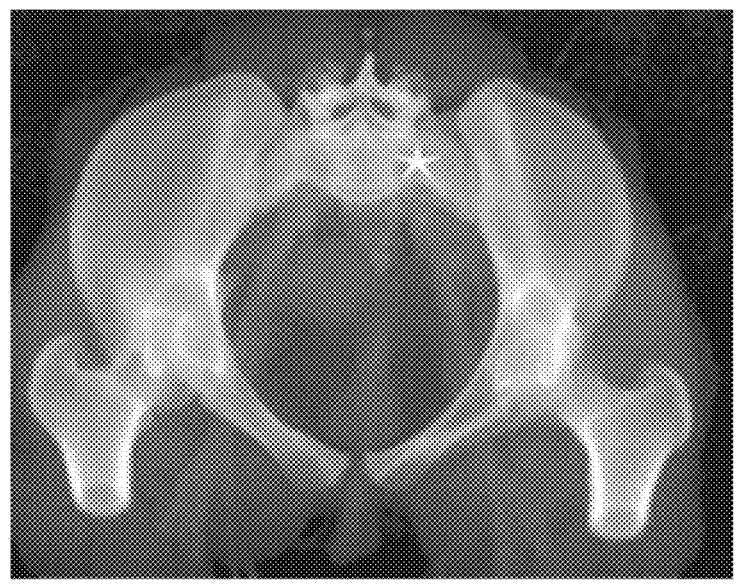
FIGS. 31A and 31B illustrate a dysmorphic and normal sacrum using an inlet view, respectively.
Figure 31B:
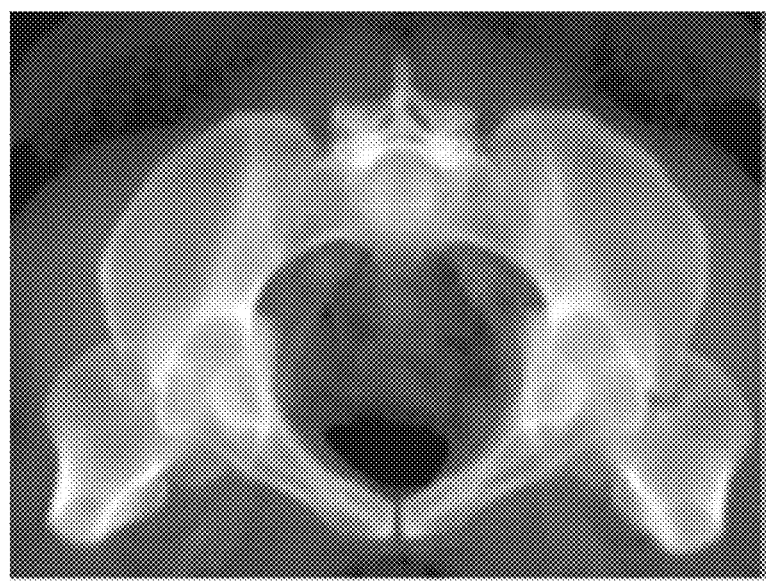

FIGS. 31A and 31B illustrate a dysmorphic and normal sacrum using an inlet view, respectively. The dysmorphic sacrum shown in FIG. 31A can be identified by an anterior cortical indentation in the alar area, while the normal sacrum shown in FIG. 31B shows a smooth anterior alar cortex.

Figure 32A:
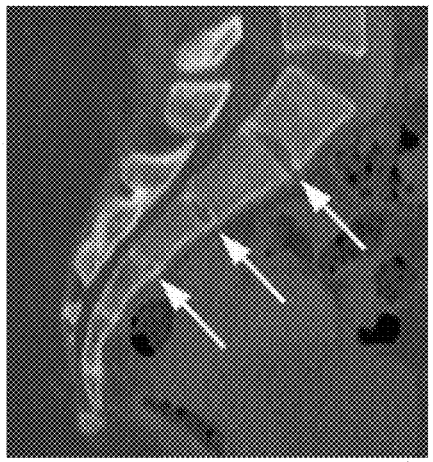
FIGS. 32A and 32B illustrate a dysmorphic sacrum and FIG. 32C illustrates a normal sacrum using a lateral view.
Figure 32B:
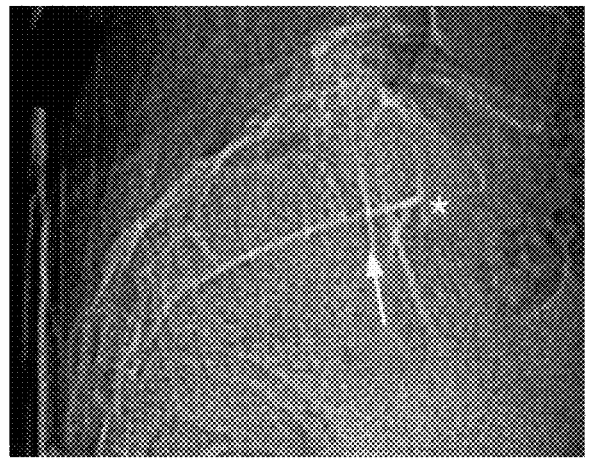
Figure 32C:

FIGS. 32A-32C dysmorphic and normal sacrum using a lateral view, respectively. The dysmorphic sacrum shown in FIGS. 32A and 32B can be identified by residual disk space, increased slope of the ala relative to the sacral endplate, and alar lines that do not superimpose, while the normal sacrum shown in FIG. 32C shows alar lines that are less steep and alar lines that superimpose.

Figure 33A:
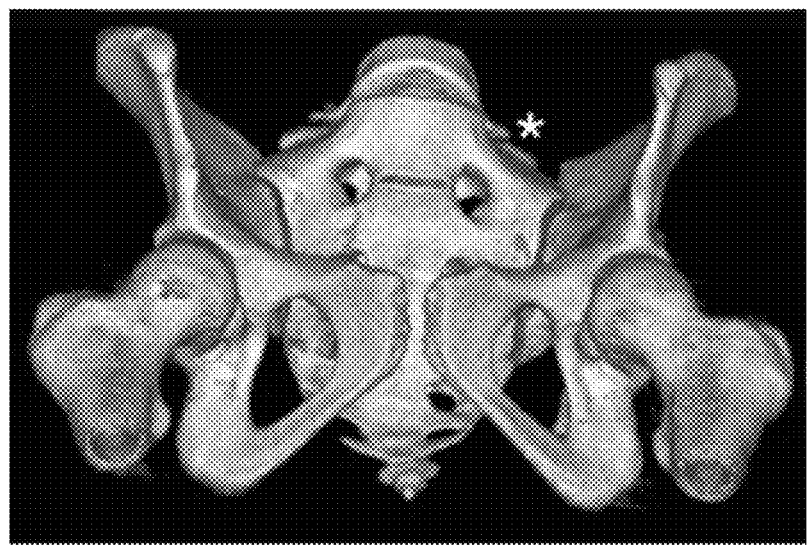
FIGS. 33A and 33B illustrate a dysmorphic sacrum and a normal sacrum using 3D CT imaging, respectively.
Figure 33B:
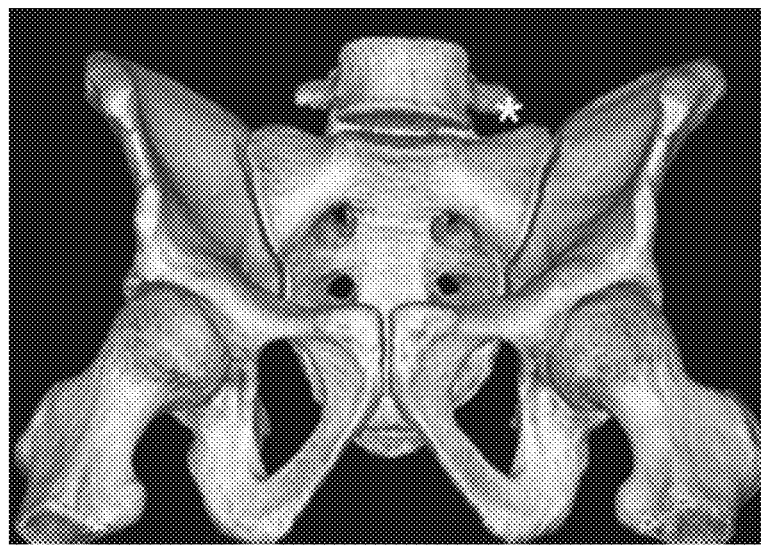
Figure 34:
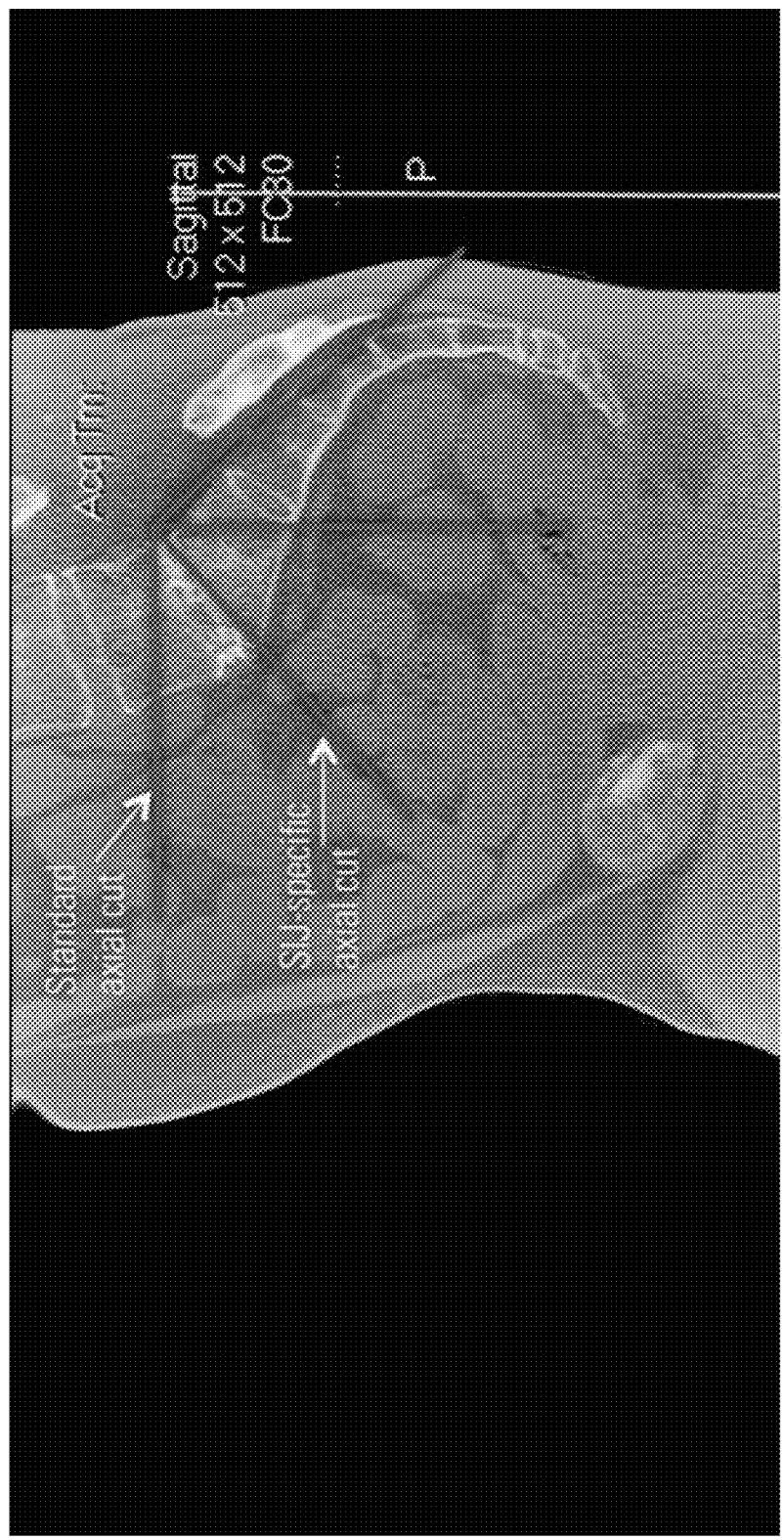
FIG. 34 illustrates various sections that can be taken using a CT scan.

FIGS. 33A and 33B illustrate a dysmorphic sacrum and a normal sacrum using 3D CT imaging, respectively. The dysmorphic sacrum shown in FIG. 33A can be identified by the increasing slope of the ala in the lateral to medial direction, while the normal sacrum shown in FIG. 33B shows a alar area that is relatively flat in the lateral to medial direction. The CT scans of the pelvis with bone and soft tissue facilitates evaluating pelvic structures with special attention to the SI joints. As shown in FIG. 34, the CT scans can be 1-2 mm cuts taken in the sagittal plane (from lateral aspect of left ilium to lateral aspect of right ilium), the axial plane (aligned perpendicular to the posterior body of S1—include all the sacrum-matches inlet view), and the coronal plane (aligned perpendicular to the axial cuts—matches outlet view).

Technique Steps—Dysmorphic Long (2-1-3)

Figure 35:
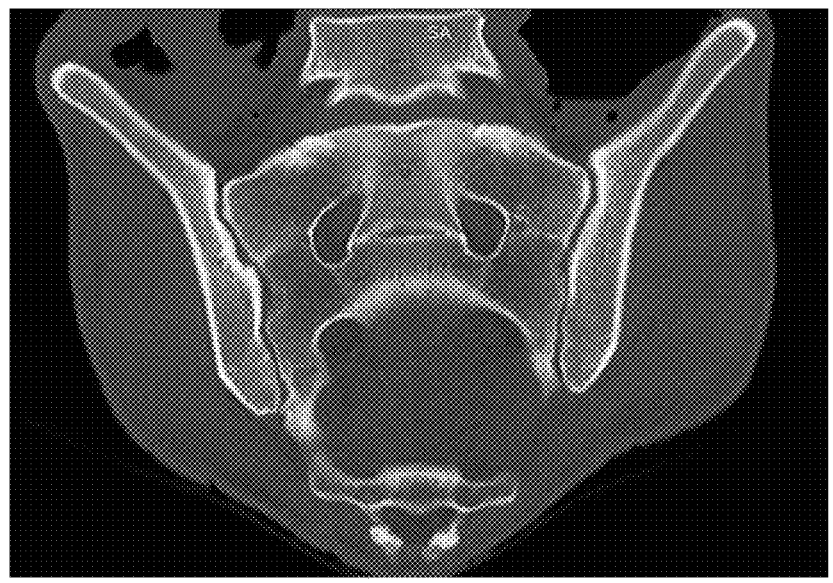
FIG. 35 illustrates a dysmorphic long sacrum.

Some patients may have a dysmorphic sacrum. One dysmorphic sacrum, called a dysmorphic long sacrum and shown in FIG. 35, is characterized by sacralization where the L5 vertebrae becomes part of the sacrum and results in a longer sacrum. The following modified procedure is particularly suitable for patients having a dysmorphic long sacrum.

The procedure begins with the implantation of the sequentially first positionally second (#2) implant. As described above for the normal sacrum procedure, the standard markings can be drawn on the patient and the same skin incision can be made. Under an outlet view, the anchor pin is placed at the level of the first neuroforamen and advanced about 3 cm. Next, under an outlet view, the VPG (short tube) is placed over the anchor pin. The VPG is opened until the VPG long tube (with an inserted guide pin) is at the midpoint between the first and second neuroforamen. The VPG is then locked. Under a lateral view, the VPG is rotated until the long tube (and guide pin) is at mid body or slightly ventral to this. The guide pin is then seated about 5 mm. Under an inlet view, the pin trajectory is confirmed and adjusted as necessary to point to the middle third to anterior third of the sacral body. Next, returning to a lateral view, the pin is repositioned if necessary. Under an outlet view, the guide pin is advanced as medial as possible to a maximum depth of about 70 mm. Under an inlet view, the pin position is confirmed. Under an outlet view, the surgeon can drill, broach, and insert the implant over the pin. Under an inlet view, implant position can be confirmed.

Next, the sequentially second, positionally first (#1) implant can be implanted. Under a lateral view, the VPG (short tube) can be placed over the anchor pin with the long tube (pin) cephalad to the anchor pin. The VPG is rotated and the spread (width) of the VPG is adjusted until the long tube (pin) is seated in mid body at a point about 5-10 mm caudal to the alar line (ICD). The guide pin is then seated about 5 mm. Under an inlet view, the guide pin trajectory is confirmed and adjusted as necessary. Under an outlet view, the guide pin is advanced to within about 5 mm of the lateral wall of the first foramen, and an outlet oblique view is used to assess guide pin depth and relationship to the neuroforamen. Under an inlet view, the pin position can be confirmed. Under an outlet view, the surgeon can drill, broach, and place the implant over the pin. Under an inlet view, the implant placement can be confirmed.

Next, the sequentially third, positionally third (#3) implant can be implanted. Under a lateral view, the VPG (short tube) can be placed over the initially placed anchor pin used to implant the sequentially first implant, with the VPG long tube caudal to the anchor pin. The VPG can be rotated and the spread (width) of the VPG can be adjusted until the long tube (with a guide pin) is seated in mid body at a point at least about 15 mm caudal to the existing guide pin/implant. The guide pin can be seated about 5 mm. Under an inlet view, the guide pin trajectory can be confirmed and adjusted as necessary. Under an outlet view, the guide pin is advanced to within about 5 mm of the lateral wall of the second neuroforamen, and an outlet lateral view is used to assess guide pin depth and relationship to the neuroforamen. Under an inlet view, the guide pin position can be confirmed. Under an outlet view, the surgeon can drill, broach, and place the implant over the pin. Under an inlet view, the implant placement can be confirmed, the soft tissue protector (STP) and pin(s) can be removed, and a final inlet view image can be taken. Under a lateral view, the implant placement can be confirmed and a final lateral view image can be taken. Under an outlet view, the implant placement can be confirmed and a final outlet view image can be taken.

Technique Steps—Dysmorphic Short (1-2 maybe 3)

Figure 36:
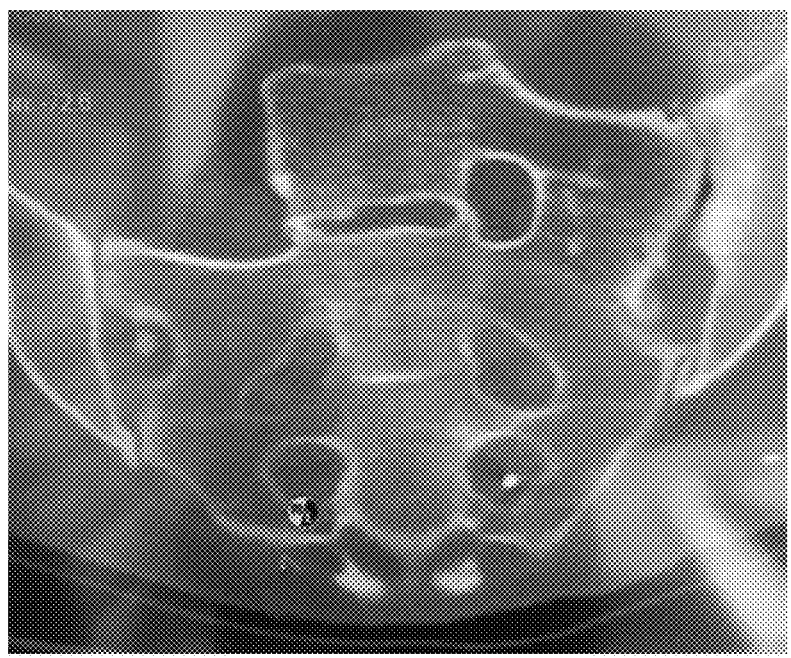
FIG. 36 illustrates a dysmorphic short sacrum.

Another dysmorphic sacram, called a dysmorphic short sacrum and shown in FIG. 36, is characterized by lumbarization, where the S1 vertebrae becomes part of the lumbar spine, which leads to a shorter sacrum. This condition is much less common than the dysmorphic long.

The procedure begins with the implantation of the sequentially first, positionally first (#1) implant. Under a lateral view, standard skin markings are drawn and an incision is made. Under a lateral view, the pin is positioned about 5-10 mm caudal to alar line (ICD) in the mid to anterior third of the sacral body, and the pin is seated about 5 mm. Under an inlet view, the pin trajectory is adjusted to point to the middle third to anterior third of the sacral body. Under an outlet view, the pin is adjusted to be parallel with sacral endplate, and the pin is advanced to point above the first neuroforamen or as far as anatomy allows. Under an inlet view, pin position is confirmed. Under an outlet view, the surgeon can then drill, broach, and place the implant over the pin. Under an inlet view, implant position is confirmed.

Next, the sequentially second, positionally second (#2) implant is implanted. Under a lateral view, a fixed pin guide (FPG) short tube is placed over the pin, and rotated until the tip of FPG long tube (and inserted pin) is at the ventral sacral body line. The pin is seated about 5 mm. Under an inlet view, the pin trajectory is adjusted towards the middle third to anterior third of the sacral body. Under an outlet view, the pin trajectory is adjusted (as necessary) and the pin is advanced as far medially as possible. The outlet oblique view is utilized to better visualize the lateral wall of the neuroforamen. Under an inlet view, the pin position is confirmed. Under an outlet view, the surgeon can drill, broach, and insert the implant over the pin. Under an inlet view, the implant position can be confirmed. Under a lateral view, the implant position can be confirmed.

It is quite likely that there will not be room for a third implant. This assessment will be made based primarily on the final outlet view described above for the #2 implant. If there is room for a third implant, then the steps for the sequentially second implant (above) will be repeated.

While preferred embodiments of the present invention have been shown and described herein, it will be obvious to those skilled in the art that such embodiments are provided by way of example only. Numerous variations, changes, and substitutions are incorporated herein by reference in their entirety. For example, features described in one embodiment may be combined with another embodiment. It is intended that the following claims define the scope of the invention and that methods and structures within the scope of these claims and their equivalents be covered thereby.

What is claimed is:

1. A method of implanting a plurality of implants in a sacroiliac joint (SI-joint), the method comprising:
   inserting a plurality of guide pins into an anterior portion of the SI-joint and into articular cartilage;
   creating a bore around each of the plurality of guide pins; and
   inserting an implant into each bore such that each implant is located in an anterior portion of the SI-joint and into articular cartilage,
   wherein at least one of the plurality of guide pins and at least one implant are inserted anterior of an anterior sacral body line, the anterior sacral body line generally aligned with an anterior sacral cortical wall in a lateral view of the SI-joint.

2. The method of claim 1, further comprising obtaining a lateral view of the pelvis; and
   identifying a plurality of anatomical landmarks in the lateral view of the pelvis including an alar line, an posterior sacral body line, the anterior sacral body line, and an anterior cortex of the sacral alar, wherein the plurality of guide pins are inserted with reference to at least one anatomical landmark.

3. The method of claim 2, wherein at least two guide pins and implants are inserted anterior of the anterior sacral body line in the lateral view of the pelvis.

4. The method of claim 2, wherein the at least one guide pin and implant that is inserted anterior of the anterior sacral body line in the lateral view of the pelvis is angled with respect to a horizontal axis in an inlet view.

5. The method of claim 2, wherein at least two guide pins and two implants are placed parallel to the alar line.

6. The method of claim 2, wherein the plurality of guide pins are parallel in an outlet view.

7. The method of claim 2, further comprising identifying a target for the plurality of guide pins in an inlet view, wherein the target is located in the middle of the sacral body.

8. The method of claim 7, further comprising advancing the guide pins towards the target in the inlet view.

9. The method of claim 1, wherein the implants are non-colinear in the lateral view.

10. The method of claim 1, wherein the implants have an elongate body with a longitudinal axis and a rectilinear cross-sectional profile transverse to the longitudinal axis.

11. The method of claim 1, wherein the implants are screws.

12. A method of implanting a first, second, and third implant in a sacroiliac joint (SI-joint), the method comprising:
    inserting a plurality of guide pins into an anterior portion of the SI-joint and into articular cartilage;
    creating a bore around each of the plurality of guide pins; and
    inserting an implant into each bore such that each implant is located in an anterior portion of the SI-joint and into articular cartilage,
    wherein the first implant that is implanted is a most caudal placed implant, the third implant that is implanted is a most cephalad placed implant, and the second implant that is implanted is a middle placed implant,
    wherein the second implant is inserted anterior of an anterior sacral body line, the anterior sacral body line generally aligned with an anterior sacral cortical wall in a lateral view of the SI-joint.

13. The method of claim 12, wherein the first implant under an inlet view has a trajectory that is aimed towards an anterior third to middle third of a S2 sacral body.

* * * * *